(12) United States Patent
Baker

(10) Patent No.: US 9,028,878 B2
(45) Date of Patent: May 12, 2015

(54) BISMUTH-THIOLS AS ANTISEPTICS FOR BIOMEDICAL USES, INCLUDING TREATMENT OF BACTERIAL BIOFILMS AND OTHER USES

(75) Inventor: Brett Hugh James Baker, Bozeman, MT (US)

(73) Assignee: Microbion Corporation, Bozeman, MT (US)

( * ) Notice: Subject to any disclaimer, the term of this patent is extended or adjusted under 35 U.S.C. 154(b) by 0 days.

(21) Appl. No.: 13/566,816

(22) Filed: Aug. 3, 2012

(65) Prior Publication Data

US 2013/0058983 A1 Mar. 7, 2013

Related U.S. Application Data

(63) Continuation of application No. PCT/US2011/023549, filed on Feb. 3, 2011, and a continuation-in-part of application No. PCT/US2010/023108, filed on Feb. 3, 2010, and a continuation-in-part of application No. 12/699,680, filed on Feb. 3, 2010, now Pat. No. 8,389,021.

(60) Provisional application No. 61/373,188, filed on Aug. 12, 2010, provisional application No. 61/149,593, filed on Feb. 3, 2009.

(51) Int. Cl.
| | |
|---|---|
| *A01N 59/02* | (2006.01) |
| *A61K 9/00* | (2006.01) |
| *A61K 9/06* | (2006.01) |
| *A61K 9/10* | (2006.01) |
| *A61K 9/70* | (2006.01) |
| *A61K 31/095* | (2006.01) |
| *A61K 31/29* | (2006.01) |
| *A61K 33/24* | (2006.01) |

(52) U.S. Cl.
CPC ............ *A61K 9/0014* (2013.01); *A61K 9/06* (2013.01); *A61K 9/10* (2013.01); *A61K 9/7023* (2013.01); *A61K 31/095* (2013.01); *A61K 31/29* (2013.01); *A61K 33/245* (2013.01)

(58) Field of Classification Search
USPC .......... 424/629, 653, 651; 514/345, 363, 706; 504/152
See application file for complete search history.

(56) References Cited

U.S. PATENT DOCUMENTS

| | | | |
|---|---|---|---|
| 2,809,971 | A | 10/1957 | Bernstein et al. |
| 3,523,121 | A | 8/1970 | Lewis et al. |
| RE29,409 | E | 9/1977 | Yeager |
| 4,410,642 | A | 10/1983 | Layton |
| 4,596,724 | A | 6/1986 | Lane et al. |
| 4,788,302 | A | 11/1988 | Costlow et al. |
| 5,028,664 | A | 7/1991 | Ohmura et al. |
| 5,045,555 | A | 9/1991 | Matsumoto et al. |
| 5,229,124 | A | 7/1993 | Rei et al. |
| 5,384,176 | A | 1/1995 | Zimmerman et al. |
| 5,470,586 | A | 11/1995 | Gerhart |
| 5,928,671 | A | 7/1999 | Domenico |
| 6,071,528 | A | 6/2000 | Jensen |
| 6,086,921 | A | 7/2000 | Domenico |
| 6,162,487 | A | 12/2000 | Darouiche |
| 6,248,371 | B1 | 6/2001 | Domenico |
| 6,380,248 | B1 | 4/2002 | Domenico et al. |
| 6,384,040 | B1 | 5/2002 | Walter |
| RE37,793 | E | 7/2002 | Domenico |
| 6,448,306 | B1 | 9/2002 | Lever et al. |
| 6,455,031 | B1 | 9/2002 | Davies et al. |
| 6,488,912 | B1 | 12/2002 | Pfirrmann et al. |
| 6,552,056 | B2 | 4/2003 | Assmann et al. |
| 6,555,599 | B2 | 4/2003 | Lever et al. |
| 6,579,513 | B1 | 6/2003 | Tashjian et al. |
| 6,582,719 | B2 | 6/2003 | Modak et al. |
| 6,638,993 | B2 | 10/2003 | Patel et al. |
| 6,726,898 | B2 | 4/2004 | Jernberg |
| 6,730,324 | B2 | 5/2004 | Troczynski et al. |
| 6,848,871 | B1 | 2/2005 | Cottrell |
| 6,852,782 | B2 | 2/2005 | Patel et al. |
| 6,861,049 | B2 | 3/2005 | Harwood |
| 6,875,453 | B2 | 4/2005 | Viamonte, Jr. |
| 6,943,205 | B2 | 9/2005 | Patel et al. |
| 7,060,739 | B2 | 6/2006 | Patel et al. |
| 7,074,391 | B1 | 7/2006 | Alvarez Hernandez |
| 7,419,681 | B2 | 9/2008 | Törmälä et al. |

(Continued)

FOREIGN PATENT DOCUMENTS

| | | |
|---|---|---|
| AU | 2003 204 105 | 11/2005 |
| EP | 1 363 679 B1 | 1/2002 |

(Continued)

OTHER PUBLICATIONS

Halwani et al., Liposomal bismuth-ethanediol formulation enhances antimicrobial activity of tobramycin, Mar. 15, 2008, International Journal of Pharmaceutics, vol. 358, pp. 278-284.*

(Continued)

*Primary Examiner* — Ali Soroush

(74) *Attorney, Agent, or Firm* — Seed IP Law Group PLLC

(57) ABSTRACT

Compositions and methods, including novel homogeneous microparticulate suspensions, are described for treating natural surfaces that contain bacterial biofilm, including unexpected synergy or enhancing effects between bismuth-thiol (BT) compounds and certain antibiotics, to provide formulations including antiseptic formulations. Previously unpredicted antibacterial properties and anti-biofilm properties of disclosed BT compounds and BT compound-plus-antibiotic combinations are also described, including preferential efficacies of certain such compositions for treating certain gram-positive bacterial infections, and distinct preferential efficacies of certain such compositions for treating certain gram-negative bacterial infections.

13 Claims, 7 Drawing Sheets

(56) References Cited

U.S. PATENT DOCUMENTS

| | | | |
|---|---|---|---|
| 7,507,281 | B2 | 3/2009 | Ong et al. |
| 7,547,433 | B2 | 6/2009 | Jacob et al. |
| 8,389,021 | B2 * | 3/2013 | Baker .......................... 424/653 |
| 2002/0136780 | A1 | 9/2002 | Batarseh |
| 2002/0197282 | A1 | 12/2002 | Mohseni et al. |
| 2006/0205838 | A1 | 9/2006 | Velamakanni et al. |
| 2007/0125703 | A1 | 6/2007 | Chapman et al. |
| 2008/0181950 | A1 | 7/2008 | Bates et al. |
| 2008/0292673 | A1 | 11/2008 | Crudden |
| 2009/0043388 | A1 | 2/2009 | Hsu |
| 2009/0196930 | A1 | 8/2009 | Surber et al. |
| 2009/0197003 | A1 | 8/2009 | Shira |
| 2009/0202610 | A1 | 8/2009 | Wilson |

FOREIGN PATENT DOCUMENTS

| | | |
|---|---|---|
| EP | 1 468 607 A2 | 10/2004 |
| JP | 11-158328 A | 6/1999 |
| JP | 2011-516359 A | 9/2001 |
| JP | 2001516359 A | 9/2001 |
| WO | 99/21568 A1 | 5/1999 |
| WO | 99/39707 A1 | 8/1999 |
| WO | 01/64644 A1 | 9/2001 |
| WO | 02/077095 A2 | 10/2002 |
| WO | 2008/092011 A2 | 7/2008 |
| WO | 2009/154819 A2 | 12/2009 |

OTHER PUBLICATIONS

Domenico et al., "Activities of Bismuth Thiols Against Staphylococci and Staphylococcal Biofilms", May 2001, Antimicrobial Agents and Chemotherapy, vol. 45 No. 5, pp. 1417-1421.*

Rupp et al., Effect of Subinhibitory Concentrations of Vancomycin, Cefazolin, Ofloxaxin, L-Ofloxaxin and D-Ofloxaxin on Adherence to Intravascular Catheters and Biofilm Formation by *Staphylococcus epidermidis*, Published 1998, vol. 41, pp. 155-161.*

Agocs et al., "The Structurally Flexible Bicyclic Bis(2-hydroxyethanethiolato)bismuth(III) Complex: A Model for Asymmetric Monoanionic Chelation of Bismuth(III)," *Inorg. Chem.* 36:2855-2860, 1997.

Agocs et al., "Spectroscopic, Structural, and Mass Spectrometric Studies on Two Systematic Series of Dithiabismuth (III) Heterocycles: Identification of Bismuthenium Cations and Their Solvent Complexes," *J. Am. Chem. Soc.* 118:3225-3232, 1996.

Alt et al., "In Vitro Testing of Antimicrobial Activity of Bone Cement," *Antimicrobial Agents and Chemotherapy* 48(11):4084-4088, 2004.

Badireddy et al., "Bismuth Dimercaptopropanol (BisBAL) Inhibits the Expression of Extracellular Polysaccharides and Proteins by *Brevundimonas diminuta*: Implications for Membrane Microfiltration," *Biotechnology and Bioengineering* 99:634-643, 2008.

Badireddy et al., "Spectroscopic Characterization of Extracellular Polymeric Substances from *Escherichia coli* and *Serratia marcescens*: Suppression Using Sub-Inhibitory Concentrations of Bismuth Thiols," *Biomacromolecules* 9:3079-3089, 2008.

Bayston et al., "An antimicrobial modified silicone peritoneal catheter with activity against both Gram positive and Gram negative bacteria," *Biomaterials* 30:3167-3173, 2009.

Bohner et al., "Gentamicin-Loaded Hydraulic Calcium Phosphate Bone Cement as Antibiotic Delivery System," *Journal of Pharmaceutical Sciences* 86(5):565-572, May 1997.

Brogan et al., "Bismuth-dithiol inhibition of the *Escherichia coli* rho transcription termination factor," *Journal of Inorganic Biochemistry* 99:841-851, 2005.

Bueno et al., "Study of the bismuth oxide concentration required to provide Portland cement with adequate radiopacity for endodontic," *Oral Surg. Oral Med. Oral Pathol. Oral Radiol. Endod.* 107:e65-e69, 2009.

Cape et al., "Preparation of Active Proteins, Vaccines and Pharmaceuticals as Fine Powders using Supercritical or Near-Critical Fluids," *Pharmaceutical Research* 25(9):1967-1990, 2008.

Chandler et al., "Mechanism of the Antimicrobial Action of Pyrithione: Effects on Membrane Transport, ATP Levels, and Protein Synthesis," *Antimicrobial Agents and Chemotherapy* 14(1):60-68, 1978.

Chuard et al., "Susceptibility of *Staphylococcus aureus* Growing on Fibronectin-Coated Surfaces to Bactericidal Antibiotics," *Antimicrobial Agents and Chemotherapy* 37(4):625-632, 1993.

Codony et al., "Assessment of bismuth thiols and conventional disinfectants on drinking water biofilms," *Journal of Applied Microbiology* 95:288-293, 2003.

Cooksey, "Genetics of Bactericide Resistance in Plant Pathogenic Bacteria," *Annu. Rev. Phytopathol.* 28:201-219, 1990.

Crane et al., "Efficacy of Colistin-Impregnated Beads to Prevent Multidrug-Resistant *A. baumannii* Implant-Associated Osteomyelitis," *Journal of Orthopaedic Research* 27:1008-1015, Aug. 2009.

De Lalla, "Antibiotic Prophylaxis in Orthopedic Prosthetic Surgery," *Journal of Chemotherapy* 13(1):48-53, 2001.

Domenico et al., "Efficacy/Toxicity of Bismuth-Dimercaprol (BisBAL) in a Burn Wound Sepsis Model," *Abstracts of the General Meeting of the American Society for Microbiology, the Society*, Washington, DC, US, 96:135, Jan. 1, 1996.

Domenico et al, "Enhancement of Bismuth Antibacterial Activity with Lipophilic Thiol Chelators," *Antimicrobial Agents and Chemotherapy* 41(8):1697-1703, Aug. 1997.

Domenico et al., "Activities of Bismuth Thiols against Staphylococci and Staphylococcal Biofilms," *Antimicrobial Agents and Chemotherapy* 45(5):1417-1421, May 2001.

Domenico et al., "Surface Antigen Exposure by Bismuth Dimercaprol Suppression of *Klebsiella pneumoniae* Capsular Polysaccharide," *Infection and Immunity* 67(2):664-669, 1999.

Domenico et al., "The Potential of Bismuth-Thiols for Treatment and Prevention of Infection," *Infect. Med.* 17(2):123-127, 2000.

Domenico et al., "Combating Antibiotic Resistance with Bismuth-Thiols," *Res. Adv. In Antimicrob. Agents & Chemother.* 3:79-85, 2003.

Domenico et al., "Differential Effects of Bismuth and Salicylate Salts on the Antibiotic Susceptibility of *Pseudomonas aeruginosa*," *Eur. J. Clin. Microbial. Infect. Dis.* 11: 170-175, 1992.

Domenico et al., "Bismuth Modulation of Antibiotic Activity Against Gastrointestinal Bacterial Pathogens," *Med. Microbiol. Lett.* 3:114-119, 1994.

Domenico et al., "BisEDT and RIP act in synergy to prevent graft infections by resistant Staphylococci," *Peptides* 25:2047-2053, 2004.

Domenico et al., "Subinhibitory bismuth ethanedithiol (BisEDT) sensitizes resistant *Staphylococcus aureus* to nafcillin or gentamicin," Annual meeting ASM, Salt Lake, City, UT, 2003 (p. 145).

Domenico et al., "Extracellular polysaccharide production by *Klebsiella pneumoniae* and its relationship to virulence," *Can. J. Microbiol.* 31:472-478, 1985.

Domenico et al., "Reduction of capsular polysaccharide and potentiation of aminoglycoside inhibition in Gram-negative bacteria by bismuth subsalicylate," *Journal of Antimicrobial Chemotherapy* 28:801-810, 1991.

Domenico et al., "Salicylate or Bismuth Salts Enhance Opsonophagocytosis of *Klebsiella pneumoniae*," *Infection* 20:66-72, 1992.

Domenico et al., "Resistance to bismuth among Gram-negative bacteria is dependent upon iron and its uptake," *Journal of Antimicrobial Chemotherapy* 38:1031-1040, 1996.

Domenico et al., "Polysaccharide Capsule-Mediated Resistance to Opsonophagocytosis in *Klebsiella pneumoniae*," *Infection and Immunity* 62(10):4495-4499, 1994.

Domenico et al., "Antimicrobial Activity of Novel Antimicrobial Agents: Pyrithione Enhanced Antimicrobial Activity of Bismuth," *Antibiotics for Clinicians* 9:291-297, 2005.

Drosou et al., "Antiseptics on Wounds: an Area of Controversy," *Wounds* 15(6):1-27, 2003.

El-Feky et al., "Effect of Ciprofloxacin and N-acetylcysteine on Bacterial Adherence and Biofilm Formation on Ureteral Stent Surfaces," *Polish Journal of Microbiology* 58(3):261-267, 2009.

(56) References Cited

OTHER PUBLICATIONS

Expert, "Withholding and Exchanging Iron: Interactions Between *Erwinia* spp. and Their Plant Hosts," *Annu. Rev. Phytopathol* 37:307-334, 1999.

Halwani et al., "Bismuth-thiol incorporation enhances biological activities of liposomal tobramycin against bacterial biofilm and quorum sensing molecules production by *Pseudomonas aeruginosa*," *International Journal of Pharmaceutics* 373:141-146, 2009.

den Hollander et al., "Use of Pharmacodynamic Parameters to Predict Efficacy of Combination Therapy by Using Fractional Inhibitory Concentration Kinetics," *Antimicrobial Agents and Chemotherapy* 42(4):744-748, 1998.

Holleman et al., Lehrbuch der Anorganischen Chemie, Walter de Gruyter, New York, vol. 91-100, p. 1003, 1985.

Huang et al., "Reduction of polysaccharide production in *Pseudomonas aeruginosa* biofilms by bismuth dimercaprol (BisBAL) treatment," *Journal of Antimicrobial Chemotherapy* 44:601-605, 1999.

Hwang et al., "Chemical composition, radiopacity, and biocompatibility of Portland cement with bismuth oxide," *Oral Surg. Oral Med. Oral Pathol. Oral Radiol. Endod.* 107:e96-e102, 2009.

Imazato, "Antibacterial properties of resin composites and dentin bonding systems," *Dental Materials* 19:449-457, 2003.

Kuvshinova et al., "Reaction of Bismuth Nitrate with Sodium Citrate in Water-Glycerol Solutions," *Russian Journal of Inorganic Chemistry* 54(11):1816-1819, 2009.

Lambert et al., "The actions of bismuth in the treatment of *Helicobacter pylori* infection," *Aliment Pharmacol Ther* 11(1):27-33, 1997.

Lee et al., "Inhibition of Methicillin-Resistant *Staphylococcus aureus* Biofilm Formation with Bismuth-Thiol Compounds," *Abstracts of the General Meeting of the American Society for Microbiology, the Society*, Washington, DC, US, 104:111, Jan. 1, 2004.

Martin et al., "Micronization processes with supercritical fluids: Fundamentals and mechanisms," *Advanced Drug Delivery Reviews* 60:339-350, 2008.

McManus et al., "Antibiotic Use in Plant Agriculture," *Annu. Rev. Phytopathol.* 40:443-465, 2002.

Meletiadis et al., "Assessing in vitro combinations of antifungal drugs against yeasts and filamentous fungi: comparison of different drug interaction models," *Medical Mycology* 43:133-152, 2005.

Moribe et al., "Supercritical carbon dioxide processing of active pharmaceutical ingredients for polymorphic control and for complex formation," *Advanced Drug Delivery Reviews* 60:328-338, 2008.

Odds, "Synergy, antagonism, and what the chequerboard puts between them," *Journal of Antimicrobial Chemotherapy* 52:1, 2003.

Peterson et al., "Therapeutic Role for Bismuth Compounds in TNBS-Induced Colitis in the Rat," *Digestive Diseases and Sciences* 45(3):466-473, 2000.

Rasenack et al., "Micron-Size Drug Particles: Common and Novel Micronization Techniques," *Pharmaceutical Development and Technology* 9(1):1-13, 2004.

Sadler et al., "Coordination chemistry of metals in medicine: target sites for bismuth," *Coordination Chemistry Reviews* 185-186:689-709, 1999.

Salo et al., "Salicylate-Enhanced Exposure of *Klebsiella pneumoniae* Subcapsular Components," *Infection* 23(6):371-377, 1995.

Soothill et al., "The $IC_{50}$: an exactly defined measure of antibiotic sensitivity," *Journal of Antimicrobial Chemotherapy* 29:137-139, 1992.

Veloira et al., "In vitro activity and synergy of bismuth thiols and tobramycin against *Burkholderia cepacia* complex," *Journal of Antimicrobial Chemotherapy* 52:915-919, 2003.

Weber et al., "Metal-1,4-Dithio-2,3-dihydroxybutane Chelates: Novel Inhibitors of the Rho Transcription Termination Factor," *Biochemistry* 42(30):9121-9126, 2003.

Widmer et al., "Killing of Nongrowing and Adherent *Escherichia coli* Determines Drug Efficacy in Device-Related Infections," *Antimicrobial Agents and Chemotherapy* 35(4):741-746, 1991.

Wu et al., "Subinhibitory Bismuth-Thiols Reduce Virulence of *Pseudomonas aeruginosa*," *Am. J. Respir. Cell Mol. Biol.* 26:731-738, 2002.

Zhang et al., "Inhibition of Bacterial Adherence on the Surface of Stents and Bacterial Growth in Bile by Bismuth Dimercaprol," *Digestive Diseases and Sciences* 50(6):1046-1051, 2005.

Smith et al., "Bismuth compounds as fungicides," International Pest Control, pp. 144-145, 1985, 2 pages (+ English abstract).

\* cited by examiner

BISMUTH-THIOLS AS ANTISEPTICS FOR BIOMEDICAL USES, INCLUDING TREATMENT OF BACTERIAL BIOFILMS AND OTHER USES

CROSS REFERENCE TO RELATED APPLICATIONS

This application is a continuation of PCT Application No. PCT/US2011/023549 filed Feb. 3, 2011; which claims the benefit under 35 U.S.C. §119(e) of U.S. Provisional Application No. 61/373,188 filed Aug. 12, 2010; and which also claims the benefit under 35 U.S.C. §120 of PCT Application No. PCT/US2010/023108, filed Feb. 3, 2010; each of which prior applications is incorporated herein by reference in its entirety. This application is also a continuation-in-part of PCT Application No. PCT/US2010/023108, filed Feb. 3, 2010; which claims the benefit under 35 U.S.C. §119(e) of U.S. Provisional Application No. 61/149,593, filed Feb. 3, 2009; and this application is also a continuation-in-part of U.S. patent application Ser. No. 12/699,680, filed Feb. 3, 2010; which claims the benefit under 35 U.S.C. §119(e) of U.S. Provisional Application No. 61/149,593, filed Feb. 3, 2009; each of which prior applications is incorporated herein by reference in its entirety.

BACKGROUND

1. Technical Field

The presently disclosed invention embodiments relate to compositions and methods for the treatment of microbial infections. In particular, the present embodiments relate to improved treatments for managing bacterial infections in epithelial tissues, including in wounds such as chronic wounds and acute wounds, and in clinical, personal healthcare, and other contexts, including treatment of bacterial biofilms and other conditions.

2. Description of the Related Art

The complex series of coordinated cellular and molecular interactions that contribute to skin wound healing and responding to and resisting microbial infections and/or to healing or maintenance of bodily tissues generally, may be adversely impacted by a variety of external factors, such as opportunistic and nosocomial infections (e.g., clinical regimens that can increase the risk of infection), local or systemic administration of antibiotics (which may influence cell growth, migration or other functions and can also select for antibiotic-resistant microbes), frequent wound dressing changes, open-air exposure of wounds to speed healing, the use of temporary artificial structural support matrix or scaffold materials, the possible need for debridement and/or repeat surgery to excise infected or necrotic tissue and/or other factors.

Wound healing thus continues to be a formidable challenge for clinical practitioners worldwide. The current treatments for recalcitrant wounds are impractical and ineffective, often requiring multiple surgeries to close the wound. For instance, becaplermin, sold under the trademark REGRANEX® (Ortho-McNeil Pharmaceutical, Inc., available from Ethicon, Inc., recombinant platelet-derived growth factor) exemplifies one of the few available treatments for chronic wounds, but is expensive to produce and has limited clinical utility.

Chronic and Acute Wounds and Wound Biofilms

Wounds occur when the continuity between cells within a tissue, or between tissues, is disrupted, for instance, by physical, mechanical, biological, pathological and/or chemical forces (e.g., burns, dermal infections, puncture wounds, gunshot or shrapnel wounds, skin ulcers, radiation poisoning, malignancies, gangrene, autoimmune disease, immunodeficiency disease, respiratory insult such as by inhalation or infection, gastrointestinal insult such as by deleterious ingestion or infection, circulatory and hematologic disorders including clotting defects,) or other traumatic injuries, or the like.

While a limited level of bacterial contamination in a wound, or "colonization" of the wound, may not necessarily interfere with the processes of wound healing, the presence of bacteria in numbers sufficient to overwhelm the host immune defenses can lead to an acute wound or a chronic wound or a wound in which a bacterial biofilm is present, such as a wound infection in which bacterial growth proceeds to the detriment of the host. Bryant and Nix, *Acute and Chronic Wounds: Current Management Concepts,* 2006 Mosby (Elsevier), NY; Baronoski, *Wound Care Essentials: Practical Principles* (2nd Ed.), 2007 Lippincott, Williams and Wilkins, Philadelphia, Pa.). For example, acute wounds such as may result from injury, trauma, surgical intervention, or other causes, typically lack underlying health deficits and heal rapidly, but may on occasion fail to do so due to the presence of an infection; rapidly forming bacterial biofilms have been described in acute wounds (e.g., WO/2007/061942). Additional factors that may contribute to the development of chronic wounds include losses in mobility (e.g., that result in continued pressure being applied to a wound site), deficits of sensation or mental ability, inaccessibility of the wound site (e.g., in the respiratory or gastrointestinal tracts) and circulatory deficits. Infection at a chronic wound site may be detected by the clinical signs of skin redness, edema, pus formation and/or unpleasant odor, or other relevant, clinically accepted criteria.

Acute wounds that cannot heal properly may thus be present, and chronic wounds thus may develop, in higher organisms (including but not limited to humans and other mammals) when the host's immune system has been overwhelmed by bacterial infection of a wound site (e.g., an acute wound), creating permissive conditions for bacteria to invade and further destroy tissue. In general, chronic wounds are wounds that do not heal within three months, and instead of becoming smaller they tend to grow larger as the bacterial infiltration progresses. Chronic wounds may become very painful and stressful for the patient when nearby nerves become damaged (neuropathy) as the wound progresses. These wounds affect four million Americans each year and cost about $9 billion in treatment expenses. Afflicted individuals are mostly over the age of 60.

Chronic wounds may in some cases originate as acute wounds and thus may include, for example, gunshot or shrapnel wounds, burns, punctures, venous ulcers, pressure ulcers, diabetic ulcers, radiation poisoning, malignancies, dermal infections, gangrene, surgical wounds, diabetic foot ulcers, dicubitis ulcers, venous leg ulcers, infected and/or biofilm-containing nonhealing surgical wounds, pyoderma gangrenosum, traumatic wounds, acute arterial insufficiency, necrotizing fasciitis, osteomyelitis (bone infection), and radiation injuries, such as osteoradionecrosis and soft tissue radionecrosis, or other types of wounds. Venous ulcers, for example, occur mostly in the legs, as a result of poor circulation (e.g., ischemia), malfunctioning valves of veins, or repeated physical trauma (e.g., repetitive injury). Pressure ulcers may be present when local pressure that is exerted at or around a wound site is greater than blood pressure, for instance, such that poor circulation, paralysis, and/or bed sores may contribute to, or exacerbate, the chronic wound. Diabetic ulcers may occur in individuals with diabetes mellitus, for example, persons in whom uncontrolled high blood sugar can contribute to a loss of feeling in the extremities, leading to repetitive injuries and/or neglect on the part of the individual to attend to injuries. Factors that can complicate or otherwise influence clinical onset and outcome of chronic wounds include the subject's immunological status (e.g., immune suppression, pathologically (e.g., HIV-AIDS), radiotherapeutically or pharmacologically compromised immune system; age; stress); skin aging (including photochemical aging), and development and progression of biofilms within the wound. In the case of epithelial tissues in the respiratory and/or gastrointestinal tracts, inaccessibility, occlusion, difficulty in generating epithelial surface-clearing fluid forces or development of localized microenvironments conducive to microbial survival can engender clinical complications.

Wound-related injuries may be accompanied by lost or compromised organ function, shock, bleeding and/or thrombosis, cell death (e.g., necrosis and/or apoptosis), stress and/or microbial infection. Any or all of these events, and especially infection, can delay or prevent the effective tissue repair processes that are involved in wound healing. Hence, it can be important as early as possible in an individual who has sustained a wound to remove nonviable tissue from a wound site, a process referred to as debridement, and also to remove any foreign matter from the wound site, also referred to as wound cleansing.

Severe wounds, acute wounds, chronic wounds, burns, and ulcers can benefit from cellular wound dressings. Several artificial skin products are available for nonhealing wounds or burns such as the artificial skin products sold under the trademarks: APLIGRAFT® (Norvartis), DERMAGRAFT®, BIOBRANE®, TRANSCYTE® (Advance Tissue Science), INTEGRA® DERMAL REGENERATION TEMPLATE® (from Integra Life Sciences Technology), and ORCEL®. These products, however, are not designed to address the problem of bacterial tissue infiltration and wound spreading.

Unfortunately, systemic antibiotics are not effective for the treatment of chronic wounds, and are generally not used unless an acute bacterial infection is present. Current approaches include administration or application of antibiotics, but such remedies may promote the advent of antibiotic-resistant bacterial strains and/or may be ineffective against bacterial biofilms. It therefore may become especially important to use antiseptics when drug resistant bacteria (e.g., methicillin resistant *Staphylococcus aureus*, or MRSA) are detected. There are many antiseptics widely in use, but bacterial populations or subpopulations that are established may not respond to these agents, or to any other currently available treatments. Additionally, a number of antiseptics may be toxic to host cells at the concentrations that may be needed to be effective against an established bacterial infection, and hence such antiseptics are unsuitable. This problem may be particularly acute in the case of efforts to clear infections from natural surfaces, including internal epithelial surfaces, such as respiratory (e.g., airway, nasopharyngeal and laryngeal paths, tracheal, pulmonary, bronchi, bronchioles, alveoli, etc.) or gastrointestinal (e.g., buccal, esophageal, gastric, intestinal, rectal, anal, etc.) tracts, or other epithelial surfaces.

Particularly problematic are infections composed of bacterial biofilms, a relatively recently recognized organization of bacteria by which free, single-celled ("planktonic") bacteria assemble by intercellular adhesion into organized, multicellular communities (biofilms) having markedly different patterns of behavior, gene expression, and susceptibility to environmental agents including antibiotics. Biofilms may deploy biological defense mechanisms not found in planktonic bacteria, which mechanisms can protect the biofilm community against antibiotics and host immune responses. Established biofilms can arrest the tissue-healing process.

Common microbiologic contaminants that underlie persistent and potentially deleterious infections include *S. aureus*, including MRSA (Methicillin Resistant *Staphylococcus aureus*), *Enterococci, E. coli, P. aeruginosa, Streptococci*, and *Acinetobacter baumannii*. Some of these organisms exhibit an ability to survive on non-nutritive clinical surfaces for months. *S. aureus*, has been shown to be viable for four weeks on dry glass, and for between three and six months on dried blood and cotton fibers (Domenico et al., 1999 *Infect. Immun.* 67:664-669). Both *E. coli* and *P. aeruginosa* have been shown to survive even longer than *S. aureus* on dried blood and cotton fibers (ibid).

Microbial biofilms are associated with substantially increased resistance to both disinfectants and antibiotics. Biofilm morphology results when bacteria and/or fungi attach to surfaces. This attachment triggers an altered transcription of genes, resulting in the secretion of a remarkably resilient and difficult to penetrate polysaccharide matrix, protecting the microbes. Biofilms are very resistant to the mammalian immune system, in addition to their very substantial resistance to antibiotics. Biofilms are very difficult to eradicate once they become established, so preventing biofilm formation is a very important clinical priority. Recent research has shown that open wounds can quickly become contaminated by biofilms. These microbial biofilms are thought to delay wound healing, and are very likely related to the establishment of serious wound infections.

The current guidelines for the care for military wounds, for example, specify vigorous and complete irrigation and debridement (Blankenship CL, Guidelines for care of open combat casualty wounds, Fleet Operations and Support. U.S. Bureau of Medicine and Surgery). While this early intervention is important, it is not adequate to prevent the development of infection. Additional therapeutic steps need to be taken following debridement to promote healing, reduce the microbial bio-burden, and thereby reduce the chances of establishing wound infections and wound biofilms.

Because of the complex nature of military traumatic wounds, the potential for infection is great, particularly considering the introduction of foreign objects and other environmental contaminating agents. Both military and clinical environments (including people within both of these environments) act as important sources of potentially pathogenic microbes, particularly to those suffering from open and/or complex wounds. Acute and chronic wounds, including surgical and military wounds, have already compromised the body's primary defense and barrier against infection; the skin. Wounds thus expose the interior of the body (a moist and nutritive environment) to opportunistic and pathogenic infections. Many of these infections, particularly persistent wound infections, are likely related to biofilm formation, as has been shown to be the case with chronic wounds (James et al., 2008). Infection of wounds in hospitals constitutes one of the most common causes of nosocomial infection, and wounds acquired in military and natural disaster environments are particularly susceptible to microbial contamination. Military wounds are predisposed to infection because they are typically associated with tissue damage, tend to be extensive and deep, may introduce foreign bodies and interfere with local blood supply, may be associated with fractures and burns, and may lead to shock and compromised immune defenses.

Skin Architecture and Wound Healing

Maintenance of intact, functioning skin and other epithelial tissues (e.g., generally avascular epithelial surfaces that form barriers between an organism and its external environment, such as those found in skin and also found in the linings of respiratory and gastrointestinal tracts, glandular tissues, etc.) is significant to the health and survival of humans and other animals. The skin is the largest body organ in humans and other higher vertebrates (e.g., mammals), protecting against environmental insults through its barrier function, mechanical strength and imperviousness to water. As a significant environmental interface, skin provides a protective body covering that permits maintenance of physiological equilibria.

Skin architecture is well known. Briefly, epidermis, the skin outer layer, is covered by the stratum corneum, a protective layer of dead epidermal skin cells (e.g., keratinocytes) and extracellular connective tissue proteins. The epidermis undergoes a continual process of being sloughed off as it is replaced by new material pushed up from the underlying epidermal granular cell, spinous cell, and basal cell layers, where continuous cell division and protein synthesis produce new skin cells and skin proteins (e.g., keratin, collagen). The dermis lies underneath the epidermis, and is a site for the elaboration by dermal fibroblasts of connective tissue proteins (e.g., collagen, elastin, etc.) that assemble into extracellular matrix and fibrous structures that confer flexibility, strength and elasticity to the skin. Also present in the dermis are nerves, blood vessels, smooth muscle cells, hair follicles and sebaceous glands.

As the body's first line of defense, the skin is a major target for clinical insults such as physical, mechanical, chemical and biological (e.g., xenobiotic, autoimmune) attack that can alter its structure and function. The skin is also regarded as an important component of immunological defense of the organism. In the skin can be found migrating as well as resident white blood cells (e.g., lymphocytes, macrophages, mast cells) and epidermal dendritic (Langerhans) cells having potent antigen-presenting activity, which contribute to immunological protection. Pigmented melanocytes in the basal layer absorb potentially harmful ultraviolet (UV) radiation. Disruption of the skin presents undesirable risks to a subject, including those associated with opportunistic infections, incomplete or inappropriate tissue remodeling, scarring, impaired mobility, pain and/or other complications. Like the skin, other epithelial surfaces (e.g., respiratory tract, gastrointestinal tract and glandular linings) have defined structural attributes when healthy such that infection or other disruptions may present serious health risks.

Damaged or broken skin may result, for example, from wounds such as cuts, scrapes, abrasions, punctures, burns (including chemical burns), infections, temperature extremes, incisions (e.g., surgical incisions), trauma and other injuries. Efficient skin repair via wound healing is therefore clearly desirable in these and similar contexts.

Although skin naturally exhibits remarkable ability for self-repair following many types of damage, there remain a number of contexts in which skin healing does not occur rapidly enough and/or in which inappropriate cellular tissue repair mechanisms result in incompletely remodeled skin that as a consequence can lack the integrity, barrier properties, mechanical strength, elasticity, flexibility, or other desirable properties of undamaged skin. Skin wound healing thus presents such associated challenges, for example, in the context of chronic wounds.

Wound healing occurs in three dynamic and overlapping phases, beginning with the formation of a fibrin clot. The clot provides a temporary shield and a reservoir of growth factors that attracts cells into the wound. It also serves as a provisional extracellular matrix (ECM) that the cells invade during repair. Intermingled with clot formation is the inflammatory phase, which is characterized by the infiltration of phagocytes and neutrophils into the wound, which clear the wound of debris and bacteria, while releasing growth factors that amplify the early healing response. The process of restoring the denuded area is initiated in the proliferation phase of healing and is driven by chemokines, cytokines, and proteases that have been secreted from the immune cells and are concentrated within the clot. Keratinocytes are stimulated to proliferate and migrate, which forms the new layer of epithelium that covers the wound while wound angiogenesis delivers oxygen, nutrients, and inflammatory cells to the wounded area. The remodeling phase is the final phase of wound repair and it is carried out by the myofibroblasts, which facilitate connective tissue contraction, increase wound strength, and deposit the ECM that forms the scar (Martin, P. Wound Healing-Aiming for Perfect Skin Regeneration. *Science* 1997; 4:75-80).

Bismuth Thiol-(BT) Based Antiseptics

A number of natural products (e.g., antibiotics) and synthetic chemicals having antimicrobial, and in particular antibacterial, properties are known in the art and have been at least partially characterized by chemical structures and by antimicrobial effects, such as ability to kill microbes ("cidal" effects such as bacteriocidal properties), ability to halt or impair microbial growth ("static" effects such as bacteriostatic properties), or ability to interfere with microbial functions such as colonizing or infecting a site, bacterial secretion of exopolysaccharides and/or conversion from planktonic to biofilm populations or expansion of biofilm formation. Antibiotics, disinfectants, antiseptics and the like (including bismuth-thiol or BT compounds) are discussed, for example, in U.S. Pat. No. 6,582,719, including factors that influence the selection and use of such compositions, including, e.g., bacteriocidal or bacteriostatic potencies, effective concentrations, and risks of toxicity to host tissues.

Bismuth, a group V metal, is an element that (like silver) possesses antimicrobial properties. Bismuth by itself may not be therapeutically useful and may exhibit certain inappropriate properties, and so may instead be typically administered by means of delivery with a complexing agent, carrier, and/or other vehicle, the most common example of which is, the treatment preparation for gastro-intestinal disorders sold under the trademark PEPTO-BISMOL® (Procter & Gamble), in which bismuth is combined (chelated) with sub-salicylate. Previous research has determined that the combination of certain thiol-(-SH, sulfhydryl) containing compounds such as ethane dithiol with bismuth, to provide an exemplary bismuth thiol (BT) compound, improves the antimicrobial potency of bismuth, compared to other bismuth preparations currently available. There are many thiol compounds that may be used to produce BTs (disclosed, for example, in Domenico et al., 2001 *Antimicrob. Agent. Chemotherap.* 45(5):1417-1421, Domenico et al., 1997 *Antimicrob. Agent. Chemother.* 41(8):1697-1703, and in U.S. Pat. No. RE37,793, U.S. Pat. No. 6,248,371, U.S. Pat. No. 6,086, 921, and U.S. Pat. No. 6,380,248; see also, e.g., U.S. Pat. No. 6,582,719) and several of these preparations are able to inhibit biofilm formation.

BT compounds have proven activity against MRSA (methicillin resistant *S. aureus*), MRSE (methicillin resistant *S. epidermidis*), *Mycobacterium tuberculosis*, *Mycobacterium avium*, drug-resistant *P. aeruginosa*, enterotoxigenic *E. coli*, enterohemorrhagic *E. coli*, *Klebsiella pneumoniae*, *Clostridium difficile*, *Heliobacter pylori*, *Legionella pneumophila*, *Enterococcus faecalis*, *Enterobacter cloacae*, *Salmonella typhimurium*, *Proteus vulgaris*, *Yersinia enterocolitica*, *Vibrio cholerae*, and *Shigella Flexneri* (Domenico et al., 1997

*Antimicrob. Agents Chemother.* 41:1697-1703). There is also evidence of activity against cytomegalovirus, herpes simplex virus type 1 (HSV-1) and HSV-2, and yeasts and fungi, such as *Candida albicans*. BT roles have also been demonstrated in reducing bacterial pathogenicity, inhibiting or killing a broad spectrum of antibiotic-resistant microbes (gram-positive and gram-negative), preventing biofilm formation, preventing septic shock, treating sepsis, and increasing bacterial susceptibility to antibiotics to which they previously exhibited resistance (see, e.g., Domenico et al., 2001 *Agents Chemother.* 45:1417-1421; Domenico et al., 2000 *Infect. Med.* 17:123-127; Domenico et al., 2003 *Res. Adv. In Antimicrob. Agents & Chemother.* 3:79-85; Domenico et al., 1997 *Antimicrob. Agents Chemother.* 41(8):1697-1703; Domenico et al., 1999 *Infect. Immun.* 67:664-669: Huang et al. 1999 *J Antimicrob. Chemother.* 44:601-605; Veloira et al., 2003 *J Antimicrob. Chemother.* 52:915-919; Wu et al., 2002 *Am J Respir Cell Mol. Biol.* 26:731-738).

Despite the availability of BT compounds for well over a decade, effective selection of appropriate BT compounds for particular infectious disease indications has remained an elusive goal, where behavior of a particular BT against a particular microorganism cannot be predicted, where synergistic activity of a particular BT and a particular antibiotic against a particular microorganism cannot be predicted, where BT effects in vitro may not always predict BT effects in vivo, and where BT effects against planktonic (single-cell) microbial populations may not be predictive of BT effects against microbial communities, such as bacteria organized into a biofilm. Additionally, limitations in solubility, tissue permeability, bioavailability, biodistribution and the like may in the cases of some BT compounds hinder the ability to deliver clinical benefit safely and effectively. The presently disclosed invention embodiments address these needs and offer other related advantages.

BRIEF SUMMARY

As disclosed herein, and without wishing to be bound by theory, according to certain embodiments described herein bismuth-thiol (BT) compounds may be used as antiseptic agents for use in the treatment of a wide variety of clinical infectious diseases and conditions and in personal healthcare, while also decreasing the costs incurred for the treatment of such infections, including savings that are realized by prevention or prophylaxis mediated at least in part by BTs.

Also, in certain embodiments there are contemplated formulations for treating tissues and/or surfaces that contain bacterial biofilms or bacteria related to biofilm formation (e.g., bacteria that are capable of forming or otherwise promoting biofilms), which formulations comprise one or more BT compound and one or more antibiotic compound, as described herein, where according to non-limiting theory, appropriately selected combinations of BT compound(s) and antibiotic(s) based on the present disclosure provide heretofore unpredicted synergy in the antibacterial (including antibiofilm) effects of such formulations, and/or unpredicted enhancing effects, for prevention, prophylaxis and/or therapeutically effective treatment against microbial infections including infections that contain bacterial biofilms.

Also provided herein are bismuth-thiol compositions comprising substantially monodisperse microparticulate suspensions, and methods for their synthesis and use.

According to certain embodiments there is provided a method for protecting a natural surface against one or more of a bacterial pathogen, a fungal pathogen and a viral pathogen, comprising contacting the surface with an effective amount of a BT composition under conditions and for a time sufficient for one or more of: (i) prevention of infection of the surface by the bacterial, fungal or viral pathogen, (ii) inhibition of cell viability or cell growth of substantially all planktonic cells of the bacterial, fungal or viral pathogen, (iii) inhibition of biofilm formation by the bacterial, fungal or viral pathogen, and (iv) inhibition of biofilm viability or biofilm growth of substantially all biofilm-form cells of the bacterial, fungal or viral pathogen, wherein the BT composition comprises a plurality of solid microparticles that exhibit a unimodal size distribution when the BT composition is analyzed on a particle size analyzer and that comprise a bismuth-thiol (BT) compound that has not been micronized, milled or subjected to supercritical fluid processing, substantially all of said microparticles having a volumetric mean diameter of from about 0.4 μm to about 5 μm, wherein the BT compound comprises bismuth or a bismuth salt and a thiol-containing compound.

In certain further embodiments the bacterial pathogen comprises at least one of: (i) one or more gram-negative bacteria; (ii) one or more gram-positive bacteria; (iii) one or more antibiotic-sensitive bacteria; (iv) one or more antibiotic-resistant bacteria; (v) a bacterial pathogen that is selected from the group consisting of *Staphylococcus aureus* (*S. aureus*), MRSA (methicillin-resistant *S. aureus*), *Staphylococcus epidermidis*, MRSE (methicillin-resistant *S. epidermidis*), *Mycobacterium tuberculosis*, *Mycobacterium avium*, *Pseudomonas aeruginosa*, drug-resistant *P. aeruginosa*, *Escherichia coli*, enterotoxigenic *E. coli*, enterohemorrhagic *E. coli*, *Klebsiella pneumoniae*, *Clostridium difficile*, *Heliobacter pylori*, *Legionella pneumophila*, *Enterococcus faecalis*, methicillin-susceptible *Enterococcus faecalis*, *Enterobacter cloacae*, *Salmonella typhimurium*, *Proteus vulgaris*, *Yersinia enterocolitica*, *Vibrio cholera*, *Shigella flexneri*, vancomycin-resistant *Enterococcus* (VRE), *Burkholderia cepacia* complex, *Francisella tularensis*, *Bacillus anthracis*, *Yersinia pestis*, *Pseudomonas aeruginosa*, *Streptococcus pneumonia*, penicillin-resistant *Streptococcus pneumonia*, *Escherichia coli*, *Burkholderia cepacia*, *Bukholderia multivorans*, *Mycobacterium smegmatis* and *Acinetobacter baumannii*.

In certain other further embodiments at least one of (a) the bacterial pathogen exhibits resistance to an antibiotic that is selected from methicillin, vancomycin, naficilin, gentamicin, ampicillin, chloramphenicol, doxycycline and tobramycin, (b) the surface comprises an epithelial tissue surface that is selected from epidermis, dermis, respiratory tract, gastrointestinal tract and glandular linings, (c) the step of contacting is performed one or a plurality of times, (d) at least one step of contacting comprises one of spraying, irrigating, dipping and painting the surface, (e) at least one step of contacting comprises one of inhaling, ingesting and orally irrigating, (f) at least one step of contacting comprises administering to a subject by a route that is selected from topically, intraperitoneally, orally, parenterally, intravenously, intraarterially, transdermally, sublingually, subcutaneously, intramuscularly, transbuccally, intranasally, via inhalation, intraoccularly, intraauricularly, intraventricularly, subcutaneously, intraadiposally, intraarticularly and intrathecally, and (g) the BT composition comprises one or more BT compounds selected from BisBAL, BisEDT, Bis-dimercaprol, Bis-DTT, Bis-2-mercaptoethanol, Bis-DTE, Bis-Pyr, Bis-Ery, Bis-Tol, Bis-BDT, Bis-PDT, Bis-Pyr/Bal, Bis-Pyr/BDT, Bis-Pyr/EDT, Bis-Pyr/PDT, Bis-Pyr/Tol, Bis-Pyr/Ery, bismuth-1-mercapto-2-propanol, and Bis-EDT/2-hydroxy-1-propanethiol.

In another embodiment there is provided a method for protecting a natural surface against one or more of a bacterial pathogen, a fungal pathogen and a viral pathogen, comprising contacting the surface with an effective amount of a BT composition under conditions and for a time sufficient for one or more of (i) prevention of infection of the surface by the bacterial, fungal or viral pathogen, (ii) inhibition of cell viability or cell growth of substantially all planktonic cells of the bacterial, fungal or viral pathogen, (iii) inhibition of biofilm formation by the bacterial, fungal or viral pathogen, and (iv) inhibition of biofilm viability or biofilm growth of substantially all biofilm-form cells of the bacterial, fungal or viral pathogen, wherein the BT composition comprises a plurality of solid microparticles that exhibit a unimodal size distribution when the BT composition is analyzed on a particle size analyzer and that comprise a bismuth-thiol (BT) compound which comprises bismuth or a bismuth salt and a thiol-containing compound, substantially all of said microparticles having a volumetric mean diameter of from about 0.4 µm to about 5 µm, wherein the BT compound, wherein at least one of (a) the bacterial pathogen exhibits resistance to an antibiotic that is selected from methicillin, vancomycin, naficilin, gentamicin, ampicillin, chloramphenicol, doxycycline and tobramycin, (b) the surface comprises an epithelial tissue surface that is selected from epidermis, dermis, respiratory tract, gastrointestinal tract and glandular linings, (c) the step of contacting is performed one or a plurality of times, (d) at least one step of contacting comprises one of spraying, irrigating, dipping and painting the surface, (e) at least one step of contacting comprises one of inhaling, ingesting and orally irrigating, (f) at least one step of contacting comprises administering to a subject by a route that is selected from topically, intraperitoneally, orally, parenterally, intravenously, intraarterially, transdermally, sublingually, subcutaneously, intramuscularly, transbuccally, intranasally, via inhalation, intraoccularly, intraauricularly, intraventricularly, subcutaneously, intraadiposally, intraarticularly and intrathecally, and (g) the BT composition comprises one or more BT compounds selected from the group consisting of BisBAL, BisEDT, Bis-dimercaprol, Bis-DTT, Bis-2-mercaptoethanol, Bis-DTE, Bis-Pyr, Bis-Ery, Bis-Tol, Bis-BDT, Bis-PDT, Bis-Pyr/Bal, Bis-Pyr/BDT, Bis-Pyr/EDT, Bis-Pyr/PDT, Bis-Pyr/Tol, Bis-Pyr/Ery, bismuth-1-mercapto-2-propanol, and Bis-EDT/2-hydroxy-1-propanethiol, and wherein the method further comprises contacting the surface with at least one of (i) a synergizing antibiotic and (ii) a cooperative antimicrobial efficacy enhancing antibiotic, simultaneously or sequentially and in any order with respect to the step of contacting the surface with the BT composition.

In certain further embodiments at least one of (a) the synergizing antibiotic or the cooperative antimicrobial efficacy enhancing antibiotic comprises an antibiotic that is selected from an aminoglycoside antibiotic, a carbapenem antibiotic, a cephalosporin antibiotic, a fluoroquinolone antibiotic, a glycopeptide antibiotic, a lincosamide antibiotic, a penicillinase-resistant penicillin antibiotic, and an aminopenicillin antibiotic, and (b) the synergizing antibiotic or the cooperative antimicrobial efficacy enhancing antibiotic is an aminoglycoside antibiotic that is selected from amikacin, arbekacin, gentamicin, kanamycin, neomycin, netilmicin, paromomycin, rhodostreptomycin, streptomycin, tobramycin and apramycin. In certain other embodiments the method comprises overcoming antibiotic resistance where an antibiotic-resistant bacterial pathogen is present on the natural surface. In certain further embodiments at least one of (a) the bacterial pathogen is selected from *Staphylococcus aureus* (*S. aureus*), MRSA (methicillin-resistant *S. aureus*), *Staphylococcus epidermidis*, MRSE (methicillin-resistant *S. epidermidis*), *Mycobacterium tuberculosis*, *Mycobacterium avium*, *Pseudomonas aeruginosa*, drug-resistant *P. aeruginosa*, *Escherichia coli*, enterotoxigenic *E. coli*, enterohemorrhagic *E. coli*, *Klebsiella pneumoniae*, *Clostridium difficile*, *Heliobacter pylori*, *Legionella pneumophila*, *Enterococcus faecalis*, methicillin-susceptible *Enterococcus faecalis*, *Enterobacter cloacae*, *Salmonella typhimurium*, *Proteus vulgaris*, *Yersinia enterocolitica*, *Vibrio cholera*, *Shigella flexneri*, vancomycin-resistant *Enterococcus* (VRE), *Burkholderia cepacia* complex, *Francisella tularensis*, *Bacillus anthracis*, *Yersinia pestis*, *Pseudomonas aeruginosa*, *Streptococcus pneumonia*, penicillin-resistant *Streptococcus pneumonia*, *Escherichia coli*, *Burkholderia cepacia*, *Bukholderia multivorans*, *Mycobacterium smegmatis* and *Acinetobacter baumannii*, (b) the bacterial pathogen exhibits resistance to an antibiotic that is selected from methicillin, vancomycin, naficilin, gentamicin, ampicillin, chloramphenicol, doxycycline, tobramycin, clindamicin and gatifloxacin, (c) the surface comprises an epithelial surface of a tissue that is selected from the group consisting of epidermis, dermis, respiratory tract, gastrointestinal tract and glandular linings, (d) the step of contacting is performed one or a plurality of times, (e) at least one step of contacting comprises one of spraying, irrigating, dipping, coating and painting the surface, (f) at least one step of contacting comprises one of inhaling, ingesting and orally irrigating, (g) at least one step of contacting comprises administering to a subject by a route that is selected from topically, intraperitoneally, orally, parenterally, intravenously, intraarterially, transdermally, sublingually, subcutaneously, intramuscularly, transbuccally, intranasally, via inhalation, intraoccularly, intraauricularly, intraventricularly, subcutaneously, intraadiposally, intraarticularly and intrathecally, (h) the BT composition comprises one or more BT compounds selected from BisBAL, BisEDT, Bis-dimercaprol, Bis-DTT, Bis-2-mercaptoethanol, Bis-DTE, Bis-Pyr, Bis-Ery, Bis-Tol, Bis-BDT, Bis-PDT, Bis-Pyr/Bal, Bis-Pyr/BDT, Bis-Pyr/EDT, Bis-Pyr/PDT, Bis-Pyr/Tol, Bis-Pyr/Ery, bismuth-1-mercapto-2-propanol, and Bis-EDT/2-hydroxy-1-propanethiol, (i) the synergizing or enhancing antibiotic comprises an antibiotic that is selected from clindamicin, gatifloxacin, an aminoglycoside antibiotic, a carbapenem antibiotic, a cephalosporin antibiotic, a fluoroquinolone antibiotic, a penicillinase-resistant penicillin antibiotic, and an aminopenicillin antibiotic, and (j) the synergizing or enhancing antibiotic is an aminoglycoside antibiotic that is selected from amikacin, arbekacin, gentamicin, kanamycin, neomycin, netilmicin, paromomycin, rhodostreptomycin, streptomycin, tobramycin and apramycin.

In another embodiment of the present invention there is provided an antiseptic composition for treating a natural surface that contains bacterial biofilm, comprising at least one of (1) a composition that comprises (a) at least one BT composition that comprises a plurality of solid microparticles that exhibit a unimodal size distribution when the composition is analyzed on a particle size analyzer and that comprise a bismuth-thiol (BT) compound which comprises bismuth or a bismuth salt and a thiol-containing compound, substantially all of said microparticles having a volumetric mean diameter of from about 0.4 µm to about 5 µm; and (b) at least one antibiotic compound that is capable of acting synergistically with, or enhancing, the BT compound, (2) a composition that comprises (a) at least one BT composition that comprises a plurality of solid microparticles that exhibit a unimodal size distribution when the composition is analyzed on a particle size analyzer and that comprise a bismuth-thiol (BT) compound which comprises bismuth or a bismuth salt and a thiol-containing compound, substantially all of said microparticles having a volumetric mean diameter of from about 0.4 µm to about 5 µm; and (b) at least one antibiotic compound that is capable of acting synergistically with, or enhancing, the BT compound, wherein the antibiotic compound comprises an antibiotic that is selected from methicillin, vancomycin, naficilin, gentamicin, ampicillin, chloramphenicol, doxycycline, tobramycin, clindamicin, gatifloxacin, cefazolin and an aminoglycoside antibiotic, and (3) the composition of (2) wherein the aminoglycoside antibiotic is selected from amikacin, arbekacin, gentamicin, kanamycin, neomycin, netilmicin, paromomycin, rhodostreptomycin, streptomycin, tobramycin and apramycin. In certain further embodiments the BT compound is selected from BisBAL, BisEDT, Bis-dimercaprol, Bis-DTT, Bis-2-mercaptoethanol, Bis-DTE, Bis-Pyr, Bis-Ery, Bis-Tol, Bis-BDT, Bis-PDT, Bis-Pyr/Bal, Bis-Pyr/BDT, Bis-Pyr/EDT, Bis-Pyr/PDT, Bis-Pyr/Tol, Bis-Pyr/Ery, bismuth-1-mercapto-2-propanol, and Bis-EDT/2-hydroxy-1-propanethiol.

According to certain other embodiments there is provided a method for treating a natural surface that contains bacterial biofilm, comprising (a) identifying a bacterial infection in or on the surface as comprising one of (i) gram positive bacteria, (ii) gram negative bacteria, and (iii) both (i) and (ii); and (b) administering a formulation that comprises one or more bismuth thiol (BT) compositions to the surface, wherein (i) if the bacterial infection comprises gram positive bacteria, then the formulation comprises effective amounts of at least one BT compound and at least one antibiotic that is rifamycin, (ii) if the bacterial infection comprises gram negative bacteria, then the formulation comprises effective amounts of at least one BT compound and amikacin, (iii) if the bacterial infection comprises both gram positive and gram negative bacteria, then the formulation comprises effective amounts of one or a plurality of BT compounds, rifamycin and amikacin, and thereby treating the surface, wherein the BT compound comprises bismuth or a bismuth salt and a thiol-containing compound. In certain further embodiments the bacterial infection comprises one or a plurality of antibiotic-resistant bacteria. In certain further embodiments treating comprises at least one of: (i) eradicating the bacterial biofilm, (ii) reducing the bacterial biofilm, and (iii) impairing growth of the bacterial biofilm.

In certain other related embodiments the BT composition comprises a plurality of solid microparticles that exhibit a unimodal size distribution when the composition is analyzed on a particle size analyzer and that comprise a bismuth-thiol (BT) compound, substantially all of said microparticles having a volumetric mean diameter of from about 0.4 μm to about 5 μm, wherein the BT compound comprises bismuth or a bismuth salt and a thiol-containing compound. In certain embodiments the BT compound has not been micronized, milled or subjected to super-critical fluid processing.

According to certain embodiments of the invention described herein there is thus provided a bismuth-thiol composition, comprising a plurality of microparticles that comprise a bismuth-thiol (BT) compound, substantially all of said microparticles having a volumetric mean diameter of from about 0.4 μm to about 5 μm, wherein the BT compound comprises bismuth or a bismuth salt and a thiol-containing compound. In another embodiment there is provided a bismuth-thiol composition, comprising a plurality of microparticles that comprise a bismuth-thiol (BT) compound, substantially all of said microparticles having a volumetric mean diameter of from about 0.4 μm to about 5 μm and being formed by a process that comprises (a) admixing, under conditions and for a time sufficient to obtain a solution that is substantially free of a solid precipitate, (i) an acidic aqueous solution that comprises a bismuth salt comprising bismuth at a concentration of at least 50 mM and that lacks a hydrophilic, polar or organic solubilizer, with (ii) ethanol in an amount sufficient to obtain an admixture that comprises at least about 5%, 10%, 15%, 20%, 25% or 30% ethanol by volume; and (b) adding to the admixture of (a) an ethanolic solution comprising a thiol-containing compound to obtain a reaction solution, wherein the thiol-containing compound is present in the reaction solution at a molar ratio of from about 1:3 to about 3:1 relative to the bismuth, under conditions and for a time sufficient for formation of a precipitate which comprises the microparticles comprising the BT compound. In certain embodiments the bismuth salt is $Bi(NO_3)_3$. In certain embodiments the acidic aqueous solution comprises at least 5%, 10%, 15%, 20%, 22% or 22.5% bismuth by weight. In certain embodiments the acidic aqueous solution comprises at least 0.5%, 1%, 1.5%, 2%, 2.5%, 3%, 3.5%, 4%, 4.5% or 5% nitric acid by weight. In certain embodiments the thiol-containing compound comprises one or more agents selected from 1,2-ethane dithiol, 2,3-dimercaptopropanol, pyrithione, dithioerythritol, 3,4-dimercaptotoluene, 2,3-butanedithiol, 1,3-propanedithiol, 2-hydroxypropane thiol, 1-mercapto-2-propanol, dithioerythritol, alpha-lipoic acid and dithiothreitol.

In another embodiment there is provided a method for preparing a bismuth-thiol composition that comprises a plurality of microparticles that comprise a bismuth-thiol (BT) compound, substantially all of said microparticles having a volumetric mean diameter of from about 0.4 μm to about 5 μm, said method comprising the steps of (a) admixing, under conditions and for a time sufficient to obtain a solution that is substantially free of a solid precipitate, (i) an acidic aqueous solution that comprises a bismuth salt comprising bismuth at a concentration of at least 50 mM and that lacks a hydrophilic, polar or organic solubilizer, with (ii) ethanol in an amount sufficient to obtain an admixture that comprises at least about 5%, 10%, 15%, 20%, 25% or 30% ethanol by volume; and (b) adding to the admixture of (a) an ethanolic solution comprising a thiol-containing compound to obtain a reaction solution, wherein the thiol-containing compound is present in the reaction solution at a molar ratio of from about 1:3 to about 3:1 relative to the bismuth, under conditions and for a time sufficient for formation of a precipitate which comprises the microparticles comprising the BT compound. In certain embodiments the method further comprises recovering the precipitate to remove impurities. In certain embodiments the bismuth salt is $Bi(NO_3)_3$. In certain embodiments the acidic aqueous solution comprises at least 5%, 10%, 15%, 20%, 22% or 22.5% bismuth by weight. In certain embodiments the acidic aqueous solution comprises at least 0.5%, 1%, 1.5%, 2%, 2.5%, 3%, 3.5%, 4%, 4.5% or 5% nitric acid by weight. In certain embodiments the thiol-containing compound comprises one or more agents selected from the group consisting of 1,2-ethane dithiol, 2,3-dimercaptopropanol, pyrithione, dithioerythritol, 3,4-dimercaptotoluene, 2,3-butanedithiol, 1,3-propanedithiol, 2-hydroxypropane thiol, 1-mercapto-2-propanol, dithioerythritol, dithiothreitol, alpha-lipoic acid, methanethiol ($CH_3SH$ [m-mercaptan]), ethanethiol ($C_2H_5SH$ [e-mercaptan]), 1-propanethiol ($C_3H_7SH$ [n-P mercaptan]), 2-propanethiol ($CH_3CH(SH)CH_3$ [2$C_3$ mercaptan]), butanethiol ($C_4H_9SH$ ([n-butyl mercaptan]), tert-butyl mercaptan ($C(CH_3)_3SH$ [t-butyl mercaptan]), pentanethiols ($C_5H_{11}SH$ [pentyl mercaptan]), coenzyme A, lipoamide, glutathione, cysteine, cystine, 2-mercaptoethanol, dithiothreitol, dithioerythritol, 2-mercaptoindole, transglutaminase, (11-mercaptoundecyl)hexa(ethylene glycol), (11-mercaptoundecyl)tetra (ethylene glycol), (11-mercaptoundecyl)tetra(ethylene glycol) functionalized gold nanoparticles, 1,1',4',1"-terphenyl-4-thiol, 1,11-undecanedithiol, 1,16-hexadecanedithiol, 1,2-ethanedithiol technical grade, 1,3-propanedithiol, 1,4-benzenedimethanethiol, 1,4-butanedithiol, 1,4-butanedithiol diacetate, 1,5-pentanedithiol, 1,6-hexanedithiol, 1,8-octanedithiol, 1,9-nonanedithiol, adamantanethiol, 1-butanethiol, 1-decanethiol, 1-dodecanethiol, 1-heptanethiol, 1-heptanethiol purum, 1-hexadecanethiol, 1-hexanethiol, 1-mercapto-(triethylene glycol), 1-mercapto-(triethylene glycol) methyl ether functionalized gold nanoparticles, 1-mercapto-2-propanol, 1-nonanethiol, 1-octadecanethiol, 1-octanethiol, 1-octanethiol, 1-pentadecanethiol, 1-pentanethiol, 1-propanethiol, 1-tetradecanethiol, 1-tetradecanethiol purum, 1-undecanethiol, 11-(1H-pyrrol-1-yl)undecane-1-thiol, 11-amino-1-undecanethiol hydrochloride, 11-bromo-1-undecanethiol, 11-mercapto-1-undecanol, 11-mercapto-1-undecanol, 11-mercaptoundecanoic acid, 11-mercaptoundecanoic acid, 11-mercaptoundecyl trifluoroacetate, 11-mercaptoundecylphosphoric acid, 12-mercaptododecanoic acid, 12-mercaptododecanoic acid, 15-mercaptopentadecanoic acid, 16-mercaptohexadecanoic acid, 16-mercaptohexadecanoic acid, 1H,1H,2H,2H-perfluorodecanethiol, 2,2'-(ethylenedioxy)diethanethiol, 2,3-butanedithiol, 2-butanethiol, 2-ethylhexanethiol, 2-methyl-1-propanethiol, 2-methyl-2-propanethiol, 2-phenylethanethiol, 3,3,4,4,5,5,6,6-nonafluoro-1-hexanethiolpurum, 3-(dimethoxymethylsilyl)-1-propanethiol, 3-chloro-1-propanethiol, 3-mercapto-1-propanol, 3-mercapto-2-butanol, 3-mercapto-N-nonylpropionamide, 3-mercaptopropionic acid, 3-mercaptopropyl-functionalized silica gel, 3-methyl-1-butanethiol, 4,4'-bis(mercaptomethyl)biphenyl, 4,4'-dimercaptostilbene, 4-(6-mercaptohexyloxyl)benzyl alcohol, 4-cyano-1-butanethiol, 4-mercapto-1-butanol, 6-(ferrocenyl)hexanethiol, 6-mercapto-1-hexanol, 6-mercaptohexanoic acid, 8-mercapto-1-octanol, 8-mercaptooctanoic acid, 9-mercapto-1-nonanol, biphenyl-4,4'-dithiol, butyl 3-mercaptopropionate, copper(I) 1-butanethiolate, cyclohexanethiol, cyclopentanethiol, decanethiol functionalized silver nanoparticles, dodecanethiol functionalized gold nanoparticles, dodecanethiol functionalized silver nanoparticles, hexa(ethylene glycol)mono-11-(acetylthio)undecyl ether, mercaptosuccinic acid, methyl 3-mercaptopropionate, heptanoic hydrazide bisphenol A substituted 5-(Hydroxymethyl)-1:3-bis(6-mercaptohexyloxy)benzene sold under the trademark NANO TETHER BPA-HH™ (Sigma-Aldrich, St. Louis, Mo.), octadecanethiol reagents sold under the trademark NANOTHINKS™ 18 (Sigma-Aldrich) octanethiol reagents sold under the trademark NANOTHINKS™ 8 (Sigma-Aldrich), 11-mercaptoundecanoic acid reagents sold under the trademark NANOTHINKS™ ACID11 (Sigma-Aldrich), 16-mercaptorhexadecanoic acid reagents sold under the trademark NANOTHINKS™ ACID16 (Sigma-Aldrich), 11-mercapto-1-undecanol reagents sold under the trademark NANOTHINKS™ ALCO11 (Sigma-Aldrich), 1,8-octanedithiol sold under the trademark NANOTHINKS™ THIO8 (Sigma-Aldrich), octanethiol functionalized gold nanoparticles, PEG dithiol average $M_n$ 8,000, PEG dithiol average mol wt 1,500, PEG dithiol average mol wt 3,400, S-(11-bromoundecyl)thioacetate, S-(4-cyanobutyl)thioacetate, thiophenol, triethylene glycol mono-11-mercaptoundecyl ether, trimethylolpropane tris(3-mercaptopropionate), [11-(methylcarbonylthio)undecyl]tetra(ethylene glycol), m-carborane-9-thiol, p-terphenyl-4,4"-dithiol, tert-dodecylmercaptan, tert-nonyl mercaptan.

In another embodiment there is provided a method for protecting a natural surface, including a biological tissue surface such as an epithelial tissue surface, against one or more of a bacterial pathogen, a fungal pathogen and a viral pathogen, comprising contacting the epithelial tissue surface with an effective amount of a BT composition under conditions and for a time sufficient for one or more of (i) prevention of infection of the surface by the bacterial, fungal or viral pathogen, (ii) inhibition of cell viability or cell growth of substantially all planktonic cells of the bacterial, fungal or viral pathogen, (iii) inhibition of biofilm formation by the bacterial, fungal or viral pathogen, and (iv) inhibition of biofilm viability or biofilm growth of substantially all biofilm-form cells of the bacterial, fungal or viral pathogen, wherein the BT composition comprises a plurality of microparticles that comprise a bismuth-thiol (BT) compound, substantially all of said microparticles having a volumetric mean diameter of from about 0.4 µm to about 5 µm. In certain embodiments the bacterial pathogen comprises at least one of (i) one or more gram-negative bacteria; (ii) one or more gram-positive bacteria; (iii) one or more antibiotic-sensitive bacteria; (iv) one or more antibiotic-resistant bacteria; (v) a bacterial pathogen that is selected from *Staphylococcus aureus* (*S. aureus*), MRSA (methicillin-resistant *S. aureus*), *Staphylococcus epidermidis*, MRSE (methicillin-resistant *S. epidermidis*), *Mycobacterium tuberculosis*, *Mycobacterium avium*, *Pseudomonas aeruginosa*, drug-resistant *P. aeruginosa*, *Escherichia coli*, enterotoxigenic *E. coli*, enterohemorrhagic *E. coli*, *Klebsiella pneumoniae*, *Clostridium difficile*, *Heliobacter pylori*, *Legionella pneumophila*, *Enterococcus faecalis*, methicillin-susceptible *Enterococcus faecalis*, *Enterobacter cloacae*, *Salmonella typhimurium*, *Proteus vulgaris*, *Yersinia enterocolitica*, *Vibrio cholera*, *Shigella flexneri*, vancomycin-resistant *Enterococcus* (VRE), *Burkholderia cepacia* complex, *Francisella tularensis*, *Bacillus anthracis*, *Yersinia pestis*, *Pseudomonas aeruginosa*, vancomycin-resistant enterococci, *Streptococcus pneumonia*, penicillin-resistant *Streptococcus pneumonia*, *Escherichia coli*, *Burkholderia cepacia*, *Bukholderia multivorans*, *Mycobacterium smegmatis* and *Acinetobacter baumannii*. In certain embodiments the bacterial pathogen exhibits antibiotic resistance. In certain embodiments the bacterial pathogen exhibits resistance to an antibiotic that is selected from methicillin, vancomycin, naficilin, gentamicin, ampicillin, chloramphenicol, doxycycline and tobramycin.

In certain embodiments the natural surface comprises an oral/buccal cavity surface. In further embodiments, the natural surface comprises a biological surface such as bone, joint, muscle, ligament, or tendon.

In certain embodiments the surface comprises an epithelial tissue surface that comprises a tissue that is selected from epidermis, dermis, respiratory tract, gastrointestinal tract and glandular linings.

In certain embodiments the step of contacting is performed one or a plurality of times. In certain embodiments at least one step of contacting comprises one of spraying, irrigating, dipping and painting the natural surface. In certain embodiments at least one step of contacting comprises one of inhaling, ingesting and orally irrigating. In certain embodiments least one step of contacting comprises administering by a route that is selected from topically, intraperitoneally, orally, parenterally, intravenously, intraarterially, transdermally, sublingually, subcutaneously, intramuscularly, transbuccally, intranasally, via inhalation, intraoccularly, intraauricularly, intraventricularly, subcutaneously, intraadiposally, intraarticularly and intrathecally. In certain embodiments the BT composition comprises one or more BT compounds selected from the group consisting of BisBAL, BisEDT, Bis-dimercaprol, Bis-DTT, Bis-2-mercaptoethanol, Bis-DTE, Bis-Pyr, Bis-Ery, Bis-Tol, Bis-BDT, Bis-PDT, Bis-Pyr/Bal, Bis-Pyr/

BDT, Bis-Pyr/EDT, Bis-Pyr/PDT, Bis-Pyr/Tol, Bis-Pyr/Ery, bismuth-1-mercapto-2-propanol, and Bis-EDT/2-hydroxy-1-propanethiol.

In certain embodiments the bacterial pathogen exhibits antibiotic resistance. In certain other embodiments the above described method further comprises contacting the natural surface with a synergizing antibiotic and/or with an enhancing antibiotic, simultaneously or sequentially and in any order with respect to the step of contacting the surface with the BT composition. In certain embodiments the synergizing and/or enhancing antibiotic comprises an antibiotic that is selected from an aminoglycoside antibiotic, a carbapenem antibiotic, a cephalosporin antibiotic, a fluoroquinolone antibiotic, a glycopeptide antibiotic, a lincosamide antibiotic, a penicillinase-resistant penicillin antibiotic, and an aminopenicillin antibiotic. In certain embodiments the synergizing and/or enhancing antibiotic is an aminoglycoside antibiotic that is selected from amikacin, arbekacin, gentamicin, kanamycin, neomycin, netilmicin, paromomycin, rhodostreptomycin, streptomycin, tobramycin and apramycin.

In another embodiment of the invention described herein there is provided a method for overcoming antibiotic resistance (e.g., for a bacterial pathogen that is resistant to at least one anti-bacterial effect of at least one antibiotic known to have an anti-bacterial effect against bacteria of the same bacterial species, rendering such a pathogen susceptible to an antibiotic) on a natural surface where an antibiotic-resistant bacterial pathogen is present, comprising contacting the surface simultaneously or sequentially and in any order with an effective amount of (1) at least one bismuth-thiol (BT) composition and (2) at least one antibiotic that is enhanced by, and/or that is capable of acting synergistically with the at least one BT composition, under conditions and for a time sufficient for one or more of: (i) prevention of infection of the surface by the bacterial pathogen, (ii) inhibition of cell viability or cell growth of substantially all planktonic cells of the bacterial pathogen, (iii) inhibition of biofilm formation by the bacterial pathogen, and (iv) inhibition of biofilm viability or biofilm growth of substantially all biofilm-form cells of the bacterial pathogen, wherein the BT composition comprises a plurality of microparticles that comprise a bismuth-thiol (BT) compound, substantially all of said microparticles having a volumetric mean diameter of from about 0.4 μm to about 5 μm; and thereby overcoming antibiotic resistance on the epithelial tissue surface. In certain embodiments the bacterial pathogen comprises at least one of: (i) one or more gram-negative bacteria; (ii) one or more gram-positive bacteria; (iii) one or more antibiotic-sensitive bacteria; (iv) one or more antibiotic-resistant bacteria; (v) a bacterial pathogen that is selected from *Staphylococcus aureus* (*S. aureus*), MRSA (methicillin-resistant *S. aureus*), *Staphylococcus epidermidis*, MRSE (methicillin-resistant *S. epidermidis*), *Mycobacterium tuberculosis, Mycobacterium avium, Pseudomonas aeruginosa*, drug-resistant *P. aeruginosa, Escherichia coli*, enterotoxigenic *E. coli*, enterohemorrhagic *E. coli, Klebsiella pneumoniae, Clostridium difficile, Heliobacter pylori, Legionella pneumophila, Enterococcus faecalis*, methicillin-susceptible *Enterococcus faecalis, Enterobacter cloacae, Salmonella typhimurium, Proteus vulgaris, Yersinia enterocolitica, Vibrio cholera, Shigella flexneri*, vancomycin-resistant *Enterococcus* (VRE), *Burkholderia* cepacia complex, *Francisella tularensis, Bacillus anthracis, Yersinia pestis, Pseudomonas aeruginosa*, vancomycin-resistant enterococci, *Streptococcus pneumonia*, penicillin-resistant *Streptococcus pneumonia, Escherichia coli, Burkholderia cepacia, Bukholderia multivorans, Mycobacterium smegmatis* and *Acinetobacter baumannii.*

In certain embodiments the bacterial pathogen exhibits resistance to an antibiotic that is selected from methicillin, vancomycin, naficilin, gentamicin, ampicillin, chloramphenicol, doxycycline, tobramycin, clindamicin and gatifloxacin.

In certain embodiments the natural surface comprises an oral/buccal cavity surface. In further embodiments, the natural surface comprises a biological surface such as bone, joint, muscle, ligament, or tendon.

In certain embodiments the surface comprises a tissue that is selected from the group consisting of epidermis, dermis, respiratory tract, gastrointestinal tract and glandular linings. In certain embodiments the step of contacting is performed one or a plurality of times. In certain embodiments at least one step of contacting comprises one of spraying, irrigating, dipping and painting the surface. In certain other embodiments at least one step of contacting comprises one of inhaling, ingesting and orally irrigating. In certain embodiments at least one step of contacting comprises administering by a route that is selected from topically, intraperitoneally, orally, parenterally, intravenously, intraarterially, transdermally, sublingually, subcutaneously, intramuscularly, transbuccally, intranasally, via inhalation, intraoccularly, intraauricularly, intraventricularly, subcutaneously, intraadiposally, intraarticularly and intrathecally. In certain embodiments the BT composition comprises one or more BT compounds selected from Bis-BAL, BisEDT, Bis-dimercaprol, Bis-DTT, Bis-2-mercaptoethanol, Bis-DTE, Bis-Pyr, Bis-Ery, Bis-Tol, Bis-BDT, Bis-PDT, Bis-Pyr/Bal, Bis-Pyr/BDT, Bis-Pyr/EDT, Bis-Pyr/PDT, Bis-Pyr/Tol, Bis-Pyr/Ery, bismuth-1-mercapto-2-propanol, and Bis-EDT/2-hydroxy-1-propanethiol. In certain embodiments the synergizing and/or enhancing antibiotic comprises an antibiotic that is selected from clindamicin, gatifloxacin, an aminoglycoside antibiotic, a carbapenem antibiotic, a cephalosporin antibiotic, a fluoroquinolone antibiotic, a glycopeptide antibiotic, a lincosamide antibiotic, a penicillinase-resistant penicillin antibiotic, and an aminopenicillin antibiotic. In certain embodiments the synergizing and/or enhancing antibiotic is an aminoglycoside antibiotic that is selected from amikacin, arbekacin, gentamicin, kanamycin, neomycin, netilmicin, paromomycin, rhodostreptomycin, streptomycin, tobramycin and apramycin.

Turning to another embodiment there is provided an antiseptic composition, comprising (a) at least one BT compound; (b) at least one antibiotic compound that is enhanced by and/or is capable of acting synergistically with the BT compound; and (c) a pharmaceutically acceptable excipient or carrier, including a carrier for topical use. In certain embodiments the BT compound is selected from BisBAL, BisEDT, Bis-dimercaprol, Bis-DTT, Bis-2-mercaptoethanol, Bis-DTE, Bis-Pyr, Bis-Ery, Bis-Tol, Bis-BDT, Bis-PDT, Bis-Pyr/Bal, Bis-Pyr/BDT, Bis-Pyr/EDT, Bis-Pyr/PDT, Bis-Pyr/Tol, Bis-Pyr/Ery, bismuth-1-mercapto-2-propanol, and Bis-EDT/2-hydroxy-1-propanethiol. In certain embodiments the BT composition comprises a plurality of microparticles that comprise a bismuth-thiol (BT) compound, substantially all of said microparticles having a volumetric mean diameter of from about 0.4 μm to about 5 μm. In certain embodiments the BT compound is selected from BisEDT and BisBAL. In certain embodiments the antibiotic compound comprises an antibiotic that is selected from methicillin, vancomycin, naficilin, gentamicin, ampicillin, chloramphenicol, doxycycline, tobramycin, clindamicin, gatifloxacin and an aminoglycoside antibiotic. In certain embodiments the aminoglycoside antibiotic is selected from amikacin, arbekacin, gentamicin, kanamycin, neomycin, netilmicin, paromomycin, rhodostreptomycin, streptomycin, tobramycin and apramycin. In certain embodiments the aminoglycoside antibiotic is amikacin.

In certain other embodiments there is provided a method for treating a natural surface that supports or contains bacterial biofilm, comprising (a) identifying a bacterial infection on or in the surface as comprising one of (i) gram positive bacteria, (ii) gram negative bacteria, and (iii) both (i) and (ii); and (b) administering a formulation that comprises one or more bismuth thiol (BT) compositions to the surface, wherein (i) if the bacterial infection comprises gram positive bacteria, then the formulation comprises therapeutically effective amounts of at least one BT compound and at least one antibiotic that is rifamycin, (ii) if the bacterial infection comprises gram negative bacteria, then the formulation comprises therapeutically effective amounts of at least one BT compound and amikacin, (iii) if the bacterial infection comprises both gram positive and gram negative bacteria, then the formulation comprises therapeutically effective amounts of one or a plurality of BT compounds, rifamycin and amikacin, and thereby treating the surface.

In certain embodiments the biofilm comprises one or a plurality of antibiotic-resistant bacteria. In certain embodiments treating the surface comprises at least one of: (i) eradicating the bacterial biofilm, (ii) reducing the bacterial biofilm, and (iii) impairing growth of the bacterial biofilm. In certain embodiments the BT composition comprises a plurality of microparticles that comprise a bismuth-thiol (BT) compound, substantially all of said microparticles having a volumetric mean diameter of from about 0.4 µm to about 5 µm.

These and other aspects of the herein described invention embodiments will be evident upon reference to the following detailed description and attached drawings. All of the U.S. patents, U.S. patent application publications, U.S. patent applications, foreign patents, foreign patent applications and non-patent publications referred to in this specification and/or listed in the Application Data Sheet, including U.S. RE37, 793, U.S. Pat. No. 6,248,371, U.S. Pat. No. 6,086,921, and U.S. Pat. No. 6,380,248, are incorporated herein by reference in their entirety, as if each was incorporated individually. Aspects and embodiments of the invention can be modified, if necessary, to employ concepts of the various patents, applications and publications to provide yet further embodiments.

DETAILED DESCRIPTION

Figure 1:
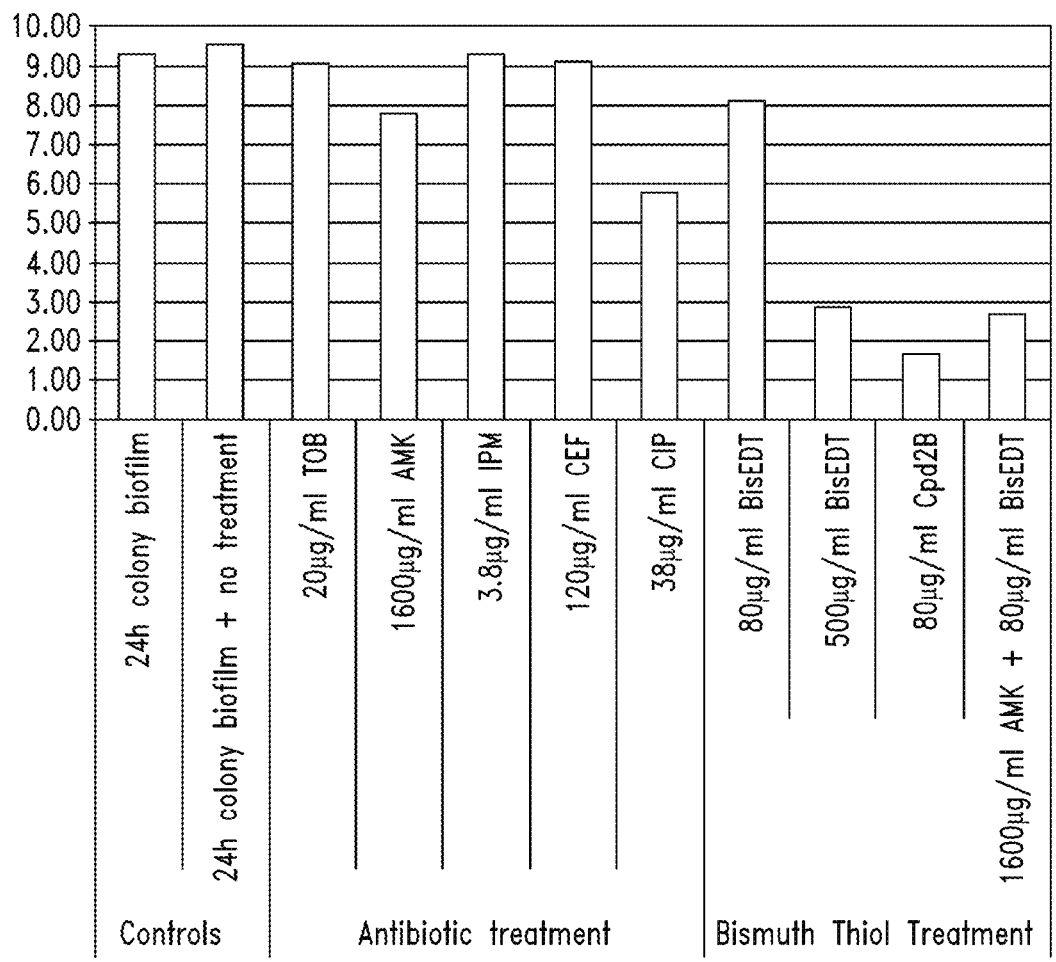
FIG. 1 shows surviving numbers (log CFU; colony forming units) from *Pseudomonas aeruginosa* colony biofilms grown for 24 hours on 10% tryptic soy agar (TSA) at 37° C., followed with indicated treatment for 18 hours. Indicated antibiotic treatments are TOB, tobramycin 10×MIC; AMK, amikacin 100×MIC; IPM, imipenem 10×MIC; CEF, cefepime 10×MIC; CIP, ciprofloxacin 100×MIC; Cpd 2B, compound 2B (Bis-BAL, 1:1.5). (MIC; minimum inhibitory concentration, e.g., lowest concentration that prevents bacterial growth).

Particular embodiments of the invention disclosed herein are based on the surprising discovery that certain bismuth-thiol (BT) compounds as provided herein (in certain embodiments including BT microparticles having a volumetric mean diameter of from about 0.4 µm to about 5 µm), but not certain other BT compounds (even if provided as microparticles), exhibited potent antiseptic, antibacterial and/or anti-biofilm activity against particular bacteria, including bacteria associated with a number of clinically significant infections including infections that can comprise bacterial biofilms.

Unexpectedly, not all BT compounds were uniformly effective against such bacteria in a predictable fashion, but instead exhibited different potencies depending on the target bacterial species. In particular and as described herein, certain BT compounds (preferably including BT microparticles having a volumetric mean diameter of from about 0.4 µm to about 5 µm) were found to exhibit higher potency against gram-negative bacteria, while certain other BT compounds (preferably including BT microparticles having a volumetric mean diameter of from about 0.4 µm to about 5 µm) were found to exhibit greater potency against gram-positive bacteria, in a manner that, according to non-limiting theory, may for the first time afford clinically relevant strategies for the management of bacterial infections, including bacterial biofilm infections.

Additionally, and as described in greater detail below, certain embodiments of the invention described herein relate to surprising advantages that are provided by novel bismuth-thiol (BT) compositions that, as disclosed herein, can be made in preparations that comprise a plurality of BT microparticles that are substantially monodisperse with respect to particle size (e.g., having volumetric mean diameter from about 0.4 µm to about 5 µm). In certain of these and related embodiments, the microparticulate BT is not provided as a component of a lipid vesicle or liposome such as a multilamellar phosphocholine-cholesterol liposome or other multilamellar or unilamellar liposomal vesicle.

As also disclosed herein, with respect to certain embodiments, it has been discovered that antibacterial and antibiofilm efficacies of certain antibiotics, which antibiotics have previously been found to lack potent therapeutic effect against such bacterial infections, may be significantly enhanced (e.g., increased in a statistically significant manner) by treating the infection (e.g., by direct application on or in an infected site such as a natural surface) with one or more of these antibiotics in concert, simultaneously or sequentially and in either order, with a selected BT compound. In a manner that could not be predicted prior to the present disclosure, certain BT compounds can be combined with certain antibiotics to provide a synergizing or enhancing combination as provided herein with respect to antibacterial and/or anti-biofilm activity against certain bacterial species or bacterial strains. The unpredicted nature of such combinations, as described in greater detail below, is evidenced by the observations that while certain BT/antibiotic combinations acted synergistically or exhibited enhancement against certain bacteria, certain other BT/antibiotic combinations failed to exhibit such synergistic or enhanced antibacterial and/or antibiofilm activity.

According to these and related embodiments, the antibiotic and the BT compound may be administered simultaneously or sequentially and in either order, and it is noteworthy that the specific synergizing or enhancing combinations of one or more antibiotic and one or more BT compound as disclosed herein for treatment of a particular infection (e.g., a biofilm formed by gram-negative or gram-positive bacteria) did not exhibit predictable (e.g., merely additive) activities but instead acted in an unexpectedly synergistic or enhancing (e.g., supra-additive) fashion, as a function of the selected antibiotic, the selected BT compound and the specifically identified target bacteria.

For example, by way of illustration and not limitation, disclosed herein in the context of a wide variety of actually or potentially microbially infected natural surfaces, and further in the context of improved substantially monodisperse microparticulate BT formulations, either or both of a particular antibiotic compound and a particular BT compound may exert limited antibacterial effects when used alone against a particular bacterial strain or species, but the combination of both the antibiotic compound and the BT compound exerts a potent antibacterial effect against the same bacterial strain or species, which effect is greater in magnitude (with statistical significance) than the simple sum of the effects of each compound when used alone, and is therefore believed according to non-limiting theory to reflect antibiotic-BT synergy (e.g., FICI≤0.5) or an enhancing effect (e.g., 0.5<FICI≤1.0) of the BT on the antibiotic potency and/or of the antibiotic on the BT potency. Accordingly, not every BT compound may synergize with, or be enhancing for, every antibiotic, and not every antibiotic may synergize with, or be enhancing for, every BT compound, such that antibiotic-BT synergy and BT-antibiotic enhancement generally are not predictable. Instead, and according to certain embodiments as disclosed herein, specific combinations of synergizing or enhancing antibiotic and BT compounds surprisingly confer potent antibacterial effects against particular bacteria, including in particular environments such as natural surfaces as described herein, and further including in certain situations antibacterial effects against biofilms formed by the particular bacteria.

That is, certain BT-synergizing antibiotics are described herein, which includes an antibiotic that is capable of acting synergistically (FICI≤0.5) with at least one BT composition that comprises at least one BT compound as provided herein, where such synergy manifests as a detectable effect that is greater (i.e., in a statistically significant manner relative to an appropriate control condition) in magnitude than the effect that can be detected when the antibiotic is present but the BT compound is absent, and/or when the BT compound is present but the antibiotic is absent. Similarly, certain BT-antibiotic combinations exhibit enhancement (0.5<FICI≤1.0), where such enhancement manifests as a detectable effect that is greater (i.e., in a statistically significant manner relative to an appropriate control condition) in magnitude than the effect that can be detected when the antibiotic is present but the BT compound is absent, and/or when the BT compound is present but the antibiotic is absent.

Examples of such a detectable effect may in certain embodiments include (i) prevention of infection by a bacterial pathogen, (ii) inhibition of cell viability or cell growth of substantially all planktonic cells of a bacterial pathogen, (iii) inhibition of biofilm formation by a bacterial pathogen, and (iv) inhibition of biofilm viability or biofilm growth of substantially all biofilm-form cells of a bacterial pathogen, but the invention is not intended to be so limited, such that in other contemplated embodiments antibiotic-BT synergy may manifest as one or more detectable effects that may include alteration (e.g., a statistically significant increase or decrease) of one or more other clinically significant parameters, for example, the degree of resistance or sensitivity of a bacterial pathogen to one or more antibiotics or other drugs or chemical agents, the degree of resistance or sensitivity of a bacterial pathogen to one or more chemical, physical or mechanical conditions (e.g., pH, ionic strength, temperature, pressure), and/or the degree of resistance or sensitivity of a bacterial pathogen to one or more biological agents (e.g., a virus, another bacterium, a biologically active polynucleotide, an immunocyte or an immunocyte product such as an antibody, cytokine, chemokine, enzyme including degradative enzymes, membrane-disrupting protein, a free radical such as a reactive oxygen species, or the like).

Persons familiar with the art will appreciate these and a variety of other criteria by which the effects of particular agents on the structure, function and/or activity of a bacterial population may be determined (e.g., Coico et al. (Eds.), Current Protocols in Microbiology, 2008, John Wiley & Sons, Hoboken, N.J.; Schwalbe et al., Antimicrobial Susceptibility Testing Protocols, 2007, CRC Press, Boca Raton, Fla.), for purposes of ascertaining antibiotic-BT synergy or enhancement which, as provided herein, is present when the effects of the synergizing or enhancing antibiotic-BT combination exceed the mere sum of the effects observed when one component of the combination is not present.

For example, in certain embodiments synergy may be determined by determining an antibacterial effect such as those described herein using various concentrations of candidate agents (e.g., a BT and an antibiotic individually and in combination) to calculate a fractional inhibitory concentration index (FICI) and a fractional bactericidal concentration index (FBCI), according to Eliopoulos et al. (Eliopoulos and Moellering, (1996) Antimicrobial combinations. In Antibiotics in Laboratory Medicine (Lorian, V., Ed.), pp. 330-96, Williams and Wilkins, Baltimore, Md., USA). Synergy may be defined as an FICI or FBCI index of ≤0.5, and antagonism at >4. (e.g., Odds, F C (2003) Synergy, antagonism, and what the chequerboard puts between them. *Journal of Antimicrobial Chemotherapy* 52:1). Synergy may also be defined conventionally as ≥4-fold decrease in antibiotic concentration, or alternatively, using fractional inhibitory concentration (FIC) as described, e.g., by Hollander et al. (1998 *Antimicrob. Agents Chemother.* 42:744). In certain embodiments, synergy may be defined as an effect that results from a combination of two drugs (e.g., an antibiotic and a BT composition) wherein the effect of the combination is greater (e.g., in a statistically significant manner) than it would be if the concentration of the second drug is replaced by the first drug.

Accordingly as described herein and in certain preferred embodiments, a combination of BT and antibiotic will be understood to synergize when a FICI value that is less than or equal to 0.5 is observed. (Odds, 2003). As also described herein, in certain other preferred embodiments and according to non-limiting theory, it is disclosed that certain BT-antibiotic combinations may exhibit a FICI value between 0.5 and 1.0 that signifies a high potential for such synergy, and which may be observed using non-optimal concentrations of at least one BT and at least one antibiotic that exhibit unilateral or mutually enhanced cooperative antimicrobial efficacy. Such an effect may also be referred to herein as "enhanced" antibiotic activity or "enhanced" BT activity.

Enhanced antibiotic and/or BT activity may be detected according to certain embodiments when the presence both (i) of at least one BT at a concentration that is less (in a statistically significant manner) than the characteristic minimum inhibitory concentration (MIC) for that BT for a given target microbe (e.g., a given bacterial species or strain), and (ii) of at least one antibiotic at a concentration that is less (in a statistically significant manner) than the characteristic $IC_{50}$ (concentration that inhibits the growth of 50% of a microbial population; e.g., Soothill et al., 1992 *J Antimicrob Chemother* 29(2):137) and/or that is less than the biofilm-prevention concentration (BPC) of that antibiotic for the given target microbe, results in enhanced (in a statistically significant manner) antimicrobial efficacy of the BT-antibiotic combination relative to the antimicrobial effect that would be observed if either antimicrobial agent (e.g., the BT or the antibiotic) were used at the same concentration in the absence of the other antimicrobial agent (e.g., the antibiotic or the BT). In preferred embodiments, "enhanced" antibiotic and/or BT activity is present when a FICI value that is less than or equal to 1.0, and greater than 0.5, is determined.

As will be appreciated by the skilled person based on the present disclosure, in certain embodiments synergistic or enhanced antibiotic and/or BT activity may be determined according to methods known in the art, such as using Loewe additivity-based models (e.g., FIC index, Greco model), or Bliss independence based models (e.g., non-parametric and semi-parametric models) or other methods described herein and known in the art (e.g., Meletiadis et al., 2005 *Medical Mycology* 43:133-152). Illustrative methods for determining synergy or enhanced antibiotic and/or BT activity are thus described, for instance, in Meletiadis et al., 2005 *Medical Mycology* 43:133-152 and references cited therein (see also, Meletiadis et al., 2002 *Rev Med Microbiol* 13:101-117; White et al., 1996 *Antimicrob Agents Chemother* 40:1914-1918; Mouton et al., 1999 *Antimicrob Agents Chemother* 43:2473-2478).

Certain other embodiments contemplate specific combinations of one or more antibiotic and one or more BT compound as disclosed herein that may exhibit synergizing or enhancing effects in vivo for treatment of a particular infection (e.g., a biofilm formed by gram-negative or gram-positive bacteria), even where the BT compound(s) and antibiotic(s) did not exhibit predictable (e.g., merely additive) activities in vivo but instead acted in an unexpectedly synergistic or enhancing (e.g., supra-additive; or conferring an effect when two or more such agents are present in combination that is greater (e.g., in a statistically significant manner) than the effect that is obtained if the concentration of the second agent is replaced by the first agent) fashion, as a function of the selected antibiotic, the selected BT compound and one or more of the specifically identified target bacterial species of which the infection is comprised. It will therefore be appreciated, according to these and related embodiments, that in certain in vivo situations FICI or FBCI values (which are determined in vitro) may not be readily available, but that instead BT-antibiotic synergizing or enhancing effects may be determined in a manner afforded by the quantifiable metrics of the infection.

For example, in one embodiment, such as in the in vivo open fracture *Rattus norvegicus* femur critical defect model as described in Example 11, a statistically significant reduction in bacterial counts observed post-treatment for the BT-antibiotic combination as compared to the antibiotic treatment or BT compound alone, is an indication of synergizing or enhancing effects. Statistical significance can be determined using methods well-known to the skilled person. In certain other embodiments, a reduction observed in this or other in vivo models by at least 5%, 10%, 20%, 30%, 40%, or 50% of bacterial counts observed in the injury post-treatment for the BT-antibiotic combination as compared to the antibiotic treatment or BT compound alone is considered an indication of synergizing or enhancing effects.

Other exemplary indicia of in vivo infections may be determined according to established methodologies that have been developed for quantification of the severity of the infection, such as a variety of wound scoring systems known to the skilled person (see e.g., scoring systems reviewed in European Wound Management Association (EWMA), Position Document: *Identifying criteria for wound infection*. London: MEP Ltd, 2005). Illustrative wound scoring systems that may be used in assessing synergistic or enhancement activity of BT-antibiotic combinations as described herein include ASEPSIS (Wilson A P, *J Hosp Infect* 1995; 29(2): 81-86; Wilson et al., Lancet 1986; 1: 311-13), the Southampton Wound Assessment Scale (Bailey I S, Karran S E, Toyn K, et al. *BMJ* 1992; 304: 469-71). See also, Horan T C, Gaynes P, Martone W J, et al., 1992 *Infect Control Hosp Epidemiol* 1992; 13: 606-08. Additionally, recognized clinical indicia of wound healing known to the skilled clinician may also be measured in the presence or absence of BT compounds and/or antibiotics, such as wound size, depth, granulation tissue condition, infection, etc. Accordingly, and based on the present disclosure, the skilled person will readily appreciate a variety of methods for determining whether a BT composition—antibiotic combination alters (e.g., increases or decreases in a statistically significant manner relative to appropriate controls) in vivo wound healing.

In view of these and related embodiments, there are provided herein a wide variety of methods for treating microbially infected natural surfaces such as surfaces that support or contain bacterial biofilms, with an effective amount (e.g., in certain embodiments a therapeutically effective amount) of a composition or formulation that comprises one or more BT compounds and, optionally, one or more antibiotic compounds, such as one or more synergizing antibiotics, or one or more enhancing antibiotics, as provided herein. It will be appreciated that based on the present disclosure, certain antibiotics are now contemplated for use in the treatment of given types of infections, where such antibiotics had previously been viewed by persons familiar with the art as ineffective against infections of the same type.

Certain embodiments thus contemplate compositions that comprise one or more BT compounds for use as antiseptics. An antiseptic is a substance that kills or prevents the growth of microorganisms, and may be typically applied to living tissue, distinguishing the class from disinfectants, which are usually applied to inanimate objects (Goodman and Gilman's "*The Pharmacological Basis of Therapeutics*", Seventh Edition, Gilman et al., editors, 1985, Macmillan Publishing Co., (hereafter, Goodman and Gilman") pp. 959-960). Common examples of antiseptics are ethyl alcohol and tincture of iodine. Germicides include antiseptics that kill microbes such as microbial pathogens.

Certain embodiments described herein may contemplate compositions that comprise one or more BT compounds and one or more antibiotic compound (e.g., a synergizing antibiotic and/or an enhancing antibiotic as provided herein). Antibiotics are known in the art and typically comprise a drug made from a compound produced by one species of microorganism to kill another species of microorganism, or a synthetic product having an identical or similar chemical structure and mechanism of action, e.g., a drug that destroys microorganisms within or on the body of a living organism, including such drug when applied topically. Among embodiments disclosed herein are those in which an antibiotic may belong to one of the following classes: aminoglycosides, carbapenems, cephalosporins, fluoroquinolones, glycopeptide antibiotics, lincosamides (e.g., clindamycin), penicillinase-resistant penicillins, and aminopenicillins. Antibiotics thus may include, but need not be limited to, oxacillin, piperacillin, cefuroxime, cefotaxime, cefepime, imipenem, aztreonam, streptomycin, tobramycin, tetracycline, minocycline, ciprofloxacin, levofloxacin, erythromycin, linezolid, phosphomycin, capreomycin, isoniazid, ansamycin, carbacephem, monobactam, nitrofuran, penicillin, quinolone, sulfonamide, Clofazimine, Dapsone, Capreomycin, Cycloserine, Ethambutol, Ethionamide, Isoniazid, Pyrazinamide, Rifampicin, Rifampin, Rifabutin, Rifapentine, Streptomycin, Arsphenamine, Chloramphenicol, Fosfomycin, Fusidic acid, Linezolid, Metronidazole, Mupirocin, Platensimycin, Quinupristin, Dalfopristin, Rifaximin, Thiamphenicol, Timidazole, aminoglycoside, beta-lactam, penicillin, cephalosporin, carbapenem, fluoroquinolone, ketolide, lincosamide, macrolide, oxazolidinone, stretogramin, sulphonamide, tetracycline, glycylcycline, methicillin, vancomycin, naficilin, gentamicin, ampicillin, chloramphenicol, doxycycline, tobramycin, amikacin, arbekacin, gentamicin, kanamycin, neomycin, netilmicin, paromomycin, rhodostreptomycin, streptomycin, tobramycin, apramycin, clindamicin, gatifloxacin, aminopenicillin, and others known to the art. Compendia of these and other clinically useful antibiotics are available and known to those familiar with the art (e.g., Washington University School of Medicine, *The Washington Manual of Medical Therapeutics* (32$^{nd}$ Ed.), 2007 Lippincott, Williams and Wilkins, Philadelphia, Pa.; Hauser, A L, *Antibiotic Basics for Clinicians*, 2007 Lippincott, Williams and Wilkins, Philadelphia, Pa.).

An exemplary class of antibiotics for use with one or more BT compounds in certain herein disclosed embodiments is the aminoglycoside class of antibiotics, which are reviewed in Edson R S, Terrell C L. *The aminoglycosides. Mayo Clin Proc.* 1999 May; 74(5):519-28. This class of antibiotics inhibits bacterial growth by impairing bacterial protein synthesis, through binding and inactivation of bacterial ribosomal subunits. In addition to such bacteriostatic properties, aminoglycosides also exhibit bacteriocidal effects through disruption of cell walls in gram-negative bacteria.

Aminoglycoside antibiotics include gentamicin, amikacin, streptomycin, and others, and are generally regarded as useful in the treatment of gram-negative bacteria, mycobacteria and other microbial pathogens, although cases of resistant strains have been reported. The aminoglycosides are not absorbed through the digestive tract and so are not generally regarded as being amenable to oral formulations. Amikacin, for example, although often effective against gentamicin-resistant bacterial strains, is typically administered intravenously or intramuscularly, which can cause pain in the patient. Additionally, toxicities associated with aminoglycoside antibiotics such as amikacin can lead to kidney damage and/or irreversible hearing loss.

Despite these properties, certain embodiments disclosed herein contemplate oral administration of a synergizing BT/antibiotic combination (e.g., where the antibiotic need not be limited to an aminoglycoside) for instance, for treatment of an epithelial tissue surface at one or more locations along the oral cavity, gastrointestinal tract/alimentary canal. Also contemplated in certain other embodiments may be use of compositions and methods described herein as disinfectants, which refers to preparations that kill, or block the growth of, microbes on an external surface of an inanimate object.

As also described elsewhere herein, a BT compound may be a composition that comprises bismuth or a bismuth salt and a thiol- (e.g., —SH, or sulfhydryl) containing compound, including those that are described (including their methods of preparation) in Domenico et al., 1997 *Antimicrob. Agent. Chemother.* 41(8):1697-1703, Domenico et al., 2001 *Antimicob. Agent. Chemother.* 45(5):1417-1421, and in U.S. RE37, 793, U.S. Pat. No. 6,248,371, U.S. Pat. No. 6,086,921, and U.S. Pat. No. 6,380,248; see also, e.g., U.S. Pat. No. 6,582, 719. Certain embodiments are not so limited, however, and may contemplate other BT compounds that comprise bismuth or a bismuth salt and a thiol-containing compound. The thiol-containing compound may contain one, two, three, four, five, six or more thiol (e.g., —SH) groups. In preferred embodiments the BT compound comprises bismuth in association with the thiol-containing compound via ionic bonding and/or as a coordination complex, while in some other embodiments bismuth may be associated with the thiol-containing compound via covalent bonding such as may be found in an organometallic compound. Certain contemplated embodiments, however, expressly exclude a BT compound that is an organometallic compound such as a compound in which bismuth is found in covalent linkage to an organic moiety.

Exemplary BT compounds are shown in Table 1:

TABLE 1

| Exemplary BT Compounds* |
|---|
| 1) CPD 1B-1 Bis-EDT (1:1) $BiC_2H_4S_2$ |
| 2) CPD 1B-2 Bis-EDT (1:1.5) $BiC_3H_6S_3$ |
| 3) CPD 1B-3 Bis-EDT (1:1.5) $BiC_3H_6S_3$ |
| 4) CPD 1C Bis-EDT (1:1.5) $BiC_3H_6S_3$ |
| 5) CPD 2A Bis-Bal (1:1) $BiC_3H_6S_2O$ |
| 6) CPD 2B Bis-Bal (1:1.5) $BiC_{4.5}H_9O_{1.5}S_3$ |
| 7) CPD 3A Bis-Pyr (1:1.5) $BiC_{7.5}H_6N_{1.5}O_{1.5}S_{1.5}$ |
| 8) CPD 3B Bis-Pyr (1:3) $BiC_{15}H_{12}N_3O_3S_3$ |
| 9) CPD 4 Bis-Ery (1:1.5) $BiC_6H_{12}O_3S_3$ |
| 10) CPD 5 Bis-Tol (1:1.5) $BiC_{10.5}H_9S_3$ |
| 11) CPD 6 Bis-BDT (1:1.5) $BiC_6H_{12}S_3$ |
| 12) CPD 7 Bis-PDT (1:1.5) $BiC_{4.5}H_9S_3$ |
| 13) CPD 8-1 Bis-Pyr/BDT (1:1/1) |
| 14) CPD 8-2 Bis-Pyr/BDT (1:1/0.5) |

TABLE 1-continued

Exemplary BT Compounds*

15) CPD 9 Bis-2hydroxy, propane thiol (1:3)
16) CPD 10 Bis-Pyr/Bal (1:1/0.5)
17) CPD 11 Bis-Pyr/EDT (1:1/0.5)
18) CPD 12 Bis-Pyr/Tol (1:1/0.5)
19) CPD 13 Bis-Pyr/PDT (1:1/0.5)
20) CPD 14 Bis-Pyr/Ery (1:1/0.5)
21) CPD 15 Bis-EDT/2hydroxy, propane thiol (1:1/1)

*Shown are atomic ratios relative to a single bismuth atom, for comparison, based on the stoichiometric ratios of the reactants used and the known propensity of bismuth to form trivalent complexes with sulfur containing compounds. Atomic ratios as shown may not be accurate molecular formulae for all species in a given preparation. The numbers in parenthesis are the ratios of bismuth to one (or more) thiol agents. (e.g. Bi:thiol1/thiol2) "CPD", compound.

BT compounds for use in certain of the presently disclosed embodiments may be prepared according to established procedures (e.g., U.S. RE37,793, U.S. Pat. No. 6,248,371, U.S. Pat. No. 6,086,921, and U.S. Pat. No. 6,380,248; Domenico et al., 1997 *Antimicrob. Agent. Chemother.* 41(8):1697-1703, Domenico et al., 2001 *Antimicob. Agent. Chemother.* 45(5): 1417-1421) and in certain other embodiments BT compounds may also be prepared according to methodologies described herein. Certain preferred embodiments thus contemplate the herein described synthetic methods for preparing BT compounds, and in particular for obtaining BT compounds in substantially monodisperse microparticulate form, in which an acidic aqueous bismuth solution that contains dissolved bismuth at a concentration of at least 50 mM, at least 100 mM, at least 150 mM, at least 200 mM, at least 250 mM, at least 300 mM, at least 350 mM, at least 400 mM, at least 500 mM, at least 600 mM, at least 700 mM, at least 800 mM, at least 900 mM or at least 1 M and that lacks a hydrophilic, polar or organic solubilizer is admixed with ethanol to obtain a first ethanolic solution, which is reacted with a second ethanolic solution comprising a thiol-containing compound to obtain a reaction solution, wherein the thiol-containing compound is present in the reaction solution at a molar ratio of from about 1:3 to about 3:1 relative to the bismuth, under conditions and for a time sufficient for formation of a precipitate which comprises the microparticles comprising the BT compound (such as the conditions of concentration, solvent strength, temperature, pH, mixing and/or pressure, and the like, as described herein and as will be appreciated by the skilled person based on the present disclosure).

Accordingly, exemplary BTs include compound 1B-1, Bis-EDT (bismuth-1,2-ethane dithiol, reactants at 1:1); compound 1B-2, Bis-EDT (1:1.5); compound 1B-3, Bis-EDT (1:1.5); compound 1C, Bis-EDT (soluble Bi preparation, 1:1.5); compound 2A, Bis-Bal (bismuth-British anti-Lewisite (bismuth-dimercaprol, bismuth-2,3-dimercaptopropanol), 1:1); compound 2B, Bis-Bal (1:1.5); compound 3A Bis-Pyr (bismuth-pyrithione, 1:1.5); compound 3B Bis-Pyr (1:3); compound 4, Bis-Ery (bismuth-dithioerythritol, 1:1.5); compound 5, Bis-Tol (bismuth-3,4-dimercaptotoluene, 1:1.5); compound 6, Bis-BDT (bismuth-2,3-butanedithiol, 1:1.5); compound 7, Bis-PDT (bismuth-1,3-propanedithiol, 1:1.5); compound 8-1 Bis-Pyr/BDT (1:1/1); compound 8-2, Bis-Pyr/BDT (1:1/0.5); compound 9, Bis-2-hydroxy, propane thiol (bismuth-1-mercapto-2-propanol, 1:3); compound 10, Bis-Pyr/Bal (1:1/0.5); compound 11, Bis-Pyr/EDT (1:1/0.5); compound 12 Bis-Pyr/Tol (1:1/0.5); compound 13, Bis-Pyr/PDT (1:1/0.5); compound 14 Bis-Pyr/Ery (1:1/0.5); compound 15, Bis-EDT/2-hydroxy, propane thiol (1:1/1) (see, e.g., Table 1).

Without wishing to be bound by theory, it is believed that the presently disclosed methods of preparing a BT compound, which in certain preferred embodiments may comprise preparing or obtaining an acidic aqueous liquid solution that comprises bismuth such as an aqueous nitric acid solution comprising bismuth nitrate, may desirably yield compositions comprising BT compounds where such compositions have one or more desirable properties, including ease of large-scale production, improved product purity, uniformity or consistency (including uniformity in particle size), or other properties useful in the preparation and/or administration of the present topical formulations.

In particular embodiments it has been discovered that BT compositions, prepared according to the methods described herein for the first time, exhibit an advantageous degree of homogeneity with respect to their occurrence as a substantially monodisperse suspension of microparticles each having a volumetric mean diameter (VMD) according to certain presently preferred embodiments of from about 0.4 µm to about 5 µm. Measures of particle size can be referred to as volumetric mean diameter (VMD), mass median diameter (MMD), or mass median aerodynamic diameter (MMAD). These measurements may be made, for example, by impaction (MMD and MMAD) or by laser (VMD) characterization. For liquid particles, VMD, MMD and MMAD may be the same if environmental conditions are maintained, e.g., standard humidity. However, if humidity is not maintained, MMD and MMAD determinations will be smaller than VMD due to dehydration during impactor measurements. For the purposes of this description, VMD, MMD and MMAD measurements are considered to be under standard conditions such that descriptions of VMD, MMD and MMAD will be comparable. Similarly, dry powder particle size determinations in MMD, and MMAD are also considered comparable.

As described herein, preferred embodiments relate to a substantially monodisperse suspension of BT-containing microparticles. Generation of a defined BT particle size with limited geometric standard deviation (GSD) may, for instance, optimize BT deposition, accessibility to desired target sites in or on a natural surface, and/or tolerability by a subject to whom the BT microparticles are administered. Narrow GSD limits the number of particles outside the desired VMD or MMAD size range.

In one embodiment, a liquid or aerosol suspension of microparticles containing one or more BT compounds disclosed herein is provided having a VMD from about 0.5 microns to about 5 microns. In another embodiment, a liquid or aerosol suspension having a VMD or MMAD from about 0.7 microns to about 4.0 microns is provided. In another embodiment, a liquid or aerosol suspension having a VMD or MMAD from about 1.0 micron to about 3.0 microns is provided. In certain other preferred embodiments there is provided a liquid suspension comprising one or a plurality of BT compound particles of from about 0.1 to about 5.0 microns VMD, or of from about 0.1, about 0.2, about 0.3, about 0.4, about 0.5, about 0.6, about 0.7, about 0.8 or about 0.9 microns to about 1.0, about 1.5, about 2.0, about 2.5, about 3.0, about 3.5, about 4.0, about 4.5, about 5.0, about 5.5, about 6.0, about 6.5, about 7.0, about 7.5 or about 8.0 microns, the particle comprising a BT compound prepared as described herein.

Accordingly and in certain preferred embodiments, a BT preparation described for the first time herein which is "substantially" monodisperse, for example, a BT composition that comprises a BT compound in microparticulate form wherein "substantially" all of the microparticles have a volumetric mean diameter (VMD) within a specified range (e.g., from about 0.4 µm to about 5 µm), includes those compositions in which at least 80%, 85%, 90%, 91%, 92%, 93%, or 94%, more preferably at least 95%, 96%, 97%, 98%, 99% or more of the particles have a VMD that is within the recited size range.

These and related properties of BT compositions prepared according to the herein described synthetic methods offer unprecedented advantages over previously described BTs, including lower cost and ease of production, and uniformity within the composition that may permit its characterization in a manner that facilitates regulatory compliance according to one or more of pharmaceutical, formulary and cosmeceutical standards.

Additionally or alternatively, the herein described substantially monodisperse BT microparticles may advantageously be produced without the need for micronization, i.e., without the expensive and labor-intensive milling or supercritical fluid processing or other equipment and procedures that are typically used to generate microparticles (e.g., Martin et al. 2008 *Adv. Drug Deliv. Rev.* 60(3):339; Moribe et al., 2008 *Adv. Drug Deliv. Rev.* 60(3):328; Cape et al., 2008 *Pharm. Res.* 25(9):1967; Rasenack et al. 2004 *Pharm. Dev. Technol.* 9(1):1-13). Hence, the present embodiments offer beneficial effects of substantially uniform microparticulate preparations, including without limitation enhanced and substantially uniform solubilization properties, suitability for desired administration forms such as oral, inhaled or dermatological/skin wound topical forms, increased bioavailability and other beneficial properties.

The BT compound microparticulate suspension can be administered as aqueous formulations, as suspensions or solutions in aqueous as well as organic solvents including halogenated hydrocarbon propellants, as dry powders, or in other forms as elaborated below, including preparations that contain wetting agents, surfactants, mineral oil or other ingredients or additives as may be known to those familiar with formulary, for example, to maintain individual microparticles in suspension. Aqueous formulations may be aerosolized by liquid nebulizers employing, for instance, either hydraulic or ultrasonic atomization. Propellant-based systems may use suitable pressurized dispensers. Dry powders may use dry powder dispersion devices, which are capable of dispersing the BT-containing microparticles effectively. A desired particle size and distribution may be obtained by choosing an appropriate device.

As also noted above, also provided herein according to certain embodiments is a method for preparing a bismuth-thiol (BT) composition that comprises a plurality of microparticles that comprise a BT compound, substantially all of such microparticles having a volumetric mean diameter (VMD) of from about 0.1 to about 8 microns, and in certain preferred embodiments from about 0.4 microns to about 5 microns.

In general terms, the method comprises the steps of (a) admixing, under conditions and for a time sufficient to obtain a solution that is substantially free of a solid precipitate, (i) an acidic aqueous solution that comprises a bismuth salt comprising bismuth at a concentration of at least 50 mM and that lacks a hydrophilic, polar or organic solubilizer, with (ii) ethanol in an amount sufficient to obtain an admixture that comprises at least about 5%, 10%, 15%, 20%, 25% or 30%, and preferably about 25% ethanol by volume; and (b) adding to the admixture of (a) an ethanolic solution comprising a thiol-containing compound to obtain a reaction solution, wherein the thiol-containing compound is present in the reaction solution at a molar ratio of from about 1:3 to about 3:1 relative to the bismuth, under conditions and for a time sufficient for formation of a precipitate which comprises the BT compound.

In certain preferred embodiments the bismuth salt may be $Bi(NO_3)_3$, but it will be appreciated according to the present disclosure that bismuth may also be provided in other forms. In certain embodiments the bismuth concentration in the acidic aqueous solution may be at least 100 mM, at least 150 mM, at least 200 mM, at least 250 mM, at least 300 mM, at least 350 mM, at least 400 mM, at least 500 mM, at least 600 mM, at least 700 mM, at least 800 mM, at least 900 mM or at least 1 M. In certain embodiments the acidic aqueous solution comprises at least 5%, 10%, 15%, 20%, 22% or 22.5% bismuth by weight. The acidic aqueous solution may in certain preferred embodiments comprise at least 5% or more nitric acid by weight, and in certain other embodiments the acidic aqueous solution may comprise at least 0.5%, at least 1%, at least 1.5%, at least 2%, at least 2.5%, at least 3%, at least 3.5%, at least 4%, at least 4.5% or at least 5% nitric acid by weight.

The thiol-containing compound may be any thiol-containing compound as described herein, and in certain embodiments may comprise one or more of 1,2-ethane dithiol, 2,3-dimercaptopropanol, pyrithione, dithioerythritol, 3,4-dimercaptotoluene, 2,3-butanedithiol, 1,3-propanedithiol, 2-hydroxypropane thiol, 1-mercapto-2-propanol, dithioerythritol and dithiothreitol. Other exemplary thiol-containing compounds include alpha-lipoic acid, methanethiol ($CH_3SH$ [m-mercaptan]), ethanethiol ($C_2H_5SH$ [e-mercaptan]), 1-propanethiol ($C_3H_7SH$ [n-P mercaptan]), 2-Propanethiol ($CH_3CH(SH)CH_3$ [$2C_3$ mercaptan]), butanethiol ($C_4H_9SH$ ([n-butyl mercaptan]), tert-butyl mercaptan ($C(CH_3)_3SH$ [t-butyl mercaptan]), pentanethiols ($C_5H_{11}SH$ [pentyl mercaptan]), coenzyme A, lipoamide, glutathione, cysteine, cystine, 2-mercaptoethanol, dithiothreitol, dithioerythritol, 2-mercaptoindole, transglutaminase and any of the following thiol compounds available from Sigma-Aldrich (St. Louis, Mo.): (11-mercaptoundecyl)hexa(ethylene glycol), (11-mercaptoundecyl)tetra(ethylene glycol), (11-mercaptoundecyl)tetra(ethylene glycol) functionalized gold nanoparticles, 1,1',4',1'''-terphenyl-4-thiol, 1,11-undecanedithiol, 1,16-hexadecanedithiol, 1,2-ethanedithiol technical grade, 1,3-propanedithiol, 1,4-benzenedimethanethiol, 1,4-butanedithiol, 1,4-butanedithiol diacetate, 1,5-pentanedithiol, 1,6-hexanedithiol, 1,8-octanedithiol, 1,9-nonanedithiol, adamantanethiol, 1-butanethiol, 1-decanethiol, 1-dodecanethiol, 1-heptanethiol, 1-heptanethiol purum, 1-hexadecanethiol, 1-hexanethiol, 1-mercapto-(triethylene glycol), 1-mercapto-(triethylene glycol) methyl ether functionalized gold nanoparticles, 1-mercapto-2-propanol, 1-nonanethiol, 1-octadecanethiol, 1-octanethiol, 1-octanethiol, 1-pentadecanethiol, 1-pentanethiol, 1-propanethiol, 1-tetradecanethiol, 1-tetradecanethiol purum, 1-undecanethiol, 11-(1H-pyrrol-1-yl)undecane-1-thiol, 11-amino-1-undecanethiol hydrochloride, 11-bromo-1-undecanethiol, 11-mercapto-1-undecanol, 11-mercapto-1-undecanol, 11-mercaptoundecanoic acid, 11-mercaptoundecanoic acid, 11-mercaptoundecyl trifluoroacetate, 11-mercaptoundecylphosphoric acid, 12-mercaptododecanoic acid, 12-mercaptododecanoic acid, 15-mercaptopentadecanoic acid, 16-mercaptohexadecanoic acid, 16-mercaptohexadecanoic acid, 1H,1H,2H,2H-perfluorodecanethiol, 2,2'-(ethylenedioxy)diethanethiol, 2,3-butanedithiol, 2-butanethiol, 2-ethylhexanethiol, 2-methyl-1-propanethiol, 2-methyl-2-propanethiol, 2-phenylethanethiol, 3,3,4,4,5,5,6,6-nonafluoro-1-hexanethiol purum, 3-(dimethoxymethylsilyl)-1-propanethiol, 3-chloro-1-propanethiol, 3-mercapto-1-propanol, 3-mercapto-2-butanol, 3-mercapto-N-nonylpropionamide, 3-mercaptopropionic acid, 3-mercaptopropyl-functionalized silica gel, 3-methyl-1-butanethiol, 4,4'-bis(mercaptomethyl)biphenyl, 4,4'-dimercaptostilbene, 4-(6-mercaptohexyloxyl)benzyl alcohol, 4-cyano-1-butanethiol, 4-mercapto-1-butanol, 6-(ferrocenyl) hexanethiol, 6-mercapto-1-hexanol, 6-mercaptohexanoic acid, 8-mercapto-1-octanol, 8-mercaptooctanoic acid, 9-mercapto-1-nonanol, biphenyl-4,4'-dithiol, butyl 3-mercaptopropionate, copper(I) 1-butanethiolate, cyclohexanethiol, cyclopentanethiol, decanethiol functionalized silver nanoparticles, dodecanethiol functionalized gold nanoparticles, dodecanethiol functionalized silver nanoparticles, hexa(ethylene glycol)mono-11-(acetylthio)undecyl ether, mercaptosuccinic acid, methyl 3-mercaptopropionate, heptanoic hydrazide bisphenol A substituted 5-(Hydroxymethyl)-1,3-bis(6-mercaptohexyloxy)benzene sold under the trademark NANO TETHER BPA-HH™ (Sigma-Aldrich, St. Louis, Mo.), octadecanethiol reagents sold under the trademark NANOTHINKS™ 18 (Sigma-Aldrich), octanethiol reagents sold under the trademark NANOTHINKS™ 8 (Sigma-Aldrich), 11-mercaptoundecanoic acid reagents sold under the trademark NANOTHINKS™ ACID11 (Sigma-Aldrich), 16-mercaptorhexadecanoic acid reagents sold under the trademark NANOTHINKS™ ACID16 (Sigma-Aldrich), 11-mercapto-1-undecanol reagents sold under the trademark NANOTHINKS™ ALCO11 (Sigma-Aldrich), 1,8-octanedithiol sold under the trademark NANOTHINKS™ THIO8 (Sigma-Aldrich), octanethiol functionalized gold nanoparticles, PEG dithiol average $M_n$ 8,000, PEG dithiol average mol wt 1,500, PEG dithiol average mol wt 3,400, S-(11-bromoundecyl)thioacetate, S-(4-cyanobutyl)thioacetate, thiophenol, triethylene glycol mono-11-mercaptoundecyl ether, trimethylolpropane tris(3-mercaptopropionate), [11-(methylcarbonylthio)undecyl]tetra(ethylene glycol), m-carborane-9-thiol, p-terphenyl-4,4"-dithiol, tert-dodecylmercaptan, and tert-nonyl mercaptan.

Exemplary reaction conditions, including temperature, pH, reaction time, the use of stirring or agitation to dissolve solutes and procedures for collecting and washing precipitates, are described herein and employ techniques generally known in the art.

Unlike previously described methodologies for producing BT compounds, according to the present methods for preparing BT, BT products are provided as microparticulate suspensions having substantially all microparticles with VMD from about 0.4 to about 5 microns in certain preferred embodiments, and generally from about 0.1 microns to about 8 microns according to certain other embodiments. Further unlike previous approaches, according to the instant embodiments bismuth is provided in an acidic aqueous solution that comprises a bismuth salt at a concentration of from at least about 50 mM to about 1 M, and nitric acid in an amount from at least about 0.5% to about 5% (w/w), and preferably less than 5% (weight/weight), and that lacks a hydrophilic, polar or organic solubilizer.

In this regard the present methods offer surprising and unexpected advantages in view of generally accepted art teachings that bismuth is not water soluble at 50 μM (e.g., U.S. RE37793), that bismuth is unstable in water (e.g., Kuvshinova et al., 2009 Russ. *J Inorg. Chem.* 54(11):1816), and that bismuth is unstable even in nitric acid solutions unless a hydrophilic, polar or organic solubilizer is present. For example, in all of the definitive descriptions of BT preparation methodologies (e.g., Domenico et al., 1997 *Antimicrob. Agents. Chemother.* 41:1697; U.S. Pat. No. 6,380,248; U.S. RE37793; U.S. Pat. No. 6,248,371), the hydrophilic solubilizing agent propylene glycol is required to dissolve bismuth nitrate, and the bismuth concentration of solutions prepared for reaction with thiols is well below 15 mM, thereby limiting the available production modalities for BT compounds.

By contrast, according to the present disclosure there is no requirement for a hydrophilic, polar or organic solubilizer in order dissolve bismuth, yet higher concentrations are surprisingly achieved. Hydrophilic, polar or organic solubilizers include propylene glycol (PG) and ethylene glycol (EG) and may also include any of a large number of known solubility enhancers, including polar solvents such as dioxane and dimethylsulfoxide (DMSO), polyols (including, e.g., PG and EG and also including polyethylene glycol (PEG), polypropyleneglycol (PPG), pentaerythritol and others), polyhydric alchohols such as glycerol and mannitol, and other agents. Other water-miscible organic of high polarity include dimethylsulfoxide (DMSO), dimethylformamide (DMF) and NMP (N-methyl-2-pyrrolidone).

Thus, it will be appreciated by those familiar with the art that solvents, including those commonly used as hydrophilic, polar or organic solubilizers as provided herein, may be selected, for instance, based on the solvent polarity/polarizability (SPP) scale value using the system of Catalan et al. (e.g., 1995 *Liebigs Ann.* 241; see also Catalan, 2001 In: Handbook of Solvents, Wypych (Ed.), Andrew Publ., NY, and references cited therein), according to which, for example, water has a SPP value of 0.962, toluene a SPP value of 0.655, and 2-propanol a SPP value of 0.848. Methods for determining the SPP value of a solvent based on ultraviolet measurements of the 2-N,N-dimethyl-7-nitrofluorene/2-fluoro-7-nitrofluorene probe/homomorph pair have been described (Catalan et al., 1995).

Solvents with desired SPP values (whether as pure single-component solvents or as solvent mixtures of two, three, four or more solvents; for solvent miscibility see, e.g., Godfrey 1972 *Chem. Technol.* 2:359) based on the solubility properties of a particular BT composition can be readily identified by those having familiarity with the art in view of the instant disclosure, although as noted above, according to certain preferred embodiments regarding the herein described synthetic method steps, no hydrophilic, polar or organic solubilizer is required in order dissolve bismuth.

Solubility parameters may also include the interaction parameter C, Hildebrand solubility parameter d, or partial (Hansen) solubility parameters: δp, δh and δd, describing the solvent's polarity, hydrogen bonding potential and dispersion force interaction potential, respectively. In certain embodiments, the highest value for a solubility parameter that describes a solvent or co-solvent system in which the bismuth salt comprising bismuth will dissolve may provide a limitation for the aqueous solution that comprises the bismuth salt, for instance, according to the presently described method for preparing a microparticulate BT composition. For example, higher δh values will have a greater hydrogen bonding ability and would therefore have a greater affinity for solvent molecules such as water. A higher value of maximum observed δh for a solvent may therefore be preferred for situations where a more hydrophilic environment is desired.

By way of non-limiting example, BisEDT having the structure shown below in formula I may be prepared according to the following reaction scheme:

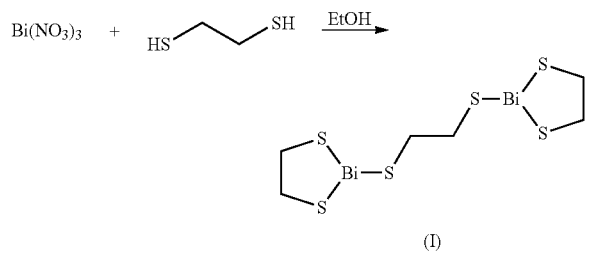

Briefly, and as a non-limiting illustrative example, to an excess (11.4 L) of 5% aqueous $HNO_3$ at room temperature may be slowly added 0.331 L (about 0.575 moles) of an aqueous acidic bismuth solution such as a $Bi(NO_3)_3$ solution (e.g., 43% $Bi(NO_3)_3$ (w/w), 5% nitric acid (w/w), 52% water (w/w), available from Shepherd Chemical Co., Cincinnati, Ohio) with stirring, followed by slow addition of absolute ethanol (4 L). An ethanolic solution (1.56 L) of a thiol compound such as 1,2-ethanedithio [~0.55 M] may be separately prepared by adding, to 1.5 L of absolute ethanol, 72.19 mL (0.863 moles) of 1,2-ethanedithiol using a 60 mL syringe, and then stirring for five minutes. 1,2-ethanedithiol (CAS 540-63-6) and other thiol compounds are available from, e.g., Sigma-Aldrich, St. Louis, Mo. The ethanolic solution of the thiol compound may then be slowly added to the aqueous $Bi(NO_3)_3/HNO_3$ solution with stirring overnight to form a reaction solution. The thiol-containing compound may be present in the reaction solution, according to certain preferred embodiments, at a molar ratio of from about 1:3 to about 3:1 relative to the bismuth. The formed product is allowed to settle as a precipitate comprising microparticles as described herein, which is then collected by filtration and washed sequentially with ethanol, water and acetone to obtain BisEDT as a yellow amorphous powdered solid. The crude product may be redissolved in absolute ethanol with stirring, then filtered and washed sequentially with ethanol several times followed by acetone several times. The washed powder may be triturated in 1M NaOH (500 mL), filtered and washed sequentially with water, ethanol and acetone to afford purified microparticulate BisEDT.

According to non-limiting theory, bismuth inhibits the ability of bacteria to produce extracellular polymeric substances (EPS) such as bacterial exopolysaccharides, and this inhibition leads to impaired biofilm formation. Bacteria are believed to employ the glue-like EPS for biofilm cohesion. Depending on the nature of an infection, biofilm formation and elaboration of EPS may contribute to bacterial pathogenicity such as interference with wound healing. However, bismuth alone is not therapeutically useful as an intervention agent, and is instead typically administered as part of a complex such as a BT. Bismuth-thiols (BTs) are thus a family of compositions that includes compounds that result from the chelation of bismuth with a thiol compound, and that exhibit dramatic improvement in the antimicrobial therapeutic efficacy of bismuth. BTs exhibit remarkable anti-infective, anti-biofilm, and immunomodulatory effects. Bismuth thiols are effective against a broad-spectrum of microorganisms, and are typically not affected by antibiotic-resistance. BTs prevent biofilm formation at remarkably low (sub-inhibitory) concentrations, prevent many pathogenic characteristics of common wound pathogens at those same sub-inhibitory levels, can prevent septic shock in animal models, and may be synergistic with many antibiotics.

As described herein, such synergy in the antibacterial effects of one or more specified BT when combined with one or more specified antibiotic compound is not readily predictable based on profiles of separate antibiotic and BT effects against a particular bacterial type, but surprisingly may result from selection of particular BT-antibiotic combinations in view of the specific bacterial population, including identification of whether gram-negative or gram-positive (or both) bacteria are present. For instance, as disclosed herein, antibiotics that synergize with certain BTs may include one or more of amikacin, ampicillin, aztreonam, cefazolin, cefepime, chloramphenicol, ciprofloxacin, clindamycin (or other lincosamide antibiotics), daptomycin (sold under the trademark CUBICIN®), doxycycline, gatifloxacin, gentamicin, imipenim, levofloxacin, linezolid (sold under the trademark ZYVOX®), minocycline, nafcilin, paromomycin, rifampin, sulphamethoxazole, tetracycline, tobramycin and vancomycin. In vitro studies showed, for example, that MRSA, which was poorly or not at all susceptible to gentamicin, cefazolin, cefepime, suphamethoxazole, imipenim or levofloxacin individually, exhibited marked sensitivity to any one of these antibiotics if exposed to the antibiotic in the presence of the BT compound BisEDT. Certain embodiments contemplated herein thus expressly contemplate compositions and/or methods in which may be included the combination of a BT compound and one or more antibiotics selected from amikacin, ampicillin, cefazolin, cefepime, chloramphenicol, ciprofloxacin, clindamycin (or another lincosamide antibiotic), daptomycin (sold under the trademark CUBICIN®), doxycycline, gatifloxacin, gentamicin, imipenim, levofloxacin, linezolid (sold under the trademark ZYVOX®), minocycline, nafcilin, paromomycin, rifampin, sulphamethoxazole, tobramycin and vancomycin, whilst certain other embodiments contemplated herein contemplate compositions and/or methods in which may be included the combination of a BT compound and one or more antibiotics from which expressly excluded may be one or more antibiotic selected from amikacin, ampicillin, cefazolin, cefepime, chloramphenicol, ciprofloxacin, clindamycin (or other lincosamides), daptomycin (sold under the trademark CUBICIN®), doxycycline, gatifloxacin, gentamicin, imipenim, levofloxacin, linezolid (sold under the trademark ZYVOX®), minocycline, nafcilin, paromomycin, rifampin, sulphamethoxazole, tobramycin and vancomycin. It is noted in this context that gentamicin and tobramycin belong to the aminoglycoside class of antibiotics. Also expressly excluded from certain contemplated embodiments are certain compositions and methods described in Domenico et al., 2001 *Agents Chemother.* 45:1417-1421; Domenico et al., 2000 *Infect. Med.* 17:123-127; Domenico et al., 2003 *Res. Adv. In Antimicrob. Agents & Chemother.* 3:79-85; Domenico et al., 1997 *Antimicrob. Agents Chemother.* 41(8):1697-1703; Domenico et al., 1999 *Infect. Immun.* 67:664-669: Huang et al. 1999 *J Antimicrob. Chemother.* 44:601-605; Veloira et al., 2003 *J Antimicrob. Chemother.* 52:915-919; Wu et al., 2002 *Am J Respir Cell Mol Biol.* 26:731-738; Halwani et al., 2008 *Int. J Pharmaceut.* 358:278; Halwani et al., 2009 *Int. J. Pharmaceut.* 373:141-146; where it will be noted that none of these publications teach or suggest the mondisperse microparticulate BT compositions that are disclosed herein.

Accordingly and as described herein, in certain preferred embodiments there are provided compositions and methods for treating a subject with a composition that comprises the herein described microparticulate BT and that optionally and in certain other embodiments also comprises a synergizing and/or an enhancing antibiotic. Persons familiar with the relevant art will, based on the present disclosure, recognize appropriate clinical contexts and situations in which such treatment may be desired, criteria for which are established in the medical arts, including inter alia, e.g., surgical, military surgical, dermatological, trauma medicine, gerontological, cardiovascular, metabolic diseases (e.g., diabetes, obesity, etc.), infection and inflammation (including in the epithelial linings of the respiratory tract or the gastrointestinal tract, or other epithelial tissue surfaces such as in glandular tissues), and other relevant medical specialties and subspecialties.

It will therefore be appreciated that, in certain embodiments as disclosed herein and known in the art, promoting skin tissue repair (or other tissue repair, such as epithelial tissue, bone, joint, muscle tendon, or ligament repair) is contemplated. In certain embodiments, promoting skin tissue or other epithelial tissue repair may comprise stimulating or disinhibiting one or more cellular wound repair activities selected from (i) epithelial cell (e.g., keratinocyte) or dermal fibroblast migration, (ii) epithelial cell (e.g., keratinocyte) or dermal fibroblast growth, (iii) downregulation of epithelial cell (e.g., keratinocyte) or dermal fibroblast collagenase, gelatinase or matrix metalloproteinase activity, (iv) dermal fibroblast extracellular matrix protein deposition, and (v) induction or potentiation of dermal angiogenesis. Methodologies for identifying and characterizing such cellular wound repair activities have been described such that the effects of the herein disclosed wound tissue repair-promoting compounds, such as compositions comprising BT agents as described herein, on these and related activities can be determined readily and without undue experimentation based on the present disclosure. For example, disclosed herein are compositions and methods that relate to art accepted models for wound repair based on keratinocyte wound closure following a scratch wound.

Preferred compositions for treating a microbial infection on or in a natural surface for use according to the embodiments described herein, may include in certain embodiments compositions that comprise bismuth-thiol (BT) compounds as described herein, and which may in certain distinct but related embodiments also include other compounds that are known in the art such as one or more antibiotic compounds as described herein. BT compounds and methods for making them are disclosed herein and are also disclosed, for example, in Domenico et al. (1997 *Antimicrob. Agent. Chemother.* 41(8):1697-1703; 2001 *Antimicrob. Agent. Chemother.* 45(5) 1417-1421) and in U.S. RE37,793, U.S. Pat. No. 6,248,371, U.S. Pat. No. 6,086,921, and U.S. Pat. No. 6,380,248. As also noted above, certain preferred BT compounds are those that contain bismuth or a bismuth salt ionically bonded to, or in a coordination complex with, a thiol-containing compound, such as a composition that comprises bismuth chelated to the thiol-containing compound, and certain other preferred BT compounds are those that contain bismuth or a bismuth salt in covalent bond linkage to the thiol-containing compound. Also preferred are substantially monodisperse microparticulate BT compositions as described herein. Neither from previous efforts to treat bacterial infections, nor from previous characterization in other contexts of any compounds described herein for the first time as having use in compositions and methods for promoting the herein described treatment of natural surfaces, could it be predicted that the present methods of using such compounds would have the herein described beneficial effects.

According to preferred embodiments there are thus provided methods for treating a natural surface, comprising administering to the surface at least one microparticulate BT compound as described herein. In certain embodiments the method further comprises administering, simultaneously or sequentially and in either order, at least one antibiotic compound, which in certain preferred embodiments may be a synergizing antibiotic as described herein, and which in certain other preferred embodiments may be an enhancing antibiotic as described herein. The antibiotic compound may be an aminoglycoside antibiotic, a carbapenem antibiotic, a cephalosporin antibiotic, a fluoroquinolone antibiotic, a glycopeptides antibiotic, a lincosamide antibiotic, a penicillinase-resistant penicillin antibiotic, or an aminopenicillin antibiotic. Clinically useful antibiotics are discussed elsewhere herein and are also described in, e.g., Washington University School of Medicine, *The Washington Manual of Medical Therapeutics* ($32^{nd}$ Ed.), 2007 Lippincott, Williams and Wilkins, Philadelphia, Pa.; and in Hauser, A L, *Antibiotic Basics for Clinicians,* 2007 Lippincott, Williams and Wilkins, Philadelphia, Pa.

As described herein, certain embodiments derive from the unpredictable discovery that for a bacterial infection that comprises gram positive bacteria, a preferred therapeutically effective formulation may comprise a BT compound (e.g., BisEDT, bismuth:1,2-ethanedithiol; BisPyr, bismuth:pyrithione; BisEDT/Pyr, bismuth:1,2-ethanedithiol/pyrithione) and rifamycin, or a BT compound and daptomycin (sold under the trademark CUBICIN®, Cubist Pharmaceuticals, Lexington, Mass.), or a BT compound and linezolid (sold under the trademark ZYVOX®, Pfizer, Inc., NY, NY), or a BT compound (e.g., BisEDT, bismuth:1,2-ethanedithiol; BisPyr, bismuth:pyrithione; BisEDT/Pyr, bismuth:1,2-ethanedithiol/pyrithione) and one or more of ampicillin, cefazolin, cefepime, chloramphenicol, clindamycin (or another lincosamide antibiotic), daptomycin (CUBICIN®), doxycycline, gatifloxacin, gentamicin, imipenim, levofloxacin, linezolid (ZYVOX®), nafcilin, paromomycin, rifampin, sulphamethoxazole, tobramycin and vancomycin.

As also described herein, certain embodiments derive from the unpredictable discovery that for a bacterial infection that comprises gram negative bacteria, a preferred therapeutically effective formulation may comprise a BT compound and amikacin. Certain related embodiments contemplate treatment of an infection comprising gram negative bacteria with a BT compound and another antibiotic, such as another aminoglycoside antibiotic, which in certain embodiments is not gentamicin or tobramycin. Accordingly and in view of these embodiments, other related embodiments contemplate identifying one or more bacterial populations or subpopulations in or on a natural surface by the well known criterion of being gram positive or gram negative, according to methodologies that are familiar to those skilled in the medical microbiology art, as a step for selecting appropriate antibiotic compound(s) to include in a formulation to be administered according to the present methods.

The presently described compositions and methods may find use in the treatment of microbes (e.g., bacteria, viruses, yeast, molds and other fungi, microbial parasites, etc.) in a wide variety of contexts, typically by application or administration of the herein described compounds (e.g., one or more microparticulate BTs alone or in combination with one or more synergizing and/or enhancing antibiotics as disclosed herein) to a microbial site such as a microbial presence on or in a natural surface. Such natural surfaces include but are not limited to mammalian tissues (e.g., epithelia including skin, scalp, gastrointestinal tract lining, buccal cavity, etc.; endothelia, cell and tissue membranes such as peritoneal membrane, pericardial membrane, pleural membrane, periosteal membrane, meningeal membranes, sarcolemal membranes, and the like; cornea, sclera, mucous membranes, etc.; and other mammalian tissues such as teeth, bone, joint, tendon, ligament, muscle, heart, lung, kidney, liver, spleen, gall bladder, pancreas, bladder, nerve, etc.).

The microparticulate antimicrobial agents described herein may be used to suppress microbial growth, reduce microbial infestation, reduce biofilm, prevent conversion of bacteria to biofilm, prevent or inhibit microbial infection and any other use described herein. These agents are also useful for a number of antiviral purposes, including prevention or inhibition of viral infection by herpes family viruses such as cytomegalovirus, herpes simplex virus Type 1, and herpes simplex virus Type 2, and/or infection by other viruses. In this regard, the agents are useful for the prevention or inhibition of viral infection by a variety of viruses, such as, single stranded RNA viruses, single stranded DNA viruses, Rous sarcoma virus (RSV), hepatitis A virus, hepatitis B virus (HBV), Hepatitis C(HCV), Influenza viruses, west nile virus (WNV), Epstein-Barr virus (EBV), eastern equine encephalitis virus (EEEV), severe acute respiratory virus (SARS), human immunodeficiency virus (HIV), human papilloma virus (HPV), and human T cell lymphoma virus (HTLV).

Other internal and external pharmaceutical uses of the herein described antimicrobial agents include, but are not limited to, treatment or prevention of bacterial infection, of tuberculosis, of fungal infections such as yeast and mold infections (for example, *Candida* (e.g., *Candida albicans, Candida glabrata, C. parapsilosis, C. tropicalis*, and *C. dubliniensis*) or *Cryptococcus* or other fungi), of *Helicobacter pylori* infection, and of peptic ulcer disease. In one embodiment, the agent is used at a dosage not generally lethal to bacteria but which is nonetheless sufficient to reduce protective polysaccharide coatings that would otherwise resist natural immune response. This technique is thus believed to aid immune system-mediated eradication of bacterial infection without harming human symbiotic microorganisms (e.g., normal intestinal flora and the like) to the extent that may be the case with antibiotics.

By way of illustration and not limitation, certain contemplated embodiments are now described.

In certain embodiments, a microparticulate BT compound described herein (or composition comprising the microparticulate BT compound) may be combined with at least one or more anti-biofilm agents for controlling biofilm development, disrupting a biofilm, or reducing the amount of biofilm. As understood in the art, interspecies quorum sensing is related to biofilm formation. Certain agents that increase LuxS-dependent pathway or interspecies quorum sensing signal (see, e.g., U.S. Pat. No. 7,427,408) contribute to controlling development and/or proliferation of a biofilm. Exemplary agents include, by way of example, N-(3-oxododecanoyl)-L-homoserine lactone (OdDHL) blocking compounds and N-butyryl-L-homoserine lactone (BHL) analogs, either in combination or separately (see, e.g., U.S. Pat. No. 6,455,031). An oral hygiene composition comprising a microparticulate BT compound and at least one anti-biofilm agent can be delivered locally for disruption and inhibition of bacterial biofilm and for treatment of periodontal disease (see, e.g., U.S. Pat. No. 6,726,898).

Compositions Comprising Microparticulate Bismuth-Thiols and Uses for Oral Hygiene and for Treating Inflammation and Infection of the Mouth.

In another embodiment, compositions comprising microparticulate BT compounds are formulated for oral use and may be used in methods for preventing or reducing microbial growth in the mouth and for preventing and/or treating microbial infections and inflammation of the oral cavity. These compositions are therefore useful for preventing or treating (i.e., reducing or inhibiting development of, reducing the likelihood of occurrence or recurrence of) dental plaque, halitosis, periodontal disease, gingivitis, and other infections of the mouth. The oral compositions comprising microparticulate BT compound may also be useful for preventing and/or controlling (i.e., slowing, retarding, inhibiting) biofilm development, disrupting a biofilm, or reducing the amount of biofilm present on an oral surface, particularly a tooth or gums.

Trapped food particles, poor oral hygiene and poor oral health, and improper cleaning of dentures can promote microbial growth between teeth, around the gums, and on the tongue. Continued microbial growth and the presence of dental caries may result in halitosis, dental plaque (i.e., a biofilm formed by colonization of microorganisms), gingivitis, and inflammation. In the absence of proper oral care (e.g., tooth brushing, flossing), more serious infections, such as periodontal disease and infections of the jaw, may ensue.

Good oral hygiene is important not only for oral health, but for prevention of several chronic conditions. Controlling bacterial growth in the mouth may help lower risk of heart disease, preserve memory, and reduce the risk of infection and inflammation in other areas of the body. People with diabetes are at greater risk for developing severe gum problems, and reducing the risk of gingivitis by maintaining good oral health may help control blood sugar. Pregnant women may be more likely to experience gingivitis, and some research suggests a relationship between gum disease in pregnant women and delivery of preterm, low-birth-weight infants.

Bacteria are the primary etiologic agents in periodontal disease. More than 500 bacterial strains may be found in dental plaque (Kroes et al., *Proc. Natl. Acad. Sci. USA* 96:14547-52 (1999)). Bacteria have evolved to survive in the environment of the tooth surface, gingival epithelium, and oral cavity as biofilms, which contributes to the difficulty in treating periodontitis. Bactericidal agents as well as antibiotics that are currently used to treat such infections often do not kill all of offending organisms. Use of an agent that is ineffective against certain bacteria species may result in proliferation of resistant bacterial species. Moreover, these agents may cause unpleasant side effects, such allergic reactions, inflammation, and tooth discoloration.

Dental bacterial plaque is a biofilm that adheres tenaciously to tooth surfaces, restorations, and prosthetic appliances. The primary means to control biofilms in the mouth is through mechanical cleaning (i.e., tootbrushing, flossing, etc.). Within the first two days after which no such cleaning has been undertaken, the tooth's surface is colonized predominantly by gram-positive facultative cocci, which are primarily streptococci species. The bacteria excrete an extracellular slime layer that helps anchor the bacteria to the surface and provides protection for the attached bacteria. Microcolony formation begins once the surface of the tooth has been covered with attached bacteria. The biofilm grows primarily through cell division of adherent bacteria, rather than through the attachment of new bacteria. Doubling times of bacteria forming plaque are rapid in early development and slower in more mature biofilms.

Coaggregation occurs when bacterial colonizers subsequently adhere to bacteria already attached to the pellicle. The result of coaggregation is the formation of a complex array of different bacteria linked to one another. After a few days of undisturbed plaque formation, the gingival margin becomes inflamed and swollen. Inflammation may result in creation of a deepened gingival sulcus. The biofilm extends into this subgingival region and flourishes in this protected environment, resulting in the formation of a mature subgingival plaque biofilm. Gingival inflammation does not appear until the biofilm changes from one composed largely of gram-positive bacteria to one containing gram-negative anaerobes. A subgingival bacterial microcolony, composed predominantly of gram-negative anaerobic bacteria, becomes established in the gingival sulcus between 3 and 12 weeks after the beginning of supragingival plaque formation. Most bacterial species currently suspected of being periodontal pathogens are anaerobic, gram-negative bacteria.

Bacterial microcolonies protected within the biofilm are typically resistant to antibiotics (administered systemically), antiseptics or disinfectants (administered locally), and immune defenses. Antibiotic doses that kill free-floating bacteria, for example, need to be increased as much as 1,500 times to kill biofilm bacteria. At this high concentration, these antimicrobials tend to be toxic to the patient as well (see, e.g., Coghlan 1996, *New Scientist* 2045:32-6; Elder et al., 1995, *Eye* 9:102-9).

Diligent and frequent physical removal of bacterial plaque biofilms is the most effective means of eliminating and controlling plaque. However, subgingival plaque within pockets cannot be reached by brushes, floss, or oral rinses. Therefore, frequent periodontal debridement of subgingival root surfaces by a dental hygienist or dentist is an essential component in prevention and treatment of periodontitis.

In certain embodiments, a microparticulate BT compound may be incorporated into oral hygiene compositions, such as but not limited to, toothpaste, mouthwash (i.e., mouth rinse), oral gels, dentifrice powders, oral sprays (including a spray dispersed by an oral inhaler), edible film, chewing gum, oral slurry, denture liquid cleaners, denture storage liquids, and dental floss, which may be routinely used by any subject. A microparticulate BT compound may be incorporated into oral hygiene compositions that are used primarily by dental care professions, including for example, fluoride liquid treatments, cleaning compositions, buffing compositions, oral rinses, and dental floss. The present embodiments contemplate replacement of antimicrobials formulated with oral hygiene compositions, which are described in the art, with the presently described microparticulate BT compounds to provide the advantages disclosed herein, including the range of antimicrobial activities, solubility and bioavailability, antibiofilm effects, non-toxicity, enhancement of antibiotic efficacies, and other properties as described herein.

A microparticulate BT compound may also be used for preventing or treating caries and/or inflammation (i.e., reducing the likelihood of occurrence or recurrence of caries and/or inflammation, respectively) by administering the microparticulate BT compound to the surface of the teeth. A composition comprising a microparticulate BT compound may be a mucoadhesive composition that is applied to the surface of a tooth and/or gum or oral mucous membrane may be in any form that adheres to some extent to a surface or that delivers a pharmaceutically effective amount of the active ingredient(s) to the desired surface. A microparticulate BT compound can also be formulated to release slowly from the composition applied to the tooth. For example, the composition may be a gel (e.g., a hydrogel, thiomer, aerogel, or organogel) or liquid. An organogel may comprise an organic solvent, lipoic acid, vegetable oil, or mineral oil. Such gel or liquid coating formulations may be applied interior or exterior to an amalgam or composite or other restorative composition. A slow-release composition may deliver a pharmaceutically effective amount of microparticulate BT compound for 1, 2, 3, 4, 5, 6, or 7 (a week) days or for 2, 3, 4, 5, 6, 7 weeks, or 1, 2, 3, 4, 5, or 6 months. Such compositions can be prepared by a person skilled in the art using any number of methods known in the art.

In certain other embodiments, and as described herein, antimicrobial compositions are provided for oral use that comprise microparticulate BT compound and one or more additional antimicrobial compounds or agents. Particularly useful are the compositions comprising s and a second antimicrobial agent that when administered in combination have enhanced or synergistic antimicrobial effects, as described herein. By way of example, an enhanced antimicrobial effect may be observed when a microparticulate BT compound is administered together with an antimicrobial agent that chelates iron. In other particular embodiments, a microparticulate BT compound is formulated with an anti-inflammatory agent, compound, small molecule, or macromolecule (such as a peptide or polypeptide).

Any of the microparticulate BT compounds described herein may be formulated for oral use. In certain embodiments, microparticulate BT compounds that are prepared with hydrophobic thiols (e.g., thiochlorophenol) may be used and which may exhibit greater capability than less hydrophobic BT compounds to adhere to teeth and tissues of the mouth. BT compounds that have a net negative charge, such as those having a 1:2 molar ratio (bismuth to thiol) may also have favorable adhesive properties.

The oral hygiene compositions comprising a microparticulate BT compound may further comprise one or more active ingredients and/or one or more orally suitable excipients or carriers. In one embodiment, the oral hygiene compositions may further comprise baking soda or another alkaline compound or substance. Because of the chemical and physical properties of baking soda, it has wide range of applications, including cleaning, deodorizing, and buffering. Baking soda neutralizes odors chemically, rather than masking or absorbing them. Baking soda can be combined with a microparticulate BT compound either as a mixture of powders, or dissolved or suspended in any one of the dentifrice powders, gels, pastes, and liquids described herein. In other embodiments, a microparticulate BT compound can be combined with other alkali metal bicarbonate or carbonate substances (e.g., potassium bicarbonate or calcium carbonate) that help maintain a desired alkaline pH and that also possess cleansing and deodorizing properties.

Oral hygiene compositions comprising a microparticulate BT compound may further comprise one or more of the following ingredients. Antimicrobial agents: for example, chlorhexidine; sanguinarine extract; metronidazole; quaternary ammonium compounds (such as cetylpyridinium chloride); bis-guanides (e.g., chlorhexidine digluconate, hexetidine, octenidine, alexidine); halogenated bisphenolic compounds (e.g., 2,2' methylenebis-(4-chloro-6-bromophenol) or other phenolic antibacterial compounds; alkylhydroxybenzoate; cationic antimicrobial peptides; aminoglycosides; quinolones; lincosamides; penicillins; cephalosporins, macrolides; tetracyclines; other antibiotics known in the art; *Coleus forskohlii* essential oil; silver or colloidal silver antimicrobials; tin- or copper-based antimicrobials; Manuka oil; oregano; thyme; rosemary; or other herbal extracts; and grapefruit seed extract. Anti-inflammatory or antioxidant agents: for example, ibuprofen, flurbiprofen, aspirin, indomethacin, aloe vera, turmeric, olive leaf extract, cloves, panthenol, retinol, omega-3 fatty acids, gamma-linolenic acid (GLA), green tea, ginger, grape seed, etc. Anti-caries agents: for example, sodium- and stannous fluoride, aminefluorides, sodium monofluorophosphate, sodium trimetaphosphate, zinc citrate or other zinc agents, and casein. Plaque buffers: for example, urea, calcium lactate, calcium glycerophosphate, and strontium polyacrylates. Vitamins: for example, Vitamins A, C and E. Plant extracts. Desensitizing agents: for example, potassium citrate, potassium chloride, potassium tartrate, potassium bicarbonate, potassium oxalate, potassium nitrate, and strontium salts. Anti-calculus agents: for example, alkali-metal pyrophosphates, hypophosphite-containing polymers, organic phosphonates and phosphocitrates etc. Biomolecules: for example, bacteriocins, bacteriophages, antibodies, enzymes, etc. Flavors: for example, peppermint and spearmint oils, fennel, cinnamon, etc. Proteinaceous materials: for example, collagen. Preservatives. Opacifying agents. Coloring agents. pH-adjusting agents. Sweetening agents. Pharmaceutically acceptable carriers: for example, starch, sucrose, water or water/alcohol systems etc. Surfactants: for example, anionic, nonionic, cationic and zwitterionic or amphoteric surfactants, saponins from plant materials (see, e.g., U.S. Pat. No. 6,485,711). Particulate abrasive materials: for example, silicas, aluminas, calcium carbonates, dicalcium phosphates, calcium pyrophosphates, hydroxyapatites, trimetaphosphates, insoluble hexametaphosphates, agglomerated particulate abrasive materials, chalk, fine ground natural chalk and the like. Humectants: for example, glycerol, sorbitol, propyleneglycol, xylitol, lactitol etc. Binders and thickeners: for example, sodium carboxy methyl cellulose, hydroxyethyl cellulose (sold under the trademark NATROSOL®), xanthan gum, gum arabic, synthetic polymers (e.g., polyacrylates and carboxyvinyl polymers such as polyacrylate rheology modifiers sold under the trademark CARBOPOL® by the Lubrizol Corporation). Polymeric compounds that enhance the delivery of active ingredients such as antimicrobial agents. Buffers and salts to buffer the pH and ionic strength of the oral care composition. Bleaching agents: for example, peroxy compounds (e.g., potassium peroxydiphosphate). Effervescing systems: for example, sodium bicarbonate/citric acid systems. Color change systems. In particular embodiments, an abrasive is silica or fine ground natural chalk.

The oral hygiene compositions comprising a microparticulate BT compound that are formulated for use as a toothpaste may further comprise a humectant (for example, glycerol or sorbitol), a surface-active agent, binding agent, and/or a flavoring agent. The toothpastes may also include a sweetening agent, whitening agent, preservative, and antimicrobial agent. The pH of a toothpaste and other compositions for oral use is typically between pH 5.5 and 8.5. In certain embodiments, oral hygiene compositions, including toothpaste, have a pH between 7 and 7.5, between 7.5 and 8, between 8 and 8.5, or between 8.5 and 9, which may enhance the antimicrobial activity of the microparticulate BT compound. The toothpaste compositions described herein may include one or more of chalk, dicalcium phosphate dihydrate, sorbitol, water, hydrated aluminum oxide, precipitated silica, sodium lauryl sulfate, sodium carboxymethyl cellulose, flavoring, sorbitan monooleate, sodium saccharin, tetrasodium pyrophosphate, methyl paraben, propyl paraben. One or more coloring agents, for example, FD&C Blue, can be employed if desired. Other suitable ingredients that may be including in a toothpaste formulation are described in the art, for example, in U.S. Pat. No. 5,560,517.

In one particular embodiment, the oral hygiene composition is a mouthspray and comprises a microparticulate BT compound, an alkaline buffer (e.g., potassium bicarbonate), an alcohol, a sweetener component, and a flavor system. The flavor system may also have or more of the following: a flavorant, a humectant, a surfactant, a sweetener, and a colorant agent (see, e.g., U.S. Pat. No. 6,579,513). Surfactants described herein and known in the art for use in oral hygiene compositions may be anionic, nonionic, or amphoteric.

In another embodiment, the microparticulate BT-containing oral hygiene composition may be combined with additional active ingredients such as taurolidine and taurultam, which have been described in the art as useful for including in toothpastes, tooth gels, and mouthwashes for treating treat serious infections (see, e.g., United Kingdom Patent Application No., GB 1557163, U.S. Pat. No. 6,488,912). As described herein, microparticulate BT can also be combined with one or more additional antimicrobial agents that when combined with microparticulate BT, the combination has additive or synergistic effects.

In yet another particular embodiment, an oral hygiene composition described herein may further comprise at least one or more anti-biofilm agents for controlling biofilm development, disrupting a biofilm, or reducing the amount of biofilm. As understood in the art, interspecies quorum sensing is related to biofilm formation. Certain agents that increase LuxS-dependent pathway or interspecies quorum sensing signal (see, e.g., U.S. Pat. No. 7,427,408) contribute to controlling development and/or proliferation of a biofilm. Exemplary agents include, by way of example, N-(3-oxododecanoyl)-L-homoserine lactone (OdDHL) blocking compounds and N-butyryl-L-homoserine lactone (BHL) analogs, either in combination or separately (see, e.g., U.S. Pat. No. 6,455,031). An oral hygiene composition comprising a microparticulate BT compound and at least one anti-biofilm agent can be delivered locally for disruption and inhibition of bacterial biofilm and for treatment of periodontal disease (see, e.g., U.S. Pat. No. 6,726,898).

An oral hygiene composition described herein may contain a sufficient amount of a microparticulate BT compound that effects substantial antimicrobial action during the time required for a normal tooth brushing, mouth rinsing, or flossing. As described herein a microparticulate BT compound may be retained on oral surfaces (such as tooth, amalgam, composite, mucous membrane, gums). A microparticulate BT compound retained on the teeth and gums after completion of brushing, rinsing, flossing, for example, may continue to provide extended anti-biofilm and anti-inflammatory action.

In other embodiments, microparticulate BT compounds are slowly released from muco-adhesive polymers or other agents that contribute to retention of microparticulate BT compound on mucosal and tooth surfaces. Microparticulate BT compounds may be added to stable, viscous, mucoadhesive aqueous compositions, which may also be used for the prevention and treatment of ulcerative, inflammatory, and/or erosive disorders of mucous membranes and/or the delivery of pharmaceutically active compounds to mucosal surfaces for topical treatment or transfer to the systemic circulation (see, e.g., U.S. Pat. No. 7,547,433).

In another embodiment, oral hygiene compositions comprising a microparticulate BT compound further comprise olive oil, which may enhance plaque removal. The use of olive oil in a product intended for oral hygiene, such as a toothpaste, a mouthwash, a spray, oral inhaler, or chewing gum, may contribute to elimination or reduction (a decrease) of bacterial plaque and/or to elimination or reduction (decrease of) in the numbers of bacteria present in the buccal cavity, thereby achieving a reduction in the occurrence of dental diseases (e.g., tooth decay, periodontal disease) and halitosis (see, e.g., U.S. Pat. No. 7,074,391).

In other embodiments, an oral hygiene composition comprising a microparticulate BT compound may further comprise a mucosal disinfectant preparation for topical application in the mouth. An oral hygiene composition may further comprise an aqueous slurry useful for cleaning the tongue and throat (see, e.g., U.S. Pat. No. 6,861,049). In still another embodiment, an oral hygiene composition comprising a microparticulate BT compound may further comprise at least one mint that is used for preventing (i.e., reducing the likelihood of occurrence) formation of a cavity (dental caries) or reducing the number of cavities. One such mint, containing an arginine bicarbonate calcium carbonate complex and sold under the trademark CAVISTAT® (Ortek Therapeutics, Inc., Roslyn Heights, N.Y.), contains arginine and calcium, which helps neutralize acid pH and promotes adherence of calcium to enamel surfaces. The inclusion of mint in an oral hygiene composition comprising a microparticulate BT compound may thus increase pH and enhance adherence of a microparticulate BT compound to oral surfaces.

Compositions Comprising Microparticulate Bismuth-Thiols Formulated for Orthopedic Use.

In a particular embodiment, methods are provided for using compositions comprising a microparticulate BT compound for preventing and/or treating microbial infections and inflammation resulting from an orthopedic procedure (e.g., orthopedic surgery, orthopedic therapy, arthroplasty (including two-step arthroplasty), orthodontic therapy). The compositions comprising microparticulate BT compounds as described herein are therefore useful for preventing and/or treating (i.e., reducing or inhibiting development of, reducing the likelihood of occurrence or recurrence of) microbial infections of the skeleton and supporting structure (i.e., bones, joints, muscles, ligaments, tendons) such as osteomyelitis. The compositions described herein comprising a microparticulate BT compound may also be useful for preventing and/or controlling (i.e., slowing, retarding, inhibiting) biofilm development, disrupting a biofilm, or reducing the amount of biofilm present in a joint or on the surface of a bone, ligament, tendon, or tooth.

The compositions described herein for orthopedic use that comprise a microparticulate BT compound may further comprise one or more additional antimicrobial compounds or agents. Particularly useful are the compositions comprising a microparticulate BT compound and a second antimicrobial agent that when administered in combination have enhanced or synergistic antimicrobial effects, as described herein. By way of an additional example, an enhanced antimicrobial effect may be observed when a microparticulate BT compound is administered together with an antimicrobial agent that chelates iron. In other particular embodiments, a microparticulate BT compound is formulated with an anti-inflammatory agent, compound, small molecule, or macromolecule (such as a peptide or polypeptide).

Compositions comprising a microparticulate BT compound may be combined with at least one other antimicrobial agent (i.e., a second, third, fourth, etc. antimicrobial agent) that when administered in combination have enhanced or synergistic antimicrobial effects (i.e., greater than an additive effect). By way of example, an enhanced antimicrobial effect may be observed when a microparticulate BT compound is administered together with an antimicrobial agent that chelates iron. In particular embodiments, compositions comprising a microparticulate BT compound may be combined with at least one other antimicrobial agent and/or anti-inflammatory agent selected from the following: Antimicrobial agents: for example, chlorhexidine; sanguinarine extract; metronidazole; quaternary ammonium compounds (such as cetylpyridinium chloride); bis-guanides (e.g., chlorhexidine digluconate, hexetidine, octenidine, alexidine); halogenated bisphenolic compounds (e.g., 2,2' methylenebis-(4-chloro-6-bromophenol) or other phenolic antibacterial compounds; alkylhydroxybenzoate; cationic antimicrobial peptides; aminoglycosides; quinolones; lincosamides; penicillins; cephalosporins, macrolides; tetracyclines; other antibiotics known in the art; *Coleus forskohlii* essential oil; silver or colloidal silver antimicrobials; tin- or copper-based antimicrobials; Manuka oil; oregano; thyme; rosemary; or other herbal extracts; and grapefruit seed extract. Anti-inflammatory or antioxidant agents: for example, ibuprofen, flurbiprofen, aspirin, indomethacin, aloe vera, turmeric, olive leaf extract, cloves, panthenol, retinol, omega-3 fatty acids, gamma-linolenic acid (GLA), green tea, ginger, grape seed, etc. In particular embodiments, the compositions comprising microparticulate BT compound may further comprise an antibiotic selected from clindamycin, vancomycin, daptomycin, cefazolin, gentamicin, tobramycin, metronidazole, cefaclor, ciprofloxacin, or other antimicrobial such as a quaternary ammonium compound (e.g., benzalkonium chloride, cetyl pyridinium chloride), an anti-microbial zeolite, alkali metal hydroxide, or an alkaline earth metal oxide. The compositions may optionally comprise one or more pharmaceutically suitable carriers (i.e., excipients), surfactants, buffers, diluents, and salts, and bleaching agents, which are described herein. Accordingly, these and certain of the related herein disclosed embodiments contemplate inclusion in such products and processes of the presently disclosed microparticulate BT compositions, which may include one or more microparticulate BT, and which may also optionally further include an antibiotic such as a synergizing or an enhancing antibiotic as described herein.

Biological, Biomedical and Other Uses for Microparticulate BTs.

Certain other embodiments contemplate use of the herein described microparticulate BTs, whether as individual BTs or BTs in which the bismuth moiety is replaced with a different Group V metal such as antimony (Sb) or arsenic (As), and/or as such BTs in combination with one or more antibiotic with which, as described herein, the BT exhibits synergizing or enhanced antimicrobial activity, in orally ingested nutritional formulations.

According to non-limiting theory, the inclusion of microparticulate BTs in such formulations along with other components such as vitamins, minerals, amino acids, hydrocarbons including carbohydrates, fatty acids, oils, phytonutrients, teas, herbs or herbal extracts, and/or other nutritional or food products, may in certain embodiments result in the blockage or retardation of nutrient uptake by microbial populations in the gastrointestinal tract, in a manner that promotes increased (e.g., in a statistically significant manner relative to an appropriate control) bioavailability of the BT and optionally the antibiotic and/or of the additional nutritional component(s) to the host digestive tract. In certain other embodiments, by varying the particular vitamins, minerals, amino acids, hydrocarbons including carbohydrates, fatty acids, oils, phytonutrients, teas, herbs or herbal extracts, and/or other nutritional or food products that are included in the oral microparticulate BT (or AsT or SbT) formulation, bioavailability of the BT and optionally of the antibiotic and/or of the additional nutritional component(s) to the host digestive tract may be decreased (e.g., in a statistically significant manner relative to an appropriate control).

For instance, it may be desirable when a pathologic gastrointestinal (GI) tract infection is present to administer a microparticulate BT formulation that discourages intestinal absorption of the BT compounds so that they remain bioavailable within the GI tract in order to exert antimicrobial effects against the infectious pathogens. Those familiar with the art will be aware of a number of vitamins, minerals, amino acids, hydrocarbons including carbohydrates, fatty acids, oils, phytonutrients, teas, herbs and/or herbal extracts that promote or discourage GI tract absorption of nutrients, such that formulations for increasing or decreasing the GI tract presence of one or more components (e.g., the microparticulate BT compound, the antibiotic, or one or more particular nutrients) may be prepared using the presently disclosed microparticulate BTs (or AsT or SbT).

Certain other embodiments provided herein contemplate inclusion of the presently disclosed microparticulate BT compounds in compositions for oral delivery to reduce fecal or digestive gas odors, for instance in patients who have undergone colostomy, and in other compositions for topical delivery to reduce underarm, foot or other body odors associated with topical microbial presence. A number of skin and GI tract microbial populations, including planktonic and biofilm bacteria, are susceptible to low concentrations of the herein described microparticulate BT compounds, including such BT compounds when present with enhancing or synergizing antibiotics as described herein.

Accordingly, certain embodiments contemplate orally delivered and topically delivered microparticulate BT formulations to decrease (e.g., in a statistically significant manner relative to an appropriate control) populations of GI-resident or skin-resident bacteria in a manner that reduces or alleviates the problem of unwanted odor. Oral and topical pharmaceutical formulations are described below, such that these and related embodiments offer advantages associated with the present microparticulate formulation of BT, such as compatible bioavailability and solubility properties and low toxicity; other factors that may influence the selection of antimicrobial compositions are described elsewhere herein and may also be found, e.g., in U.S. Pat. No. 6,582,719.

An exemplary BT compound, BisEDT, has been applied (50 uL of a 1 mg/mL solution in DMSO) to the axillary area in human test subjects and shown to neutralize body odors for two to three days. A mixture of BisEDT in talcum powder applied to the feet of a human test subject substantially reduced foot odor. Laboratory mice fed 1 mg/kg BisEDT orally twice daily for five days exhibited 90% reductions in the number of fecal flora. Related embodiments also contemplate a generally useful deodorant for any thiol-containing solution that emits odors (e.g., fish oils such as salmon oil), comprising a microparticulate BT preparation as described herein that is made with an excess of bismuth, and that can be added to the thiol-containing solution as an odor quenching agent. The resulting mixture retains the antimicrobial properties of the microparticulate BT. Other contemplated applications include solvents such as other biological source oils or butters, for instance, hemp oil, tea tree oil, shea butter, flax seed oil, fish oils, and in certain embodiments such oils as may have an independent or synergistic anti-inflammatory and/or pain-reducing and/or other beneficial physiologic effect.

Pharmaceutical Compositions and Administration

Certain embodiments also relate to a pharmaceutical composition containing the microparticulate BT compounds disclosed herein; in certain such embodiments the pharmaceutical composition may further comprise one or more antibiotics such as an antibiotic with which the BT compound exhibits a synergizing or enhancing effect as described herein. In one embodiment, there is provided a composition comprising one or more such microparticulate BT compounds in a pharmaceutically acceptable carrier, excipient or diluent and in a therapeutic amount, as disclosed herein, when administered to an animal, preferably a mammal, most preferably a human patient.

Administration of the microparticulate BT compounds, or their pharmaceutically acceptable salts, in pure form or in an appropriate pharmaceutical composition, can be carried out via any of the accepted modes of administration of agents for serving similar utilities. The pharmaceutical compositions can be prepared by combining a microparticulate BT compound with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, rectal, vaginal, and intranasal. The term parenteral as used herein includes subcutaneous injections, intravenous, intramuscular, intrasternal injection or infusion techniques. Pharmaceutical compositions are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound in aerosol form may hold a plurality of dosage units. Actual methods of preparing such dosage forms are known, or will be apparent, to those skilled in this art; for example, see *The Science and Practice of Pharmacy,* 20th Edition (Philadelphia College of Pharmacy and Science, 2000). The composition to be administered will, in any event, contain a therapeutically effective amount of a compound, or a pharmaceutically acceptable salt thereof, for treatment of a disease or condition of interest in accordance with the teachings herein.

The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids, such as water, saline, glycerol and ethanol, and the like. A thorough discussion of pharmaceutically acceptable carriers, diluents, and other excipients is presented in REMINGTON'S PHARMACEUTICAL SCIENCES (Mack Pub. Co., N.J. current edition).

A pharmaceutical composition may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, sodium starch glycolate sold under the trademark PRIMOGEL™ (DMV International), corn starch and the like; lubricants such as magnesium stearate or vegetable stearine sold under the trademark STEROTEX® (Abitec Corp.); glidants such as colloidal silicon dioxide; sweetening agents such as honey, sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition intended for either parenteral or oral administration should contain an amount of a microparticulate BT compound such that a suitable dosage will be obtained. Typically, this amount is at least 0.01% of a microparticulate BT compound in the composition. When intended for oral administration, this amount may be varied to be between 0.1 and about 70% of the weight of the composition. Preferred oral pharmaceutical compositions contain between about 4% and about 50% of the BT compound. Preferred pharmaceutical compositions and preparations according to the present invention are prepared so that a parenteral dosage unit contains between 0.01 to 10% by weight of the microparticulate BT compound prior to dilution.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, bee wax, mineral oil, shea butter, tea tree oil, flax seed oil, hemp oil or other plant or vegetable oils including those known to have anti-inflammatory and/or anti-pain or other beneficial effects, salmon oil or other fish oils including those known to have anti-inflammatory and/or anti-pain or other beneficial effects, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the microparticulate BT compound from about 0.1 to about 10% w/v (weight per unit volume).

The pharmaceutical composition may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition in solid or liquid form may include an agent that binds to the microparticulate BT compound and thereby assists in the delivery of the compound. Suitable agents that may act in this capacity include a monoclonal or polyclonal antibody, a protein or a liposome. Certain contemplated embodiments, however, expressly exclude the inclusion of a liposome in the pharmaceutical composition.

The pharmaceutical composition may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of the microparticulate BT compounds may be delivered in single phase, bi-phasic, or tri-phasic systems in order to deliver the active ingredient(s). Delivery of the aerosol includes the necessary container, activators, valves, sub-containers, and the like, which together may form a kit. One skilled in the art, without undue experimentation may determine preferred aerosols.

The pharmaceutical compositions may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The herein described microparticulate BT compounds, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 kg mammal) from about 0.001 mg/kg (i.e., 0.07 mg) to about 100 mg/kg (i.e., 7.0 g); preferably a therapeutically effective dose is (for a 70 kg mammal) from about 0.01 mg/kg (i.e., 7 mg) to about 50 mg/kg (i.e., 3.5 g); more preferably a therapeutically effective dose is (for a 70 kg mammal) from about 1 mg/kg (i.e., 70 mg) to about 25 mg/kg (i.e., 1.75 g).

The ranges of effective doses provided herein are not intended to be limiting and represent preferred dose ranges. However, the most preferred dosage will be tailored to the individual subject, as is understood and determinable by one skilled in the relevant arts. (see, e.g., Berkow et al., eds., The Merck Manual, 16$^{th}$ edition, Merck and Co., Rahway, N.J., 1992; Goodmanetna., eds., Goodman and Cilman's The Pharmacological Basis of Therapeutics, 10$^{th}$ edition, Pergamon Press, Inc., Elmsford, N.Y., (2001); Avery's Drug Treatment: Principles and Practice of Clinical Pharmacology and Therapeutics, 3rd edition, ADIS Press, LTD., Williams and Wilkins, Baltimore, Md. (1987), Ebadi, Pharmacology, Little, Brown and Co., Boston, (1985); Osolci al., eds., Remington's Pharmaceutical Sciences, 18$^{th}$ edition, Mack Publishing Co., Easton, Pa. (1990); Katzung, Basic and Clinical Pharmacology, Appleton and Lange, Norwalk, Conn. (1992)).

The total dose required for each treatment can be administered by multiple doses or in a single dose over the course of the day, if desired. Generally, treatment is initiated with smaller dosages, which are less than the optimum dose of the compound. Thereafter, the dosage is increased by small increments until the optimum effect under the circumstances is reached. The diagnostic pharmaceutical compound or composition can be administered alone or in conjunction with other diagnostics and/or pharmaceuticals directed to the pathology, or directed to other symptoms of the pathology. The recipients of administration of microparticulate BT compounds and/or compositions can be any vertebrate animal, such as mammals. Among mammals, the preferred recipients are mammals of the Orders Primate (including humans, apes and monkeys), Arteriodactyla (including horses, goats, cows, sheep, pigs), Rodenta (including mice, rats, rabbits, and hamsters), and Carnivora (including cats, and dogs). Among birds, the preferred recipients are turkeys, chickens and other members of the same order. The most preferred recipients are humans.

For topical applications, it is preferred to administer an effective amount of a microparticulate BT-containing pharmaceutical composition to a target area, e.g., skin surfaces, mucous membranes, and the like. This amount will generally range from about 0.0001 mg to about 1 g of a BT compound per application, depending upon the area to be treated, whether the use is diagnostic, prophylactic or therapeutic, the severity of the symptoms, and the nature of the topical vehicle employed. A preferred topical preparation is an ointment, wherein about 0.001 to about 50 mg of active ingredient is used per cc of ointment base. The pharmaceutical composition can be formulated as transdermal compositions or transdermal delivery devices ("patches"). Such compositions include, for example, a backing, active compound reservoir, a control membrane, liner and contact adhesive. Such transdermal patches may be used to provide continuous pulsatile, or on demand delivery of the compounds of the present invention as desired.

The microparticulate BT compositions can be formulated so as to provide quick, sustained or delayed release of the active ingredient after administration to the patient by employing procedures known in the art. Controlled release drug delivery systems include osmotic pump systems and dissolutional systems containing polymer-coated reservoirs or drug-polymer matrix formulations. Examples of controlled release systems are given in U.S. Pat. Nos. 3,845,770 and 4,326,525 and in P. J. Kuzma et al, Regional Anesthesia 22 (6): 543-551 (1997), all of which are incorporated herein by reference.

The microparticulate BT compositions can also be delivered through intranasal drug delivery systems for local, systemic, and nose-to-brain medical therapies. Nasal, respiratory and sinus drug delivery technology sold under the trademark CONTROLLED PARTICLE DISPERSION® (Kurve Technology, Inc.) (CPD)™, traditional nasal spray bottles, inhalers or nebulizers are known by those skilled in the art to provide effective local and systemic delivery of drugs by targeting the olfactory region and paranasal sinuses.

The invention also relates in certain embodiments to an intravaginal shell or core drug delivery device suitable for administration to the human or animal female. The device may be comprised of the active pharmaceutical ingredient in a polymer matrix, surrounded by a sheath, and capable of releasing the compound in a substantially zero order pattern on a daily basis similar to devices used to apply testosterone as described in WO 98/50016.

Current methods for ocular delivery include topical administration (eye drops), subconjunctival injections, periocular injections, intravitreal injections, surgical implants and iontophoresis (uses a small electrical current to transportionized drugs into and through body tissues). Those skilled in the art would combine the best suited excipients with the compound for safe and effective intra-occular administration.

The most suitable route will depend on the nature and severity of the condition being treated. Those skilled in the art are also familiar with determining administration methods (oral, intravenous, inhalation, sub-cutaneous, rectal etc.), dosage forms, suitable pharmaceutical excipients and other matters relevant to the delivery of the compounds to a subject in need thereof.

The presently described compositions and methods may also find use in the treatment of acute and chronic wounds and wound biofilms, including, for example, as burn creams, as topicals for the treatment of existing wounds including those described herein, for prevention of chronic wounds, for treatment of MRSA skin infections, and for other related indications as disclosed herein and as will be apparent to the skilled person in view of the present disclosure.

Non-limiting examples of bacteria against which the herein described compositions and methods may find beneficial use, according to certain embodiments as described herein, include *Staphylococcus aureus* (*S. aureus*), MRSA (methicillin-resistant *S. aureus*), *Staphylococcus epidermidis*, MRSE (methicillin-resistant *S. epidermidis*), *Mycobacterium tuberculosis*, *Mycobacterium avium*, *Pseudomonas aeruginosa*, drug-resistant *P. aeruginosa*, *Escherichia coli*, enterotoxigenic *E. coli*, enterohemorrhagic *E. coli*, *Klebsiella pneumoniae*, *Clostridium difficile*, *Heliobacter pylori*, *Legionella pneumophila*, *Enterococcus faecalis*, methicillin-susceptible *Enterococcus faecalis*, *Enterobacter cloacae*, *Salmonella typhimurium*, *Proteus vulgaris*, *Yersinia enterocolitica*, *Vibrio cholera*, *Shigella flexneri*, vancomycin-resistant *Enterococcus* (VRE), *Burkholderia cepacia* complex, *Francisella tularensis*, *Bacillus anthracis*, *Yersinia pestis*, *Pseudomonas aeruginosa*, vancomycin-sensitive and vancomycin-resistant enterococci (e.g., *E. faecalis*, *E. faecium*), methicillin-sensitive and methicillin-resistant staphylococci (e.g., *S. aureus*, *S. epidermidis*) and *Acinetobacter baumannii*, *Staphylococcus haemolyticus*, *Staphylococcus hominis*, *Enterococcus faecium*, *Streptococcus pyogenes*, *Streptococcus agalactiae*, *Bacillus anthracis*, *Klebsiella pneumonia*, *Proteus mirabilis*, *Proteus vulgaris*, *Yersinia enterocolytica*, *Stenotrophomonas maltophilia*, *Streptococcus pneumonia*, penicillin-resistant *Streptococcus pneumonia*, *Burkholderia cepacia*, *Bukholderia multivorans*, *Mycobacterium smegmatis* and *E. cloacae*.

The practice of certain embodiments of the present invention will employ, unless indicated specifically to the contrary, conventional methods of microbiology, molecular biology, biochemistry, cell biology, virology and immunology techniques that are within the skill of the art, and reference to several of which is made below for the purpose of illustration. Such techniques are explained fully in the literature. See, e.g., Sambrook, et al. *Molecular Cloning: A Laboratory Manual* (2nd Edition, 1989); Maniatis et al. *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984).

Unless the context requires otherwise, throughout the present specification and claims, the word "comprise" and variations thereof, such as, "comprises" and "comprising" are to be construed in an open, inclusive sense, that is as "including, but not limited to".

Reference throughout this specification to "one embodiment" or "an embodiment" or "an aspect" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Certain embodiments relate to methods, compositions and kits for treating an acute or chronic wound or a wound biofilm in a subject, which may comprise promoting skin tissue repair in the subject, or for altering one or more cellular wound repair activity in a cell or plurality of cells. A cell generally indicates a single cell, whereas a plurality of cells indicates more than one cell. The cells may comprise a tissue, organ or entire organism. Furthermore, the cell or cells may be located in vivo, in vitro, or ex vivo. Maintaining cell, tissue and organ cultures are routine procedures for one of skill in the art, the conditions and media for which can be easily ascertained. (See, for example, Freshney, *Culture of Animal Cells: A Manual of Basic Technique*, Wiley-Liss 5$^{th}$ Ed. (2005); Davis, *Basic Cell Culture*, Oxford University Press 2$^{nd}$ Ed. (2002)).

As disclosed herein, certain embodiments relate to methods for treating an acute or chronic wound or a wound biofilm in a subject that comprises administering to the subject a therapeutically effective amount of a composition comprising a BT compound as described herein for use in such method (e.g., as provided in the form of a plurality of substantially monodisperse microparticles), and optionally in certain further embodiments also comprising an antibiotic compound as described herein for use in such method, for example, a BT compound such as BisEDT or BisBAL or other compounds presented in Table 1 herein, or any other BT agent such as those described in Domenico et al. (1997 *Antimicrob. Agent. Chemother.* 41:1697; 2001 *Antimicrob. Agent. Chemother.* 45:1421) and/or in U.S. RE37,793, U.S. Pat. No. 6,248,371, U.S. Pat. No. 6,086,921, and U.S. Pat. No. 6,380,248 and/or as prepared according to the methods disclosed herein. Certain other embodiments relate to methods that comprise contacting any natural surface with a composition comprising one or more of the herein described microparticulate BT compounds, where such step of contacting may comprise one or more of directly applying, coating, dipping, irrigating, spraying, painting or otherwise bringing the BT composition into contact with the natural surface.

The step of administering to a subject such as a human or other mammalian subject may be performed by any means known to the art, for example, topically (including via direct administration to skin or to any epithelial tissue surface, including such surfaces as may be present in glandular tissues or in the respiratory and/or gastrointestinal tracts), vaginally, intraperitoneally, orally, parenterally, intravenously, intraarterially, transdermally, sublingually, subcutaneously, intramuscularly, transbuccally, intranasally, via inhalation, intraoccularly, subcutaneously, intraadiposally, intraarticularly or intrathecally.

In preferred embodiments administering may be performed topically, where pharmaceutical excipients or carriers for topical use are described herein and known in the art.

As noted above, certain invention embodiments described herein relate to topical formulations of the described BT compounds (e.g., BisEDT and/or BisBAL), which formulations may in certain further embodiments comprise one or more antibiotic compounds as described herein, for instance, amikacin, ampicillin, cefazolin, cefepime, chloramphenicol, ciprofloxacin, clindamycin (or another lincosamide antibiotic), daptomycin (sold under the trademark CUBICIN®), doxycycline, gatifloxacin, gentamicin, imipenim, levofloxacin, linezolid (sold under the trademark ZYVOX®), minocycline, nafcilin, paromomycin, rifampin, sulphamethoxazole, tobramycin and vancomycin; or a carbapenem antibiotic, a cephalosporin antibiotic, a fluoroquinolone antibiotic, a glycopeptide antibiotic, a lincosamide antibiotic, a penicillinase-resistant penicillin antibiotic, and/or an aminopenicillin antibiotic, and/or an aminoglycoside antibiotic such as amikacin, arbekacin, gentamicin, kanamycin, neomycin, netilmicin, paromomycin, rhodostreptomycin, streptomycin, tobramycin or apramycin, and/or a lipopeptide antibiotic such as daptomycin (CUBICIN®), or an oxazolidinone antibiotic such as linezolid (ZYVOX®). These and related formulations may comprise the BT compound(s) (and optionally one or more antibiotics) in a pharmaceutically acceptable carrier, excipient or diluent and in a therapeutic amount, as disclosed herein, when administered topically to an animal, preferably a mammal, and most preferably a human, and in particularly preferred embodiments, a human having an acute or chronic wound or a wound that contains a bacterial infection which may be biofilm-related (e.g., in which bacteria capable of promoting biofilm formation may be present but a biofilm is not yet detectable) or that contains a bacterial infection such as a biofilm or other bacterial presence.

Topical administration of the BT compounds described herein, or their pharmaceutically acceptable salts, in pure form or in an appropriate pharmaceutical composition, can be carried out via any of the accepted modes of topical administration of agents for serving similar utilities. Topical application or administration of a composition includes, in preferred embodiments, directly contacting the composition (e.g., a topical formulation) with skin and/or another epithelial tissue surface (e.g., respiratory tract, gastrointestinal tract and/or glandular epithelial linings) of the subject undergoing treatment, which may be at one or more localized or widely distributed skin and/or other epithelial tissue surface sites and which may generally refer to contacting the topical formulation with an acute or chronic wound site that is surrounded by intact stratum corneum or epidermis but need not be so limited; for instance, certain embodiments contemplate as a topical application the administration of a topical formulation described herein to injured, abraded or damaged skin, or skin of a subject undergoing surgery, such that contact of the topical formulation may take place not only with stratum corneum or epidermis but also with skin granular cell, spinous cell, and/or basal cell layers, and/or with dermal or underlying tissues, for example, as may accompany certain types of wound repair or wound healing or other skin tissue remodeling.

Such skin tissue repair may therefore comprise, in certain preferred embodiments, dermal wound healing, as may be desirable, for example, in preventing or ameliorating an acute chronic wound or a wound biofilm or, as another example, in preventing or ameliorating skin wound dehiscence, or in improving, accelerating or otherwise enhancing dermal wound healing when an acute or chronic wound and/or skin wound dehiscence may be present. Certain other embodiments that contemplate topical administration to an epithelial tissue surface present in respiratory tract, gastrointestinal tract and/or glandular linings similarly may comprise administration of the topical formulation by an appropriate route as will be known in the art for delivering a topical preparation as provided herein, to one or more epithelial tissue surfaces present in respiratory (e.g., airway, nasopharyngeal and laryngeal paths, tracheal, pulmonary, bronchi, bronchioles, alveoli, etc.) and/or gastrointestinal (e.g., buccal, esophageal, gastric, intestinal, rectal, anal, etc.) tracts, and/or other epithelial surfaces.

According to certain contemplated embodiments topical administration may comprise direct application into an open wound. For instance, an open fracture or other open wound may include a break in the skin that may expose additional underlying tissues to the external environment in a manner that renders them susceptible to microbial infection. Such a situation is not uncommon in certain types of acute traumatic military wounds, including, for example, Type III (severe) open fractures. In accord with these and related embodiments, topical administration may be by direct contact of the herein described BT composition with such damaged skin and/or another epithelial surface and/or with other tissues, such as, for instance, connective tissues including muscle, ligaments, tendons, bones, circulatory tissues such as blood vessels, associated nerve tissues, and any other organs that may be exposed in such open wounds. Examples of other tissues that may be exposed, and hence for which such direct contact is contemplated, include kidney, bladder, liver, pancreas, and any other tissue or organ that may be so detrimentally exposed to opportunistic infection in relation to an open wound.

The topical formulations (e.g., pharmaceutical compositions) may be prepared by combining the described BT compound (e.g., comprising a compound described in U.S. RE37, 793, U.S. Pat. No. 6,248,371, U.S. Pat. No. 6,086,921, and/or U.S. Pat. No. 6,380,248 and/or prepared according to the present disclosure such as the herein described microparticulate BT suspensions), and in certain related embodiments by combining one or more desired antibiotics (e.g., an aminoglycoside antibiotic such as amikacin) separately or together with the BT compound, with an appropriate pharmaceutically acceptable carrier, diluent or excipient for use in a topical formulation preparation, and may be formulated into preparations in solid, semi-solid, gel, cream, colloid, suspension or liquid or other topically applied forms, such as powders, granules, ointments, solutions, washes, gels, pastes, plasters, paints, bioadhesives, microsphere suspensions, and aerosol sprays.

Pharmaceutical compositions of these and related embodiments are formulated so as to allow the active ingredients contained therein, and in particularly preferred embodiments the herein described BT compound(s) alone or in combination with one or more desired antibiotics (e.g., a carbapenem antibiotic, a cephalosporin antibiotic, a fluoroquinolone antibiotic, a glycopeptide antibiotic, a lincosamide antibiotic, a penicillinase-resistant penicillin antibiotic, and an aminopenicillin antibiotic, or an aminoglycoside antibiotic such as amikacin, or rifamycin) which may be applied simultaneously or sequentially and in either order, to be bioavailable upon topical administration of the formulation containing the BT compound(s) and/or antibiotic composition(s) to an acute or chronic wound and optionally to surrounding skin of a subject, such as a mammal, including a human, and in certain preferred embodiments a human patient having an acute or chronic wound, or being at increased risk for having, an acute or chronic wound or a wound biofilm or wound dehiscence (e.g., an obese and/or diabetic individual). Certain embodiments disclosed herein contemplate topical administration of a BT compound and of an antibiotic, including administration that may be simultaneous or sequential and in either order, but the invention is not intended to be so limited and in other embodiments expressly contemplates a distinct route of administration for the BT compound relative to the route of administration of the antibiotic. Thus, the antibiotic may be administered orally, intravenously, or by any other route of administration as described herein, while the BT compound may be administered by a route that is independent of the route used for the antibiotic. As a non-limiting, illustrative example, the BT compound may be administered topically as provided herein, while the antibiotic may be simultaneously or sequentially (and in any order) administered by a distinct route, such as orally, intravenously, transdermally, subcutaneously, intramuscularly and/or by any other route of administration.

The topical formulations described herein deliver a therapeutically effective amount of the antiseptic or wound-healing agent(s) (and optionally the antibiotic(s)) to the wound site, for instance, to skin cells such as dermal fibroblasts. Preferred formulations may be contacted with a desired site such as a topical wound site, a chronic wound, an epithelial tissue surface or other intended site of administration by spraying, irrigating, dipping and/or painting; such formulations therefore may exhibit ready permeability into the skin, as can be determined according to any of a number of established methodologies known to the art for testing the skin permeability of a drug composition (see, e.g., Wagner et al., 2002 *J. Invest. Dermatol.* 118:540, and references cited therein; Bronaugh et al., 1985 *J. Pharm. Sci.* 74:64; Bosman et al., 1998 *J. Pharm. Biomed. Anal.* 17:493-499; Bosman et al., 1996 *J. Pharm Biomed Anal.* 1996 14:1015-23; Bonferoni et al., 1999 *Pharm. Dev. Technol.* 4:45-53; Frantz, Instrumentation and methodology for in vitro skin diffusion cells in methodology for skin absorption. In: Methods for Skin Absorption (Kemppainen & Reifenrath, Eds), CRC Press, Florida, 1990, pp. 35-59; Tojo, Design and calibration of in vitro permeation apparatus. In: Transdermal Controlled Systemic Medications (Chien Y W, Ed), Marcel Dekker, New York, 1987, 127-158; Barry, Methods for studying percutaneous absorption. In: Dermatological Formulations: Percutaneous absorption, Marcel Dekker, New York, 1983, 234-295).

Compositions, and formulations comprising such compositions, that will be administered to the skin of a subject or patient may in certain embodiments take the form of one or more dosage units, where for example, a liquid-filled capsule or ampule may contain a single dosage unit, and a container of a topical formulation as described herein in aerosol form may hold a plurality of dosage units. Actual methods of preparing such dosage forms are known, or will be apparent, to those skilled in this art; for example, see *The Science and Practice of Pharmacy,* 20th Edition (Philadelphia College of Pharmacy and Science, 2000). The composition or formulation to be administered will, in any event, contain a therapeutically effective amount of an antiseptic and/or wound healing-promoting compound as provided herein (e.g., a BT compound), or a pharmaceutically acceptable salt thereof, in accordance with the present teachings.

As noted above, the present topical formulations may take any of a wide variety of forms, and include, for example, creams, lotions, solutions, sprays, gels, ointments, pastes or the like, and/or may be prepared so as to contain liposomes, micelles, and/or microspheres. See, e.g., U.S. Pat. No. 7,205,003. For instance, creams, as is well known in the arts of pharmaceutical and cosmeceutical formulation, are viscous liquids or semisolid emulsions, either oil-in-water or water-in-oil. Cream bases are water-washable, and contain an oil phase, an emulsifier, and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

Lotions, which are preferred for delivery of cosmetic agents, are preparations to be applied to the skin surface without friction, and are typically liquid or semi-liquid preparations in which solid particles, including the active agent, are present in a water or alcohol base. Lotions are usually suspensions of solids, and preferably comprise a liquid oily emulsion of the oil-in-water type. Lotions are preferred formulations herein for treating large body areas, because of the ease of applying a more fluid composition. It is generally preferred that the insoluble matter in a lotion be finely divided. Lotions will typically contain suspending agents to produce better dispersions as well as compounds useful for localizing and holding the active agent in contact with the skin, e.g., methylcellulose, sodium carboxymethyl-cellulose, or the like.

Solutions are homogeneous mixtures prepared by dissolving one or more chemical substances (solutes) in a liquid such that the molecules of the dissolved substance are dispersed among those of the solvent. The solution may contain other pharmaceutically acceptable and/or cosmeceutically acceptable chemicals to buffer, stabilize or preserve the solute. Common examples of solvents used in preparing solutions are ethanol, water, propylene glycol or any other pharmaceutically acceptable and/or cosmeceutically acceptable vehicles.

Gels are semisolid, suspension-type systems. Single-phase gels contain organic macromolecules distributed substantially uniformly throughout the carrier liquid, which is typically aqueous, but also, preferably, contain an alcohol, and, optionally, an oil. Preferred "organic macromolecules," i.e., gelling agents, may be chemically crosslinked polymers such as crosslinked acrylic acid polymers, for instance, the "carbomer" family of polymers, e.g., carboxypolyalkylenes, that may be obtained commercially under the CARBOPOL® trademark. Also preferred in certain embodiments may be hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Ointments, as also well known in the art, are semisolid preparations that are typically based on petrolatum or other petroleum derivatives. The specific ointment base to be used, as will be appreciated by those skilled in the art, is one that will provide for a number of desirable characteristics, e.g., emolliency or the like. As with other carriers or vehicles, an ointment base should be inert, stable, nonirritating, and nonsensitizing. As explained in Remington: The Science and Practice of Pharmacy, 19th Ed. (Easton, Pa.: Mack Publishing Co., 1995), at pages 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearic sulfate, anhydrous lanolin, and hydrophilic petrolatum. Emulsion ointment bases are either water-in-oil (W/O) emulsions or oil-in-water (O/W) emulsions, and include, for example, cetyl alcohol, glyceryl monostearate, lanolin, and stearic acid. Preferred water-soluble ointment bases are prepared from polyethylene glycols of varying molecular weight (see, e.g., Remington, Id.).

Pastes are semisolid dosage forms in which the active agent is suspended in a suitable base. Depending on the nature of the base, pastes are divided between fatty pastes or those made from single-phase aqueous gels. The base in a fatty paste is generally petrolatum or hydrophilic petrolatum or the like. The pastes made from single-phase aqueous gels generally incorporate carboxymethylcellulose or the like as a base.

Formulations may also be prepared with liposomes, micelles, and microspheres. Liposomes are microscopic vesicles having one (unilamellar) or a plurality (multilamellar) of lipid walls comprising a lipid bilayer, and, in the present context, may encapsulate and/or have adsorbed to their lipid membranous surfaces one or more components of the topical formulations herein described, such as the antiseptic, wound healing/skin tissue/epithelial tissue repair-promoting compounds (e.g., microparticulate BT compounds, optionally along with one or more antibiotics) or certain carriers or excipients. Liposomal preparations herein include cationic (positively charged), anionic (negatively charged), and neutral preparations. Cationic liposomes are readily available. For example, N[1-2,3-dioleyloxy)propyl]-N,N,N-triethylammonium (DOTMA) liposomes are available under the tradename LIPOFECTIN® (GIBCO BRL, Grand Island, N.Y.). Similarly, anionic and neutral liposomes are readily available as well, e.g., from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), and dioleoylphoshatidyl ethanolamine (DOPE), among others. These materials can also be mixed with DOTMA in appropriate ratios. Methods for making liposomes using these materials are well known in the art.

Micelles are known in the art as comprised of surfactant molecules arranged so that their polar headgroups form an outer spherical shell, while the hydrophobic, hydrocarbon chains are oriented towards the center of the sphere, forming a core. Micelles form in an aqueous solution containing surfactant at a high enough concentration so that micelles naturally result. Surfactants useful for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltriethylammonium bromide, tetradecyltrimethylammonium bromide, tetradecyltrimethylammonium chloride, dodecylammonium chloride, polyoxyl-8dodecyl ether, polyoxyl-12 dodecyl ether, nonoxynol 10, and nonoxynol 30.

Microspheres, similarly, may be incorporated into the presently described topical formulations. Like liposomes and micelles, microspheres essentially encapsulate one or more components of the present formulations. They are generally, but not necessarily, formed from lipids, preferably charged lipids such as phospholipids. Preparation of lipidic microspheres is well known in the art.

Various additives, as known to those skilled in the art, may also be included in the topical formulations. For example, solvents, including relatively small amounts of alcohol, may be used to solubilize certain formulation components. It may be desirable, for certain topical formulations or in cases of particularly severe skin injury such as a post-surgical acute or chronic wound or post-surgical dermal wound dehiscence, to include in the topical formulation an added skin permeation enhancer in the formulation. Examples of suitable enhancers include, but are not limited to, ethers such as diethylene glycol monoethyl ether (available commercially as sold under the trademark TRANSCUTOL®) and diethylene glycol monomethyl ether; surfactants such as sodium laurate, sodium lauryl sulfate, cetyltrimethylammonium bromide, benzalkonium chloride, polyoxypropylene/polyoxyethylene copolymers known as poloxamers (poloxamer 231, poloxamer 182, poloxamer 184) and sold under the trademark PLURONIC® (BASF Corp.), polysorbate surfactants sold under the trademark TWEEN® (TWEEN® 20, TWEEN® 40, TWEEN® 60, TWEEN® 80), and lecithin (U.S. Pat. No. 4,783,450); alcohols such as ethanol, propanol, octanol, benzyl alcohol, and the like; polyethylene glycol and esters thereof such as polyethylene glycol monolaurate (PEGML; see, e.g., U.S. Pat. No. 4,568,343); amides and other nitrogenous compounds such as urea, dimethylacetamide (DMA), dimethylformamide (DMF), 2-pyrrolidone, 1-methyl-2-pyrrolidone, ethanolamine, diethanolamine, and triethanolamine; terpenes; alkanones; and organic acids, particularly citric acid and succinic acid. The enhancer n-dodecylcaprolactam (laurocapram) sold under the trademark AZONE® and sulfoxides such as DMSO and $C_{10}MSO$ may also be used, but are less preferred.

Most preferred skin permeation enhancers are those lipophilic co-enhancers typically referred to as "plasticizing" enhancers, i.e., enhancers that have a molecular weight in the range of about 150 to 1000 daltons, an aqueous solubility of less than about 1 wt %, preferably less than about 0.5 wt %, and most preferably less than about 0.2 wt %. The Hildebrand solubility parameter of plasticizing enhancers is in the range of about 2.5 to about 10, preferably in the range of about 5 to about 10. Preferred lipophilic enhancers are fatty esters, fatty alcohols, and fatty ethers. Examples of specific and most preferred fatty acid esters include methyl laurate, ethyl oleate, propylene glycol monolaurate, propylene glycerol dilaurate, glycerol monolaurate, glycerol monooleate, isopropyl n-decanoate, and octyldodecyl myristate. Fatty alcohols include, for example, stearyl alcohol and oleyl alcohol, while fatty ethers include compounds wherein a diol or triol, preferably a $C_2$-$C_4$ alkane diol or triol, are substituted with one or two fatty ether substituents. Additional skin permeation enhancers will be known to those of ordinary skill in the art of topical drug delivery, and/or are described in the relevant literature. See, e.g., Percutaneous Penetration Enhancers, eds. Smith et al. (CRC Press, Boca Raton, Fla., 1995).

Various other additives may be included in the topical formulations according to certain embodiments of the present invention, in addition to those identified above. These include, but are not limited to, antioxidants, astringents, perfumes, preservatives, emollients, pigments, dyes, humectants, propellants, and sunscreen agents, as well as other classes of materials whose presence may be cosmetically, medicinally or otherwise desirable. Typical examples of optional additives for inclusion in the formulations of certain embodiments of the invention are as follows: preservatives such as sorbate; solvents such as isopropanol and propylene glycol; astringents such as menthol and ethanol; emollients such as polyalkylene methyl glucosides; humectants such as glycerine; emulsifiers such as glycerol stearate, PEG-100 stearate, polyglyceryl-3 hydroxylauryl ether, and polysorbate 60; sorbitol and other polyhydroxyalcohols such as polyethylene glycol; sunscreen agents such as octyl methoxyl cinnamate (available commercially as PARSOL® MCX) and butyl methoxy benzoylmethane (available under the tradename PARSOL® 1789); antioxidants such as ascorbic acid (vitamin C), α-tocopherol (Vitamin E), β-tocopherol, γ-tocopherol, δ-tocopherol, ε-tocopherol, $\zeta_1$-tocopherol, $\zeta_2$-tocopherol, η-tocopherol, and retinol (vitamin A); essential oils, ceramides, essential fatty acids, mineral oils, wetting agents and other surfactants such as the PLURONIC® series of hydrophilic polymers available from BASF (Mt. Olive, N.J.), vegetable oils (e.g., soy bean oil, palm oil, liquid fraction of shea butter, sunflower oil), animal oils (e.g., perhydrosqualene), mineral oils, synthetic oils, silicone oils or waxes (e.g., cyclomethicone and dimethicone), fluorinated oils (generally perfluoropolyethers), fatty alcohols (e.g., cetyl alcohol), and waxes (e.g., beeswax, carnauba wax, and paraffin wax); skin-feel modifiers; and thickeners and structurants such as swelling clays and cross-linked carboxypolyalkylenes that may be obtained commercially under the CARBOPOL® trademark.

Other additives include beneficial agents such as those materials that condition the skin (particularly, the upper layers of the skin in the stratum corneum) and keep it soft by retarding the decrease of its water content and/or protect the skin. Such conditioners and moisturizing agents include, by way of example, pyrrolidine carboxylic acid and amino acids; organic antimicrobial agents such as 2,4,4'-trichloro-2-hydroxy diphenyl ether (triclosan) and benzoic acid; anti-inflammatory agents such as acetylsalicylic acid and glycyrrhetinic acid; anti-seborrhoeic agents such as retinoic acid; vasodilators such as nicotinic acid; inhibitors of melanogenesis such as kojic acid; and mixtures thereof. Other advantageously included cosmeceutically active agents may be present, for example, α-hydroxyacids, α-ketoacids, polymeric hydroxyacids, moisturizers, collagen, marine extracts, and antioxidants such as ascorbic acid (vitamin C), α-tocopherol (Vitamin E) or other tocopherols such as those described above, and retinol (vitamin A), and/or cosmetically acceptable salts, esters, amides, or other derivatives thereof. Additional cosmetic agents include those that are capable of improving oxygen supply in skin tissue, as described, for example, in WO 94/00098 and WO 94/00109. Sunscreens may also be included.

Other embodiments may include a variety of non-carcinogenic, non-irritating healing materials that facilitate treatment with the formulations of certain embodiments of the invention. Such healing materials may include nutrients, minerals, vitamins, electrolytes, enzymes, herbs, plant extracts, honey, glandular or animal extracts, or safe therapeutic agents that may be added to the formulation to facilitate dermal healing. The amounts of these various additives are those conventionally used in the cosmetics field, and range, for example, from about 0.01% to about 20% of the total weight of the topical formulation.

The formulations of certain embodiments of the invention may also include conventional additives such as opacifiers, fragrance, colorant, gelling agents, thickening agents, stabilizers, surfactants, and the like. Other agents may also be added, such as antimicrobial agents, to prevent spoilage upon storage, i.e., to inhibit growth of microbes such as yeasts and molds. Suitable antimicrobial agents are typically selected from methyl and propyl esters of p-hydroxybenzoic acid (e.g., methyl and propyl paraben), sodium benzoate, sorbic acid, imidurea, and combinations thereof. The formulations may also contain irritation-mitigating additives to minimize or eliminate the possibility of skin irritation or skin damage resulting from the anti-infective acute or chronic wound healing and skin tissue repair-promoting compound to be administered, or from other components of the composition. Suitable irritation-mitigating additives include, for example: α-tocopherol; monoamine oxidase inhibitors, particularly phenyl alcohols such as 2-phenyl-1-ethanol; glycerin; salicylates; ascorbates; ionophores such as monensin; amphiphilic amines; ammonium chloride; N-acetylcysteine; capsaicin; and chloroquine. The irritation-mitigating additive, if present, may be incorporated into the topical formulation at a concentration effective to mitigate irritation or skin damage, typically representing not more than about 20 wt %, more typically not more than about 5 wt %, of the formulation.

The topical formulations may also contain, in addition to the antiseptic/wound healing/anti-biofilm/skin tissue repair-promoting compound (e.g., a BT compound, preferably as substantially homogeneous microparticles as provided herein, and optionally in combination with one or more synergizing antibiotics as described herein), a therapeutically effective amount of one or more additional pharmacologically active agents suitable for topical administration. Such agents may include an asymmetrical lamellar aggregate consisting of phospholipids and oxygen-loaded fluorocarbon or a fluorocarbon compound mixture, which are capable of improving oxygen supply in skin tissue, as described, for example, in International Patent Publication Nos. WO 94/00098 and WO 94/00109.

Suitable pharmacologically active agents that may be incorporated into the present topical formulations and thus topically applied, may include but are not limited to, the following: agents that improve or eradicate pigmented or non-pigmented age spots, keratoses, and wrinkles; antimicrobial agents; antibacterial agents; antipruritic and antixerotic agents; antiinflammatory agents; local anesthetics and analgesics; corticosteroids; retinoids (e.g., retinoic acid; vitamins; hormones; and antimetabolites. Some examples of topical pharmacologically active agents include acyclovir, amphotericins, chlorhexidine, clotrimazole, ketoconazole, econazole, miconazole, metronidazole, minocycline, nystatin, neomycin, kanamycin, phenyloin, para-amino benzoic acid esters, octyl methoxycinnamate, octyl salicylate, oxybenzone, dioxybenzone, tocopherol, tocopheryl acetate, selenium sulfide, zinc pyrithione, diphenhydramine, pramoxine, lidocaine, procaine, erythromycin, tetracycline, clindamycin, chromatin, hydroquinone and its monomethyl and benzyl ethers, naproxen, ibuprofen, cromolyn, retinoic acid, retinol, retinyl palmitate, retinyl acetate, coal tar, griseofulvin, estradiol, hydrocortisone, hydrocortisone 21-acetate, hydrocortisone 17-valerate, hydrocortisone 17-butyrate, progesterone, betamethasone valerate, betamethasone dipropionate, triamcinolone acetonide, fluocinonide, clobetasol propionate, minoxidil, dipyridamole, diphenylhydantoin, benzoyl peroxide, and 5-fluorouracil. As also noted above, certain embodiments contemplate inclusion in the formulation of an antibiotic such as a carbapenem antibiotic, a cephalosporin antibiotic, a fluoroquinolone antibiotic, a glycopeptide antibiotic, a lincosamide antibiotic, a penicillinase-resistant penicillin antibiotic, an aminopenicillin antibiotic, or an aminoglycoside antibiotic such as amikacin.

A pharmacologically acceptable carrier may also be incorporated in the topical formulation of certain present embodiments and may be any carrier conventionally used in the art. Examples include water, lower alcohols, higher alcohols, honey, polyhydric alcohols, monosaccharides, disaccharides, polysaccharides, sugar alcohols such as, for example, glycols (2-carbon), glycerols (3-carbon), erythritols and threitols (4-carbon), arabitols, xylitols and ribitols (5-carbon), mannitols, sorbitols, dulcitols and iditols (6-carbon), isomaltols, maltitols, lactitols and polyglycitols, hydrocarbon oils, fats and oils, waxes, fatty acids, silicone oils, nonionic surfactants, ionic surfactants, silicone surfactants, and water-based mixtures and emulsion-based mixtures of such carriers.

Topical formulation embodiments of the present invention may be applied regularly to whatever acute or chronic wound site (e.g., the wound itself and surrounding tissue, including surrounding tissue that appears unaffected by infection or otherwise normal or healthy) or skin area or other epithelial tissue surface (e.g., gastrointestinal tract, respiratory tract, glandular tissue) requires treatment with the frequency and in the amount necessary to achieve the desired results. The frequency of treatment depends on the nature of the skin (or other epithelial tissue) condition (e.g., an acute or chronic wound or other skin wound such as may be found in dehiscence that results from a surgical incision, or other types of skin wounds), the degree of damage or deterioration of the skin (or other tissue), the responsiveness of the user's skin (or other tissue), the strength of the active ingredients (e.g., the herein described wound-healing/antiseptic/anti-biofilm/skin tissue repair-promoting compounds such as a BT compound and optionally one or more additional pharmaceutically active ingredients, such as an antibiotic, e.g., amikacin or other antibiotic) in the particular embodiment, the effectiveness of the vehicle used to deliver the active ingredients into the appropriate layer of the skin (or other epithelial surface-containing tissue), the ease with which the formula is removed by physical contact with bandages or other dressings or clothing, or its removal by sweat or other intrinsic or extrinsic fluids, and the convenience to the subject's or patient's activity level or lifestyle.

Typical concentrations of active substances such as the BT compound antiseptic/anti-biofilm/wound-healing/skin tissue repair-promoting compositions described herein can range, for example, from about 0.001-30% by weight based on the total weight of the composition, to about 0.01-5.0%, and more preferably to about 0.1-2.0%. As one representative example, compositions of these embodiments of the present invention may be applied to an acute or chronic wound and/or to the skin at a rate equal to from about 1.0 mg/cm$^2$ of skin to about 20.0 mg/cm$^2$ of skin. Representative examples of topical formulations include, but are not limited to, aerosols, alcohols, anhydrous bases (such as lipsticks and powders), aqueous solutions, creams, emulsions (including either water-in-oil or oil-in-water emulsions), fats, foams, gels, hydro-alcoholic solutions, liposomes, lotions, microemulsions, ointments, oils, organic solvents, polyols, polymers, powders, salts, silicone derivatives, and waxes. Topical formulations may include, for example, chelating agents, conditioning agents, emollients, excipients, humectants, protective agents, thickening agents, or UV absorbing agents. One skilled in the art will appreciate that formulations other than those listed may be used in embodiments of the present invention.

Chelating agents may be optionally included in topical formulations, and may be selected from any agent that is suitable for use in a cosmetic composition, and may include any natural or synthetic chemical which has the ability to bind divalent cationic metals such as $Ca^{2+}$, $Mn^{2+}$, or $Mg^{2+}$. Examples of chelating agents include, but are not limited to EDTA, disodium EDTA, EGTA, citric acid, and dicarboxylic acids.

Conditioning agents may also be optionally included in topical formulations. Examples of skin conditioning agents include, but are not limited to, acetyl cysteine, N-acetyl dihydrosphingosine, acrylates/behenyl acrylate/dimethicone acrylate copolymer, adenosine, adenosine cyclic phosphate, adenosine phosphate, adenosine triphosphate, alanine, albumen, algae extract, allantoin and deriviatives, aloe barbadensis extracts, aluminum PCA, amyloglucosidase, arbutin, arginine, azulene, bromelain, buttermilk powder, butylene glycol, caffeine, calcium gluconate, capsaicin, carbocysteine, carnosine, beta-carotene, casein, catalase, cephalins, ceramides, *chamomilla recutita* (matricaria) flower extract, cholecalciferol, cholesteryl esters, coco-betaine, coenzyme A, corn starch modified, crystallins, cycloethoxymethicone, cysteine DNA, cytochrome C, darutoside, dextran sulfate, dimethicone copolyols, dimethylsilanol hyaluronate, DNA, elastin, elastin amino acids, epidermal growth factor, ergocalciferol, ergosterol, ethylhexyl PCA, fibronectin, folic acid, gelatin, gliadin, beta-glucan, glucose, glycine, glycogen, glycolipids, glycoproteins, glycosaminoglycans, glycosphingolipids, horseradish peroxidase, hydrogenated proteins, hydrolyzed proteins, jojoba oil, keratin, keratin amino acids, and kinetin, lactoferrin, lanosterol, lauryl PCA, lecithin, linoleic acid, linolenic acid, lipase, lysine, lysozyme, malt extract, maltodextrin, melanin, methionine, mineral salts, niacin, niacinamide, oat amino acids, oryzanol, palmitoyl hydrolyzed proteins, pancreatin, papain, PEG, pepsin, phospholipids, phytosterols, placental enzymes, placental lipids, pyridoxal 5-phosphate, quercetin, resorcinol acetate, riboflavin, RNA, *saccharomyces* lysate extract, silk amino acids, sphingolipids, stearamidopropyl betaine, stearyl palmitate, tocopherol, tocopheryl acetate, tocopheryl linoleate, ubiquinone, *vitis vinifera* (grape) seed oil, wheat amino acids, xanthan gum, and zinc gluconate. Skin conditioning agents other than those listed above may be combined with a disclosed composition or preparation provided thereby, as can be readily appreciated by one skilled in the art.

Topical formulations may also optionally include one or more emollients, examples of which include, but are not limited to, acetylated lanolin, acetylated lanolin alcohol, acrylates/$C_{10-30}$ alkyl acrylate crosspolymer, acrylates copolymer, alanine, algae extract, aloe barbadensis extract or gel, althea officinalis extract, aluminum starch octenylsuccinate, aluminum stearate, apricot (*prunus armeniaca*) kernel oil, arginine, arginine aspartate, *arnica montana* extract, ascorbic acid, ascorbyl palmitate, aspartic acid, avocado (*persea gratissima*) oil, barium sulfate, barrier sphingolipids, butyl alcohol, beeswax, behenyl alcohol, beta-sitosterol, BHT, birch (*betula alba*) bark extract, borage (*borago officinalis*) extract, 2-bromo-2-nitropropane-1,3-diol, butcherbroom (*ruscus aculeatus*) extract, butylene glycol, *calendula officinalis* extract, *calendula officinalis* oil, candelilla (*euphorbia cerifera*) wax, canola oil, caprylic/capric triglyceride, *cardamon* (*elettaria cardamomum*) oil, carnauba (*copernicia cerifera*) wax, carrageenan (*chondrus crispus*), carrot (*daucus carota sativa*) oil, castor (*ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*anthemis nobilis*) oil, cholesterol, cholesterol esters, cholesteryl hydroxystearate, citric acid, clary (*salvia sclarea*) oil, cocoa (*theobroma cacao*) butter, coco-caprylate/caprate, coconut (*cocos nucifera*) oil, collagen, collagen amino acids, corn (*zea mays*) oil, fatty acids, decyl oleate, dextrin, diazolidinyl urea, dimethicone copolyol, dimethiconol, dioctyl adipate, dioctyl succinate, dipentaerythrityl hexacaprylate/hexacaprate, DMDM hydantoin, DNA, erythritol, ethoxydiglycol, ethyl linoleate, eucalyptus globulus oil, evening primrose (*oenothera biennis*) oil, fatty acids, tructose, gelatin, geranium maculatum oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*vitis vinifera*) seed oil, hazel (*corylus americana*) nut oil, hazel (*corylus avellana*) nut oil, hexylene glycol, honey, hyaluronic acid, hybrid safflower (*carthamus tinctorius*) oil, hydrogenated castor oil, hydrogenated cocoglycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, imidazolidinyl urea, iodopropynyl butylcarbamate, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*jasminum officinale*) oil, jojoba (*buxus chinensis*) oil, kelp, kukui (*aleurites moluccana*) nut oil, lactamide MEA, laneth-16, laneth-10 acetate, lanolin, lanolin acid, lanolin alcohol, lanolin oil, lanolin wax, lavender (*lavandula angustifolia*) oil, lecithin, lemon (*citrus medica limonum*) oil, linoleic acid, linolenic acid, *macadamia ternifolia* nut oil, magnesium stearate, magnesium sulfate, maltitol, matricaria (*chamomilla recutita*) oil, methyl glucose sesquistearate, methylsilanol PCA, microcrystalline wax, mineral oil, mink oil, *mortierella* oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*olea europaea*) oil, orange (*citrus aurantium dulcis*) oil, palm (*elaeis guineensis*) oil, palmitic acid, pantethine, panthenol, panthenyl ethyl ether, paraffin, PCA, peach (*prunus persica*) kernel oil, peanut (*arachis hypogaea*) oil, PEG-8 C12 18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG-40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (*mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, potassium sorbate, potassium stearate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, quaternium-15, quaternium-18 hectorite, quaternium-22, retinol, retinyl palmitate, rice (*oryza sativa*)

bran oil, RNA, rosemary (*rosmarinus officinalis*) oil, rose oil, safflower (*carthamus tinctorius*) oil, sage (*salvia officinalis*) oil, salicylic acid, sandalwood (*santalum album*) oil, serine, serum protein, sesame (*sesamum indicum*) oil, shea butter (*butyrospermum parkii*), silk powder, sodium chondroitin sulfate, sodium DNA, sodium hyaluronate, sodium lactate, sodium palmitate, sodium PCA, sodium polyglutamate, sodium stearate, soluble collagen, sorbic acid, sorbitan laurate, sorbitan oleate, sorbitan palmitate, sorbitan sesquioleate, sorbitan stearate, sorbitol, soybean (glycine soja) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*helianthus annuus*) seed oil, sweet almond (*prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*triticum vulgare*) germ oil, and ylang ylang (*cananga odorata*) oil.

In some embodiments a topical formulation may contain a suitable excipient, which typically should have a high affinity for the skin, be well tolerated, stable, and yield a consistency that allows for easy utilization. Suitable topical excipients and vehicles can be routinely selected for a particular use by those skilled in the art, and especially with reference to one of many standard texts in the art, such as Remington's Pharmaceutical Sciences, Vol. 18, Mack Publishing Co., Easton, Pa. (1990), in particular Chapter 87. Optionally one or more humectants are also included in the topical formulation. Examples of humectants include, but are not limited to, amino acids, chondroitin sulfate, diglycerin, erythritol, fructose, glucose, glycerin, glycerol, glycol, 1,2,6-hexanetriol, honey, hyaluronic acid, hydrogenated honey, hydrogenated starch hydrolysate, inositol, lactitol, maltitol, maltose, mannitol, natural moisturization factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Certain embodiments contemplate topical formulations containing one or more additional skin protective agent. Examples of skin protective agents may include, but are not limited to, algae extract, allantoin, aluminum hydroxide, aluminum sulfate, betaine, *camellia sinensis* leaf extract, cerebrosides, dimethicone, glucuronolactone, glycerin, kaolin, lanolin, malt extract, mineral oil, petrolatum, potassium gluconate, and talc. One skilled in the art will readily appreciate that skin protectants other than those listed above may also be combined with a disclosed composition of the present invention or preparation provided thereby.

Surfactants may also desirably be included in certain topical formulations contemplated herein, and can be selected from any natural or synthetic surfactants suitable for use in cosmetic compositions, such as cationic, anionic, zwitterionic, or non-ionic surfactants, or mixtures thereof. (See Rosen, M., "Surfactants and Interfacial Phenomena," Second Edition, John Wiley & Sons, New York, 1988, Chapter 1, pages 4 31). Examples of cationic surfactants may include, but are not limited to, DMDAO or other amine oxides, long-chain primary amines, diamines and polyamines and their salts, quaternary ammonium salts, polyoxyethylenated long-chain amines, and quaternized polyoxyethylenated long-chain amines. Examples of anionic surfactants may include, but are not limited to, SDS; salts of carboxylic acids (e.g., soaps); salts of sulfonic acids, salts of sulfuric acid, phosphoric and polyphosphoric acid esters; alkylphosphates; monoalkyl phosphate (MAP); and salts of perfluorocarboxylic acids. Examples of zwitterionic surfactants may include, but are not limited to, cocoamidopropyl hydroxysultaine (CAPHS) and others which are pH-sensitive and require special care in designing the appropriate pH of the formula (I.e., alkylaminopropionic acids, imidazoline carboxylates, and betaines) or those which are not pH-sensitive (e.g., sulfobetaines, sultaines). Examples of non-ionic surfactants may include, but are not limited to, alkylphenol ethoxylates, alcohol ethoxylates, polyoxyethylenated polyoxypropylene glycols, polyoxyethylenated mercaptans, long-chain carboxylic acid esters, alkanolamides, tertiary acetylenic glycols, polyoxyethylenated silicones, N-alkypyrrolidones, and alkylpolyglycosidases. Wetting agents, mineral oil or other surfactants such as non-ionic detergents or agents such as one or more members of the PLURONICS® series (BASF, Mt. Olive, N.J.) may also be included, for example and according to non-limiting theory, to discourage aggregation of BT microparticles within the microparticulate suspension. Any combination of surfactants is acceptable. Certain embodiments may include at least one anionic and one cationic surfactant, or at least one cationic and one zwitterionic surfactant which are compatible, i.e., do not form complexes which precipitate appreciably when mixed.

Examples of thickening agents that may also be present in certain topical formulations include, but are not limited to, acrylamides copolymer, agarose, amylopectin, bentonite, calcium alginate, calcium carboxymethyl cellulose, carbomer, carboxymethyl chitin, cellulose gum, dextrin, gelatin, hydrogenated tallow, hydroxytheylcellulose, hydroxypropylcellulose, hydroxypropyl starch, magnesium alginate, methylcellulose, microcrystalline cellulose, pectin, various PEG's, polyacrylic acid, polymethacrylic acid, polyvinyl alcohol, various PPG's, sodium acrylates copolymer, sodium carrageenan, xanthan gum, and yeast beta-glucan. Thickening agents other than those listed above may also be used in embodiments of this invention.

According to certain embodiments contemplated herein, a topical formulation may comprise one or more sunscreening or UV absorbing agents. Where ultraviolet light- (UVA and UVB) absorbing properties are desired, such agents may include, for example, benzophenone, benzophenone-1, benzophenone-2, benzophenone-3, benzophenone-4, benzophenone-5, benzophenone-6, benzophenone-7, benzophenone-8, benzophenone-9, benzophenone-10, benzophenone-11, benzophenone-12, benzyl salicylate, butyl PABA, cinnamate esters, cinoxate, DEA-methoxycinnamate, diisopropyl methyl cinnamate, ethyl dihydroxypropyl PABA, ethyl diisopropylcinnamate, ethyl methoxycinnamate, ethyl PABA, ethyl urocanate, glyceryl octanoate dimethoxycinnamate, glyceryl PABA, glycol salicylate, homosalate, isoamyl p-methoxycinnamate, oxides of titanium, zinc, zirconium, silicon, manganese, and cerium, PABA, PABA esters, butyl methoxy benzoylmethane (available under the tradename PARSOL® 1789), and isopropylbenzyl salicylate, and mixtures thereof. One skilled in the art will appreciate that sunscreening and UV absorbing or protective agents other than those listed may be used in certain embodiments of the present invention.

Topical formulations disclosed herein are typically effective at pH values between about 2.5 and about 10.0. Preferably, the pH of the composition is at or about the following pH ranges: about pH 5.5 to about pH 8.5, about pH 5 to about pH 10, about pH 5 to about pH 9, about pH 5 to about pH 8, about pH 3 to about pH 10, about pH 3 to about pH 9, about pH 3 to about pH 8, and about pH 3 to about pH 8.5. Most preferably, the pH is about pH 7 to about pH 8. One of ordinary skill in the art may add appropriate pH adjusting ingredients to the compositions of the present invention to adjust the pH to an acceptable range. "About" a specified pH is understood by those familiar with the art to include formulations in which at any given time the actual measured pH may be less or more than the specified value by no more than 0.7, 0.6, 0.5, 0.4, 0.3, 0.2 or 0.1 pH units, where it is recognized that formulation composition and storage conditions may result in drifting of pH from an original value.

A cream, lotion, gel, ointment, paste or the like may be spread on the affected surface and gently rubbed in. A solution may be applied in the same way, but more typically will be applied with a dropper, swab, or the like, and carefully applied to the affected areas. The application regimen will depend on a number of factors that may readily be determined, such as the severity of the wound and its responsiveness to initial treatment, but will normally involve one or more applications per day on an ongoing basis. One of ordinary skill may readily determine the optimum amount of the formulation to be administered, administration methodologies and repetition rates. In general, it is contemplated that the formulations of these and related embodiments of the invention will be applied in the range of once or twice or more weekly up to once, twice, thrice, four times or more daily.

As also discussed above, the topical formulations useful herein thus also contain a pharmaceutically acceptable carrier, including any suitable diluent or excipient, which includes any pharmaceutical agent that does not itself harm the subject receiving the composition, and which may be administered without undue toxicity. Pharmaceutically acceptable carriers include, but are not limited to, liquids, such as water, saline, glycerol and ethanol, and the like, and may also include viscosity enhancers (e.g., balsam fir resin) or film-formers such as collodion or nitrocellulose solutions. A thorough discussion of pharmaceutically acceptable carriers, diluents, and other excipients is presented in REMINGTON'S PHARMACEUTICAL SCIENCES (Mack Pub. Co., N.J. current edition).

When the topical formulation is in the form of a gel- or liquid-filled capsule, for example, a gelatin capsule, it may contain, in addition to materials of the above type, a liquid carrier such as polyethylene glycol or oil. The liquid pharmaceutical compositions of certain embodiments of the invention, whether they be solutions, suspensions or other like form, may include one or more of the following: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; additional antioxidants such as ascorbic acid or sodium bisulfite; chelating agents such as ethylenediaminetetraacetic acid (EDTA); buffers such as acetates, citrates or phosphates and agents for the adjustment of tonicity such as sodium chloride or dextrose.

For topical administration the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical or cosmeceutical composition for topical administration. If intended for transdermal administration, the composition may include a transdermal patch or iontophoresis device. Topical formulations may contain a concentration of the compound of certain embodiments of the invention from about 0.1 to about 10% w/v (weight per unit volume). A topical formulation may be provided in the form of a cream, lotion, solution, spray, gel, ointment, paste or the like, and/or may contain liposomes, micelles, microspheres and/or other microparticle or nanoparticle delivery elements. A topical formulation may also be provided in the form of time-release or sustained release particles or pellets, for example, slow-release ethylene vinyl acetate polymer (e.g., ELVAX®40, Aldrich, Milwaukee, Wis.) pellets, that can be directly administered to a wound site.

The topical formulation may include an agent that binds to the skin tissue repair-promoting compound and thereby assists in its delivery to skin epithelial cells (e.g., keratinocytes) and/or fibroblasts. Suitable agents that may act in this capacity include clathrating agents such as cyclodextrins; other agents may include a protein or a liposome.

The topical formulation of certain embodiments of the invention may also be provided in the form of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of certain embodiments of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols for delivering topical formulations to the skin or to a wound site.

The topical formulations may be prepared by methodology well known in the pharmaceutical art. For example, a pharmaceutical composition intended to be administered to a wound site or to the skin as a spray, wash or rinse can be prepared by combining a BT antiseptic/wound-healing/anti-biofilm/skin tissue repair-promoting compound as described herein with sterile, distilled water so as to form a solution. A surfactant may be added to facilitate the formation of a homogeneous solution or suspension. Surfactants are compounds that non-covalently interact with the antioxidant active compound so as to facilitate dissolution or homogeneous suspension of the compound in the aqueous delivery system.

The BT antiseptic/wound-healing/anti-biofilm/skin tissue repair-promoting compounds for use in topical formulations, or their pharmaceutically acceptable salts, are administered in a therapeutically effective amount, which will vary depending upon a variety of factors including the nature of the wound site (where relevant), the activity of the specific BT compound employed (including the inclusion or absence from the formulation of an antibiotic, such as an aminoglycoside antibiotic, e.g., amikacin); the metabolic stability and length of action of the compound; the age, body weight, general health, sex, skin type, immune status and diet of the subject; the mode and time of administration; the rate of excretion; the drug combination; the severity of the particular skin wound for which skin tissue repair is desired; and the subject undergoing therapy. Generally, a therapeutically effective daily dose is (for a 70 kg mammal) from about 0.001 mg/kg (i.e., 0.07 mg) to about 100 mg/kg (i.e., 7.0 g); preferably a therapeutically effective dose is (for a 70 kg mammal) from about 0.01 mg/kg (i.e., 7 mg) to about 50 mg/kg (i.e., 3.5 g); more preferably a therapeutically effective dose is (for a 70 kg mammal) from about 1 mg/kg (i.e., 70 mg) to about 25 mg/kg (i.e., 1.75 g).

The ranges of effective doses provided herein are not intended to be limiting and represent preferred dose ranges. However, the most preferred dosage will be tailored to the individual subject, as is understood and determinable by one skilled in the relevant arts. (see, e.g., Berkow et al., eds., The Merck Manual, 16$^{th}$ edition, Merck and Co., Rahway, N.J., 1992; Goodman et al., eds., Goodman and Gilman's The Pharmacological Basis of Therapeutics, 10$^{th}$ edition, Pergamon Press, Inc., Elmsford, N.Y., (2001); Avery's Drug Treatment: Principles and Practice of Clinical Pharmacology and Therapeutics, 3rd edition, ADIS Press, Ltd., Williams and Wilkins, Baltimore, Md. (1987); Ebadi, Pharmacology, Little, Brown and Co., Boston, (1985); Osolci al., eds., Remington's Pharmaceutical Sciences, 18$^{th}$ edition, Mack Publishing Co., Easton, Pa. (1990); Katzung, Basic and Clinical Pharmacology, Appleton and Lange, Norwalk, Conn. (1992)).

The total dose required for each treatment can be administered by multiple doses or in a single dose over the course of the day, if desired. Certain preferred embodiments contemplate a single application of the topical formulation per day. Generally, and in distinct embodiments, treatment may be initiated with smaller dosages, which are less than the optimum dose of the compound. Thereafter, the dosage is increased by small increments until the optimum effect under the circumstances is reached.

The topical formulation can be administered alone or in conjunction with other treatments and/or pharmaceuticals directed to the skin wound, or directed to other associated symptoms or etiologic factors. For example, and as also noted above, the topical formulation may further comprise retinoic acid. As another example, the topical formulation may comprise one or more skin tissue repair-promoting compounds described herein, or may comprise two or more such compounds having different cellular wound repair activities.

The recipients of the topical formulations described herein can be any vertebrate animal, such as mammals. Among mammals, the preferred recipients are mammals of the Orders Primate (including humans, apes and monkeys), Arteriodactyla (including horses, goats, cows, sheep, pigs), Rodenta (including mice, rats, rabbits, and hamsters), and Carnivora (including cats, and dogs). Among birds, the preferred recipients are turkeys, chickens and other members of the same order. The most preferred recipients are humans, and particularly preferred are humans having one or more acute or chronic wounds or wounds that contain biofilms.

For topical applications, it is preferred to administer an effective amount of a pharmaceutical composition comprising a BT compound antiseptic/wound-healing/anti-biofilm/skin tissue repair-promoting compound according to the herein described embodiments, to a target area, e.g., a skin wound such as an acute or chronic wound, and/or an at-risk area (e.g., for wound dehiscence) of the skin, and the like. This amount will generally range from about 0.0001 mg to about 1 g of a compound of certain embodiments of the invention per application, depending upon the area to be treated, the severity of the wound (or of a past or contemplated surgical incision), and the nature of the topical vehicle employed. A preferred topical preparation is an ointment or slow-release pellets, wherein about 0.001 to about 50 mg of active ingredient is used per cc of ointment base or pellet suspension. The pharmaceutical composition can be formulated as transdermal compositions or transdermal delivery devices ("patches"). Such compositions include, for example, a backing, active compound reservoir, a control membrane, liner and contact adhesive. Such transdermal patches may be used to provide continuous pulsatile, or on demand delivery of the compounds of the present invention as desired.

The compositions of certain embodiments can be formulated so as to provide quick, sustained or delayed release of the active ingredient after administration to the patient by employing procedures known in the art. Controlled release drug delivery systems include osmotic pump systems and dissolutional systems containing polymer-coated reservoirs or drug-polymer matrix formulations. Examples of controlled release systems are given in U.S. Pat. Nos. 3,845,770 and 4,326,525 and in P. J. Kuzma et al, Regional Anesthesia 22 (6): 543-551 (1997), all of which are incorporated herein by reference.

The most suitable route will depend on the nature and severity of the condition being treated. Those skilled in the art are also familiar with determining topical administration methods (sprays, creams, open application, occlusive dressing, soaks, washes, etc.), dosage forms, suitable pharmaceutical excipients and other matters relevant to the delivery of the compounds to a subject in need thereof.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are required and may or may not be present depending upon whether or not they affect the activity or action of the listed elements.

In this specification and the appended claims, the singular forms "a," "an" and "the" include plural references unless the content clearly dictates otherwise. As used herein, in particular embodiments, the terms "about" or "approximately" when preceding a numerical value indicates the value plus or minus a range of 5%, 6%, 7%, 8% or 9%. In other embodiments, the terms "about" or "approximately" when preceding a numerical value indicates the value plus or minus a range of 10%, 11%, 12%, 13% or 14%. In yet other embodiments, the terms "about" or "approximately" when preceding a numerical value indicates the value plus or minus a range of 15%, 16%, 17%, 18%, 19% or 20%.

The following Examples are presented by way of illustration and not limitation.

EXAMPLES

Example 1

Preparation of BT Compounds

The following BT compounds were prepared either according to the methods of Domenico et al. (U.S. RE37,793, U.S. Pat. No. 6,248,371, U.S. Pat. No. 6,086,921, U.S. Pat. No. 6,380,248) or as microparticles according to the synthetic protocol described below for BisEDT. Shown are atomic ratios relative to a single bismuth atom, for comparison, based on the stoichiometric ratios of the reactants used and the known propensity of bismuth to form trivalent complexes with sulfur containing compounds. The numbers in parenthesis are the ratios of bismuth to one (or more) thiol agents (e.g. Bi:thiol1/thiol2; see also Table 1).

1) CPD 1B-1 Bis-EDT (1:1) BiC2H4S2
2) CPD 1B-2 Bis-EDT (1:1.5) $BiC_3H_6S_3$
3) CPD 1B-3 Bis-EDT (1:1.5) $BiC_3H_6S_3$
4) CPD 1C Bis-EDT (soluble Bi prep.) (1:1.5) $BiC_3H_6S_3$
5) CPD 2A Bis-Bal (1:1) $BiC_3H_6S_2O$
6) CPD 2B Bis-Bal (1:1.5) $BiC_{4.5}H_9O_{1.5}S_3$
7) CPD 3A Bis-Pyr (1:1.5) $BiC_{7.5}H_6N_{1.5}O_{1.5}S_{1.5}$
8) CPD 3B Bis-Pyr (1:3) $BiC_{15}H_{12}N_3O_3S_3$
9) CPD 4 Bis-Ery (1:1.5) $BiC_6H_{12}O_3S_3$
10) CPD 5 Bis-Tol (1:1.5) $BiC_{10.5}H_9S_3$
11) CPD 6 Bis-BDT (1:1.5) $BiC_6H_{12}S_3$
12) CPD 7 Bis-PDT (1:1.5) $BiC_{4.5}H_9S_3$
13) CPD 8-1 Bis-Pyr/BDT (1:1/1)
14) CPD 8-2 Bis-Pyr/BDT (1:1/0.5)
15) CPD 9 Bis-2hydroxy, propane thiol (1:3)
16) CPD 10 Bis-Pyr/Bal (1:1/0.5)
17) CPD 11 Bis-Pyr/EDT (1:1/0.5)
18) CPD 12 Bis-Pyr/Tol (1:1/0.5)
19) CPD 13 Bis-Pyr/PDT (1:1/0.5)
20) CPD 14 Bis-Pyr/Ery (1:1/0.5)
21) CPD 15 Bis-EDT/2hydroxy, propane thiol (1:1/1)

Microparticulate bismuth-1,2-ethanedithiol (Bis-EDT, soluble bismuth preparation) was prepared as follows:

To an excess (11.4 L) of 5% aqueous $HNO_3$ at room temperature in a 15 L polypropylene carboy was slowly added by dropwise addition 0.331 L (~0.575 moles) of an aqueous $Bi(NO_3)_3$ solution (43% $Bi(NO_3)_3$ (w/w), 5% nitric acid (w/w), 52% water (w/w), Shepherd Chemical Co., Cincinnati, Ohio, product no. 2362; δ~1.6 g/mL) with stirring, followed by slow addition of absolute ethanol (4 L). Some white precipitate formed but was dissolved by continued stirring. An ethanolic solution (~1.56 L, ~0.55 M) of 1,2-ethanedithiol (CAS 540-63-6) was separately prepared by adding, to 1.5 L of absolute ethanol, 72.19 mL (0.863 moles) of 1,2-ethanedithiol using a 60 mL syringe, and then stirring for five minutes. The 1,2-ethanedithiol/EtOH reagent was then slowly added by dropwise addition over the course of five hours to the aqueous $Bi(NO_3)_3/HNO_3$ solution, with continued stirring overnight. The formed product was allowed to settle as a precipitate for approximately 15 minutes, after which the filtrate was removed at 300 mL/min using a peristaltic pump. The product was then collected by filtration on fine filter paper in a 15-cm diameter Buchner funnel, and washed sequentially with three, 500-mL volumes each of ethanol, USP water, and acetone to obtain BisEDT (694.51 gm/mole) as a yellow amorphous powdered solid. The product was placed in a 500 mL amber glass bottle and dried over $CaCl_2$ under high vacuum for 48 hours. Recovered material (yield ~200 g) gave off a thiol-characteristic odor. The crude product was redissolved in 750 mL of absolute ethanol, stirred for 30 min, then filtered and washed sequentially with 3×50 mL ethanol, 2×50 mL acetone, and washed again with 500 mL of acetone. The rewashed powder was triturated in 1M NaOH (500 mL), filtered and washed with 3×220 mL water, 2×50 mL ethanol, and 1×400 mL acetone to afford 156.74 gm of purified BisEDT. Subsequent batches prepared in essentially the same manner resulted in yields of about 78-91%.

The product was characterized as having the structure shown above in formula I by analysis of data from $^1H$ and $^{13}C$ nuclear magnetic resonance (NMR), infrared spectroscopy (IR), ultraviolet spectroscopy (UV), mass spectrometry (MS) and elemental analysis. An HPLC method was developed to determine chemical purity of BisEDT whereby the sample was prepared in DMSO (0.5 mg/mL). The $\lambda_{max}$ was determined by scanning a solution of BisEDT in DMSO between 190 and 600 nm. Isocratic HPLC elution at 1 mL/min was performed at ambient temperature in a mobile phase of 0.1% formic acid in acetonitrile:water (9:1) on a WATERS® (Millipore Corp., Milford, Mass.) model 2695 chromatograph with UV detector monitoring at 265 nm ($\lambda_{max}$), 2 μL injection volume, equipped with a YMC-PACK® PVC Sil NP, 5 μm, 250×4.6 mm inner diameter analytical column (WATERS®) and a single peak was detected, reflecting chemical purity of 100±0.1%. Elemental analysis was consistent with the structure of formula (I).

The dried particulate matter was characterized to assess the particle size properties. Briefly, microparticles were resuspended in 2% polyoxypropylene/polyoxyethylene copolymers sold under the trademark PLURONIC® F-68 (BASF, Mt. Olive, N.J.) and the suspension was sonicated for 10 minutes in a water bath sonicator at standard setting prior to analysis using a NANOSIZER™/ZETASIZER® Nano-S particle analyzer (model ZEN1600 (without zeta-potential measuring capacity), MALVERN INSTRUMENTS™, Worcestershire, UK) according to the manufacturer's recommendations. From compiled data of two measurements, microparticles exhibited a unimodal distribution with all detectable events between about 0.6 microns and 4 microns in volumetric mean diameter (VMD) and having a peak VMD at about 1.3 microns. By contrast, when BisEDT was prepared by prior methods (Domenico et al., 1997 *Antimicrob. Agents Chemother.* 41(8):1697-1703) the majority of particles were heterodisperse and of significantly larger size, precluding their characterization on the basis of VMD.

Example 2

Colony Biofilm Model of Chronic Wound Infection: Inhibition by BT Compounds

Because bacteria that exist in chronic wounds adopt a biofilm lifestyle, BTs were tested against biofilms for effects on bacterial cell survival using biofilms prepared essentially according to described methods (Anderl et al., 2003 *Antimicrob Agents Chemother* 47:1251-56; Walters et al., 2003 *Antimicrob Agents Chemother* 47:317; Wentland et al., 1996 *Biotchnol. Prog.* 12:316; Zheng et al., 2002 *Antimicrob Agents Chemother* 46:900).

Briefly, colony biofilms were grown on 10% tryptic soy agar for 24 hours, and transferred to Mueller Hinton plates containing treatments. After treatment the biofilms were dispersed into peptone water containing 2% w/v glutathione (neutralizes the BT), and serially diluted into peptone water before being spotted onto plates for counting. Two bacteria isolated from chronic wounds were used separately in the production of colony biofilms for testing. These were *Pseudomonas aeruginosa*, a gram negative bacterial strain, and Methicillin Resistant *Staphylococcus aureus* (MRSA), which is gram positive.

Bacterial biofilm colonies were grown on top of micro porous membranes resting on an agar plate essentially as described (Anderl et al., 2003 *Antimicrob Agents Chemother* 47:1251-56; Walters et al., 2003 *Antimicrob Agents Chemother* 47:317; Wentland et al., 1996 *Biotchnol. Prog.* 12:316; Zheng et al., 2002 *Antimicrob Agents Chemother* 46:900) The colony biofilms exhibited many of the familiar features of other biofilm models, e.g., they consisted of cells densely aggregated in a highly hydrated matrix. As also reported by others (Brown et al., *J Surg Res* 56:562; Millward et al, 1989 *Microbios* 58:155; Sutch et al., 1995 *J Pharm Pharmacol* 47:1094; Thrower et al., 1997 *J Med Microbiol* 46:425) it was observed that bacteria in colony biofilms exhibited the same profoundly reduced anti-microbial susceptibility that has been quantified in more sophisticated in vitro biofilm reactors. Colony biofilms were readily and reproducibly generated in large numbers. According to non-limiting theory, this colony biofilm model shared some of the features of an infected wound: bacteria grew at an air interface with nutrients supplied from beneath the biofilm and minimal fluid flow. A variety of nutrients sources was used to cultivate colony biofilms, including blood agar, which is believed to mimic in vivo nutrient conditions.

Colony biofilms were prepared by inoculating 5 µl spots of planktonic bacterial liquid cultures onto a 25 mm diameter polycarbonate filter membrane. The membranes were sterilized prior to inoculation, by exposure to ultraviolet light for 10 min per side. The inocula were grown overnight in bacterial medium at 37° C. and diluted in fresh medium to an optical density of 0.1 at 600 nm prior to deposition on the membrane. The membranes were then placed on the agar plate containing growth medium. The plates were then covered and placed, inverted, in an incubator at 37° C. Every 24 h, the membrane and colony biofilm were transferred, using sterile forceps, to a fresh plate. Colony biofilms were typically used for experimentation after 48 hours of growth, at which time there were approximately $10^9$ bacteria per membrane. The colony biofilm method was successfully employed to culture a wide variety of single species and mixed species biofilms.

To measure susceptibility to antimicrobial agents (e.g., BT compounds including combinations of BT compounds; antibiotics; and BT compound-antibiotic combinations), colony biofilms were transferred to agar plates supplemented with the candidate antimicrobial treatment agent(s). Where the duration of exposure to antimicrobial treatment exceeded 24 hours, the colony biofilms were moved to fresh treatment plates daily. At the end of the treatment period, the colony biofilms were placed in tubes containing 10 ml of buffer and vortexed for 1-2 min to disperse the biofilm. In some cases, it was necessary to briefly process the sample with a tissue homogenizer to break up cell aggregates. The resulting cell suspensions were then serially diluted and plated to enumerate surviving bacteria, which were reported as colony forming units (CFU) per unit area. Survival data were analyzed using $\log_{10}$ transformation.

For each type of bacterial biofilm colony cultures (*Pseudomonas aeruginosa*, PA; methicilin resistant *Staphylococcus aureus*, MRSA or SA) five antibiotics and thirteen BT compounds were tested. Antimicrobial agents tested against PA included the BTs referred to herein as BisEDT and Compounds 2B, 4, 5, 6, 8-2, 9, 10, 11 and 15 (see Table 1), and the antibiotics tobramycin, amikacin, imipenim, cefazolin, and ciprofloxacin. Antimicrobial agents tested against SA included the BTs referred to herein as BisEDT and Compounds 2B, 4, 5, 6, 8-2, 9, 10 and 11 (see Table 1), and the antibiotics rifampicin, daptomycin, minocycline, ampicillin, and vancomycin. As described above under "brief descriptions of the drawings", antibiotics were tested at concentrations of approximately 10-400 times the minimum inhibitory concentrations (MIC) according to established microbiological methodologies.

Figure 2:
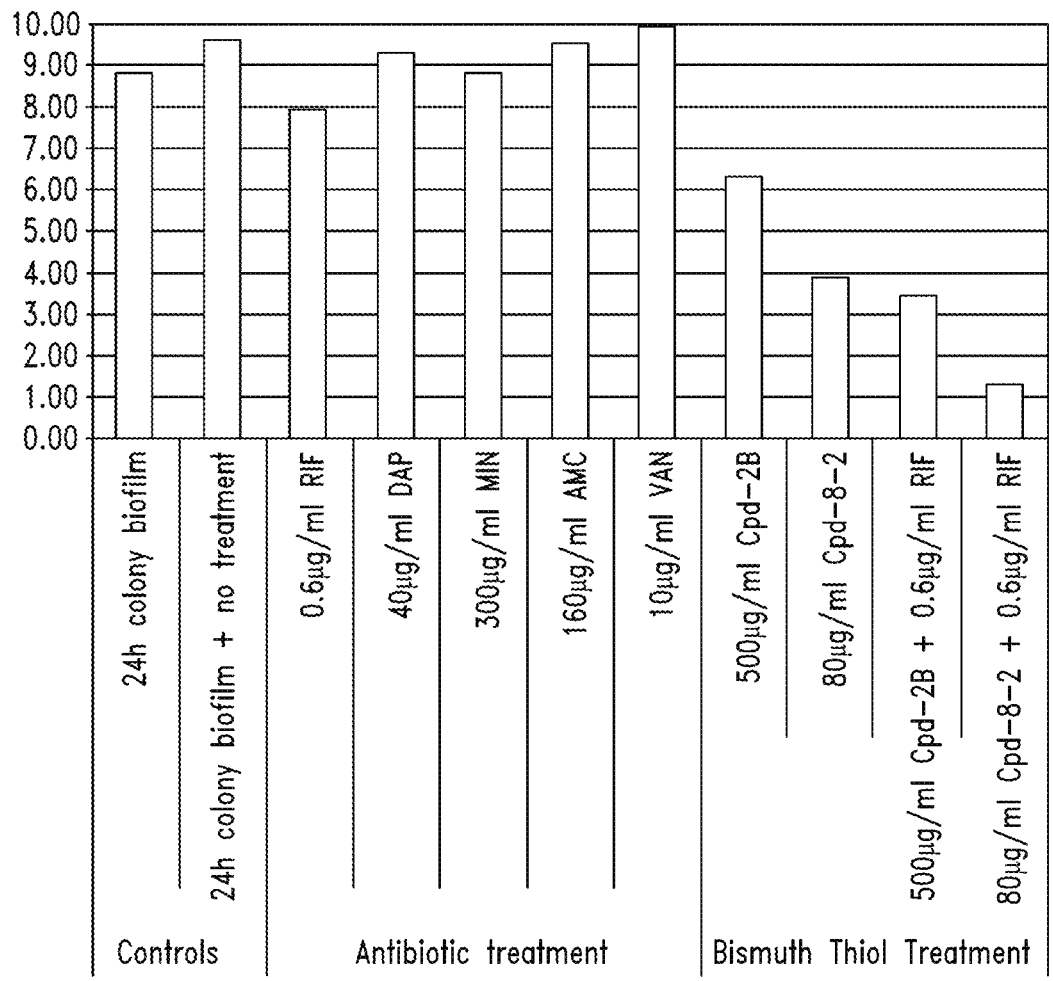
FIG. 2 shows surviving numbers (log CFU) from *Staphylococcus aureus* colony biofilms grown for 24 hours on 10% tryptic soy agar, followed by the indicated treatment. Indicated antibiotic treatments are Rifampicin, RIF 100×MIC; daptomycin, DAP 320×MIC; minocycline, MIN 100×MIC; ampicillin, AMC 10×MIC; vancomycin, VAN 10×MIC; Cpd 2B, compound 2B (Bis-BAL, 1:1.5), Cpd 8-2, compound 8-2 (Bis-Pyr/BDT (1:1/0.5).

Seven BT compounds exhibited pronounced effects on PA bacterial survival at the concentrations tested, and two BT compounds demonstrated pronounced effects on MRSA survival at the concentrations tested; representative results showing BT effects on bacterial survival are presented in FIG. 1 for BisEDT and BT compound 2B (tested against PA) and in FIG. 2 for BT compounds 2B and 8-2 (tested against SA), in both cases, relative to the effects of the indicated antibiotics. As also shown in FIGS. 1 and 2, inclusion of the indicated BT compounds in combination with the indicated antibiotics resulted in a synergistic effect whereby the potency of reducing bacterial survival was enhanced relative to the anti-bacterial effects of either the antibiotic alone or the BT compound alone. In the PA survival assay, compound 15 (Bis-EDT/2hydroxy, propane thiol (1:1/1)) at a concentration of 80 µg/mL exhibited an effect (not shown) that was comparable to the effect obtained using the combination of 1600 µg/mL AMK plus 80 µg/mL BisEDT (FIG. 1).

Example 3

Drip Flow Biofilm Model of Chronic Wound Infection: Inhibition by BT Compounds

Drip flow biofilms represent an art accepted authentic model for forming, and testing the effect of candidate antibacterial compounds against, bacterial biofilms. Drip flow biofilms are produced on coupons (substrates) placed in the channels of a drip flow reactor. Many different types of materials can be used as the substrate for bacterial biofilm formation, including frosted glass microscope slides. Nutritive liquid media enters the drip flow bioreactor cell chamber by dripping into the chamber near the top, and then flows the length of a coupon down a 10 degree slope.

Biofilms are grown in drip flow bioreactors and exposed to BT compounds individually or in combinations and/or to antibiotic compounds individually or in combinations with other antibacterial agents, including BT compounds, or to other conventional or candidate treatments for chronic wounds. BT compounds are thus characterized for their effects on bacterial biofilms in the drip-flow reactor. Biofilms in the drip-flow reactor are prepared according to established methodologies (e.g., Stewart et al., 2001 *J Appl Microbiol.* 91:525; Xu et al., 1998 *Appl. Environ. Microbiol.* 64:4035). This design involves cultivating biofilms on inclined polystyrene coupons in a covered chamber. An exemplary culture medium contains 1 g/l glucose, 0.5 g/l $NH_4NO_3$, 0.25 g/l KCl, 0.25 g/l $KH_2PO_4$, 0.25 g/l $MgSO_4.7H_2O$, supplemented with 5% v/v adult donor bovine serum (ph 6.8) that mimics serum protein-rich, iron limited conditions that are similar to biofilm growth conditions in vivo, such as in chronic wounds. This medium flows drop-wise (50 ml/h) over four coupons contained in four separate parallel chambers, each of which measures 10 cm×1.9 cm by 1.9 cm deep. The chambered reactor is fabricated from polysulfone plastic. Each of the chambers is fitted with an individual removable plastic lid that can be tightly sealed. The biofilm reactor is contained in an incubator at 37° C., and bacterial cell culture medium is warmed by passing it through an aluminum heat sink kept in the incubator. This method reproduces the antibiotic tolerant phenotype observed in certain biofilms, mimics the low fluid shear environment and proximity to an air interface characteristic of a chronic wound while providing continual replenishment of nutrients, and is compatible with a number of analytical methods for characterizing and monitoring the effects of introduced candidate antibacterial regimens. The drip-flow reactor has been successfully employed to culture a wide variety of pure and mixed-species biofilms. Biofilms are typically grown for two to five days prior to application of antimicrobial agents.

To measure the effects of anti-biofilm agents on biofilms grown in drip-flow reactors, the fluid stream passing over the biofilm is amended or supplemented with the desired treatment formulation (e.g., one or more BT compounds and/or one or more antibiotics, or controls, and/or other candidate agents). Flow is continued for the specified treatment period.

The treated biofilm coupon is then briefly removed from the reactor and the biofilm is scraped into a beaker containing 10 ml of buffer. This sample is briefly processed (typically 30 s to 1 min) with a tissue homogenizer to disperse bacterial aggregates. The suspension is serially diluted and plated to enumerate surviving microorganisms according to standard microbiological methodologies.

Example 4

Wound Biofilm Inhibition of Keratinocyte Scratch Repair: Biofilm Suppression by BT Compounds This Example describes a modification of established in vitro keratinocyte scratch models of wound healing, to arrive at a model having relevance to biofilm-associated wound pathology and wound healing, and in particular to acute or chronic wounds or wounds containing biofilms as described herein. According to the keratinocyte scratch model of the effects of chronic wound biofilms, cultivation of mammalian (e.g., human) keratinocytes and bacterial biofilm populations proceeds in separate chambers that are in fluid contact with one another, to permit assessment of the effects of conditions that influence the effects, of soluble components elaborated by biofilms, on keratinocyte wound healing events.

Newborn human foreskin cells are cultured as monolayers in treated plastic dishes, in which monolayers a controlled "wound" or scratch is formed by mechanical means (e.g., through physical disruption of the monolayer such as by scraping an essentially linear cell-free zone between regions of the monolayer with a suitable implement such as a sterile scalpel, razor, cell scraper, forceps or other tool). In vitro keratinocyte monolayer model systems are known to undergo cellular structural and functional process in response to the wounding event, in a manner that simulates wound healing in vivo. According to the herein disclosed embodiments, the influence of the presence of bacterial biofilms on such processes, for instance, on the healing time of the scratch, is observed, and in these and related embodiments the effects are also assessed of the presence of selected candidate antimicrobial (e.g., antibacterial and antibiofilm) treatments.

Wounded keratinocyte monolayers cultured in the presence of biofilms are examined according to morphological, biochemical, molecular genetic, cell physiologic and other parameters to determine whether introduction of BT compounds alters (e.g., increases or decreases in a statistically significant manner relative to appropriate controls) the damaging effects of the biofilms. Wounds are first exposed to each BT compound alone, and to contemplated combinations of BT compounds, in order to test the toxicity of each BT compound treatment prior to assessing the effects of such treatments on biofilm influences toward the model wound healing process.

In a representative embodiment, a three-day biofilm is cultured on a membrane (e.g., a membrane insert sold by Costar Corp. under the trademark TRANSWELL®, or the like) that is maintained in a tissue culture well above, and in fluid communication with, a keratinocyte monolayer that is scratched to initiate the wound healing process. Biofilms cultured out of authentic acute or chronic wounds are contemplated for use in these and related embodiments.

Thus, an in vitro system has been developed for evaluating soluble biofilm component effects on migration and proliferation of human keratinocytes. The system separates the biofilm and keratinocytes using a dialysis membrane. Keratinocytes are cultured from newborn foreskin as previously described (Fleckman et al., 1997 *J. Invest. Dermatol.* 109:36; Piepkorn et al., 1987 *J. Invest. Dermatol.* 88:215-219) and grown as confluent monolayers on glass cover slips. The keratinocyte monolayers can then be scratched to yield "wounds" with a uniform width, followed by monitoring cellular repair processes (e.g., Tao et al., 2007 *PLoS ONE* 2:e697; Buth et al. 2007 *Eur. J. Cell Biol.* 86:747; Phan et al. 2000 *Ann. Acad. Med. Singapore* 29:27). The artificial wounds are then placed in the bottom of a sterile double-sided chamber and the chamber is assembled using aseptic technique. Both sides of the chamber are filled with keratinocyte growth medium (EpiLife) with or without antibiotics and/or bismuth-thiols. Uninoculated systems are used as controls.

The system is inoculated with wound-isolated bacteria and incubated in static conditions for two hours to enable bacterial attachment to surfaces in the upper chambers. Following the attachment period, liquid medium flow is initiated in the upper chamber to remove unattached cells. Flow of medium is then continued at a rate that minimizes the growth of planktonic cells within the upper chamber, by washout of unattached cells. After incubation periods ranging from 6 to 48 hours, the systems (keratinocyte monolayers on coverslips and bacterial biofilm on membrane substrate) are disassembled and the cover slips removed and analyzed. In related embodiments, mature biofilms are grown in the upper chamber prior to assembling the chamber. In other related embodiments, the separate co-culturing of biofilms and scratch-wounded keratinocyte monolayers is conducted in the absence and presence of one or more BT compounds, optionally with the inclusion or exclusion of one or more antibiotics, in order to determine effects of candidate agents such as BT compounds, or of potentially synergizing BT compound-plus-antibiotic combinations (e.g., a BT compound as provided herein such as a BT that is provided in microparticulate form, and one or more of amikacin, ampicillin, cefazolin, cefepime, chloramphenicol, ciprofloxacin, clindamycin (or another lincoasamide antibiotic), daptomycin (sold under the trademark CUBICIN®), doxycycline, gatifloxacin, gentamicin, imipenim, levofloxacin, linezolid (sold under the trademark ZYVOX®), minocycline, nafcilin, paromomycin, rifampin, sulphamethoxazole, tobramycin and vancomycin), on keratinocyte repair of the scratch wound, e.g., to identify an agent or combination of agents that alters (e.g., increases or decreases in a statistically significant manner relative to appropriate controls) at least one indicator of scratch wound healing, such as the time elapsing for wound repair to take place or other wound-repair indicia (e.g., Tao et al., 2007 *PLoS ONE* 2:e697; Buth et al. 2007 *Eur. J Cell Biol.* 86:747; Phan et al. 2000 *Ann. Acad. Med. Singapore* 29:27).

Example 5

Wound Biofilm Inhibition of Keratinocyte Scratch Repair

Figure 3:
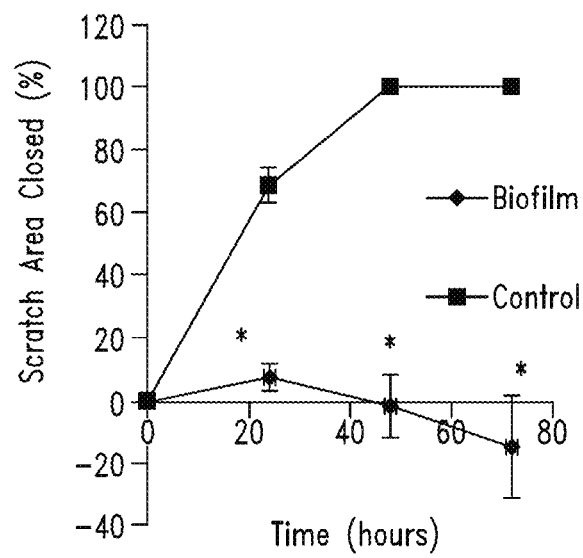
FIG. 3 shows scratch closure over time of keratinocytes exposed to biofilms. (*) Significantly different from control (P<0.001).

Isolated human keratinocytes were cultured on glass coverslips and scratch-wounded according to methodologies described above in Example 4. Wounded cultures were maintained under culture conditions alone or in the presence of a co-cultured biofilm on a membrane support in fluid communication with the keratinocyte culture. The scratch closure time interval during which keratinocyte cell growth and/or migration reestablishes the keratinocyte monolayer over the scratch zone was then determined. FIG. 3 illustrates the effect that the presence in fluid communication (but without direct contact) of biofilms had on the healing time of scratched keratinocyte monolayers.

Accordingly there are contemplated in certain embodiments a method of identifying an agent for treating a chronic wound, comprising culturing a scratch-wounded cell (e.g., keratinocyte or fibroblast) monolayer in the presence of a bacterial biofilm with and without a candidate anti-biofilm agent being present; and assessing an indicator of healing of the scratch-wounded cell monolayer in the absence and presence of the candidate anti-biofilm agent, wherein an agent (e.g., a BT compound such as a substantially monodisperse BT microparticle suspension as described herein, alone or in synergizing combination with an antibiotic, such as one or more of amikacin, ampicillin, cefazolin, cefepime, chloramphenicol, ciprofloxacin, clindamycin, daptomycin (CUBICIN®), doxycycline, gatifloxacin, gentamicin, imipenem, levofloxacin, linezolid (ZYVOX®), minocycline, nafcilin, paromomycin, rifampin, sulphamethoxazole, tobramycin and vancomycin) that promotes at least one indicator of healing is identified as a suitable agent for treating an acute or chronic wound or a wound that contains a biofilm.

Example 6

Synergizing Bismuth-Thiol (BT)-Antibiotic Combinations

This example shows instances of demonstrated synergizing effects by combinations of one or more bismuth-thiol compounds and one or more antibiotics against a variety of bacterial species and bacterial strains, including several antibiotic-resistant bacteria.

Materials & Methods. Susceptibility studies were performed by broth dilution in 96-well tissue culture plates (Nalge Nunc International, Denmark) in accordance with NCCLS protocols (National Committee for Clinical Laboratory Standards. (1997). Methods for Dilution Antimicrobial Susceptibility Tests for Bacteria that Grow Aerobically: Approved Standard M7-A2 and Informational Supplement M100-S10. NCCLS, Wayne, Pa., USA).

Briefly, overnight bacterial cultures were used to prepare 0.5 McFarland standard suspensions, which were further diluted 1:50 (~2×10$^6$ cfu/mL) in cation-adjusted Mueller-Hinton broth medium (BBL, Cockeysville, Md., USA). BTs (prepared as described above) and antibiotics were added at incremental concentrations, keeping the final volume constant at 0.2 mL. Cultures were incubated for 24 h at 37° C. and turbidity was assessed by absorption at 630 nm using an ELISA plate reader (Biotek Instruments, Winooski, Vt., USA) according to the manufacturer's recommendations. The Minimum Inhibitory Concentration (MIC) was expressed as the lowest drug concentration inhibiting growth for 24 h. Viable bacterial counts (cfu/mL) were determined by standard plating on nutrient agar. The Minimal Bactericidal Concentrations (MBC) was expressed as the concentration of drug that reduced initial viability by 99.9% at 24 h of incubation.

The checkerboard method was used to assess the activity of antimicrobial combinations. The fractional inhibitory concentration index (FICI) and the fractional bactericidal concentration index (FBCI) were calculated, according to Eliopoulos et al. (Eliopoulos and Moellering, (1996) Antimicrobial combinations. In Antibiotics in Laboratory Medicine (Lorian, V., Ed.), pp. 330-96, Williams and Wilkins, Baltimore, Md., USA). Synergy was defined as an FICI or FBCI index of ≤0.5, no interaction at >0.5-4 and antagonism at >4 (Odds, F C (2003) Synergy, antagonism, and what the chequerboard puts between them. *Journal of Antimicrobial Chemotherapy* 52:1). Synergy was also defined conventionally as ≥4-fold decrease in antibiotic concentration.

Results are presented in Tables 2-17.

TABLE 2

S. aureus Nafcilin resistant

| Strain | NAF MIC (µg/ml) | NAF/BE MIC (µg/ml) | Δ | Synergy |
|---|---|---|---|---|
| 60187-2 | 10.00 | 0.6 | 16.7 | + |
| 52446-3 | 175.00 | 40.0 | 4.4 | + |
| M1978 | 140.00 | 50.0 | 2.8 | − |
| W54793 | 130.00 | 33.3 | 3.9 | − |
| S24341 | 210.00 | 65.0 | 3.2 | − |
| H7544 | 28.33 | 15.0 | 1.9 | − |
| H72751 | 145.00 | 43.3 | 3.3 | − |
| W71630 | 131.67 | 46.7 | 2.8 | − |
| X22831 | 178.33 | 75.0 | 2.4 | − |
| X23660 | 123.33 | 43.3 | 2.8 | − |
| O36466 | 191.67 | 93.3 | 2.1 | − |

BE = 0.2 µg/ml BisEDT;
Bacterial strains were obtained from the Clinical Microbiology Laboratory at Winthrop-University Hospital, Mineola, NY. Nafcillin was obtained from Sigma (St. Louis, MO).

TABLE 3

S. aureus Nafcilin resistant

| Strain | GM MIC (µg/ml) | GM/BE MIC (µg/ml) | Δ | Synergy |
|---|---|---|---|---|
| 60187-2 | 0.233 | 0.004 | 58.3 | + |
| 52446-3 | 10.667 | 1.500 | 7.1 | + |
| M1978 | 32.500 | 4.000 | 8.1 | + |
| W54793 | 0.250 | 0.080 | 3.1 | − |
| S24341 | 0.250 | 0.058 | 4.3 | + |
| H7544 | 0.383 | 0.093 | 4.1 | + |
| H72751 | 0.200 | 0.072 | 2.8 | − |
| W71630 | 17.667 | 3.800 | 4.6 | + |
| X22831 | — | 0.085 | | |
| X23660 | 22.500 | 4.000 | 5.6 | + |
| O36466 | 0.267 | 0.043 | 6.2 | + |

BE = 0.2 µg/ml BisEDT;
Bacterial strains were obtained from the Clinical Microbiology Laboratory at Winthrop-University Hospital, Mineola, NY. Nafcillin was obtained from Sigma.

TABLE 4

S. aureus
Rifampin/Neomycin/Paromomycin

| | MIC (µg/ml) | MIC + BE (µg/ml) | Δ | Synergy |
|---|---|---|---|---|
| ATCC 25923 | | | | |
| RIF | 0.033 | 0.003 | 13.0 | + |
| NEO | 0.500 | 0.200 | 2.5 | − |
| PARO | 1.080 | 0.188 | 5.7 | + |
| MRSA S2446-3 | | | | |
| RIF | 2.500 | 2.500 | 1.0 | − |
| NEO | 13.400 | 8.500 | 1.6 | − |
| PARO | 335.000 | 183.300 | 1.8 | − |

BE = 0.2 µg/ml BisEDT;
Strain S2446-3 was obtained from the Clinical Microbiology Laboratory at Winthrop-University Hospital, Mineola, NY. Antibiotics were obtained from Sigma.

TABLE 5

*S. epidermidis* - GM resistant

| BisEDT (μg/ml) | strain ATCC 35984 | | strain S2400-1 | |
|---|---|---|---|---|
| | MIC (μg/ml GM) | MBC (μg/ml GM) | MIC (μg/ml GM) | MBC (μg/ml GM) |
| 0 | 53.3 | 384.0 | 85.3 | 426.7 |
| 0.005 | 20.0 | 96.0 | 96.0 | 512.0 |
| 0.01 | 37.3 | 117.3 | 64.0 | 256.0 |
| 0.02 | 21.3 | 26.7 | 28.0 | 128.0 |
| 0.04 | 2.0 | 16.0 | 2.0 | 128.0 |
| 0.08 | 2.0 | 10.7 | 2.0 | 53.3 |
| 0.16 (MIC) | | 3.0 | | 10.0 |
| 0.32 | | 2.0 | | 4.0 |

GM = gentamicin;
Strain S2400-1 was obtained from the Clinical Microbiology Laboratory at Winthrop-University Hospital, Mineola, NY. Gentamicin was obtained from the Pharmacy Department at Winthrop; synergy in bold

TABLE 6

*S. epidermidis* - S2400-1
Biofilm Prevention

| Antibiotic | BisEDT (μg/ml) | | | Δ (0.05 BE) | Synergy |
|---|---|---|---|---|---|
| | 0 | 0.05 | 0.1 | | |
| cefazolin | 28 | 10 | 1 | 2.8 | – |
| vancomycin | 3.2 | 0.9 | 0.1 | 3.6 | – |
| gatifloxacin | 1.6 | 0.1 | 0.1 | 16.0 | ++ |
| rifampicin | 0.03 | 0.04 | 0.04 | 0.7 | – |
| nafcillin | 48 | 64 | 8 | 0.8 | – |
| clindamycin | 1195 | 48 | 12 | 24.9 | ++++ |
| gentamicin | 555 | 144 | 12 | 3.9 | borderline |
| minocycline | 0.85 | 0.73 | 0.08 | 1.2 | – |

Data in μg/ml;
Strain S2400-1 was obtained from the Clinical Microbiology Laboratory at Winthrop-University Hospital, Mineola, NY. Antibiotics were obtained from the Pharmacy Department at Winthrop.

TABLE 7

*S. epidermidis* - S2400-1
MIC

| Antibiotic | BisEDT (μg/ml) | | | Δ (0.05 BE) | Synergy |
|---|---|---|---|---|---|
| | 0 | 0.05 | 0.1 | | |
| cefazolin | 32 | 8 | 1 | 4.00 | + |
| vancomycin | 3.2 | 2.3 | 0.3 | 1.40 | – |
| gatifloxacin | 1.7 | 0.8 | 0.3 | 2.13 | – |
| rifampicin | 0.03 | 0.04 | 0.04 | 0.75 | – |
| nafcillin | 171 | 192 | 68 | 0.89 | – |
| clindamycin | 2048 | 768 | 24 | 2.67 | – |
| gentamicin | 2048 | 320 | 80 | 6.40 | + |
| minocycline | 1.13 | 0.43 | 0.10 | 2.63 | – |

Data in μg/ml;
Strain S2400-1 was obtained from the Clinical Microbiology Laboratory at Winthrop-University Hospital, Mineola, NY. Antibiotics were obtained from the Pharmacy Department at Winthrop.

TABLE 8

*S. epidermidis* - S2400-1
MBC

| Antibiotic | BisEDT (μg/ml) | | Δ (0.1 BE) | Synergy |
|---|---|---|---|---|
| | 0.0 | 0.1 | | |
| cefazolin | 48 | 10 | 4.80 | + |
| vancomycin | 5.4 | 1.4 | 3.86 | borderline |
| gatifloxacin | 2.8 | 1.4 | 2.00 | – |
| rifampicin | 0.03 | 0.07 | 0.43 | – |
| nafcillin | 256 | 128 | 2.00 | – |
| clindamycin | 2048 | 768 | 2.67 | – |
| gentamicin | 1536 | 256 | 6.00 | + |
| minocycline | 1.20 | 1.20 | 1.00 | – |

Data in μg/ml;
Strain S2400-1 was obtained from the Clinical Microbiology Laboratory at Winthrop-University Hospital, Mineola, NY. Antibiotics were obtained from the Pharmacy Department at Winthrop.

TABLE 9

*S. epidermidis*
ATCC 35984
MIC

| Antibiotic | BisEDT (μg/ml) | | Δ | Synergy |
|---|---|---|---|---|
| | 0.0 | 0.05 | | |
| Nafcillin | 16.00 | 5.00 | 3.2 | – |
| Clindamycin | 2048.00 | 1024.00 | 2 | – |
| Gentamicin | 213.33 | 16.00 | 13.3 | ++ |
| Minocycline | 0.13 | 0.04 | 3.3 | – |
| Rifampicin | 0.021 | 0.014 | 1.5 | – |

Data in μg/ml;
Antibiotics were obtained from the Pharmacy Department at Winthrop-University Hospital, Mineola, NY.

TABLE 10

*E. coli* - Ampicillin/Chloramphenicol resistant

| Strain | MIC AB (μg/ml) | MIC AB/BE (μg/ml AB) | Δ | Synergy | MIC BE (μg/ml) |
|---|---|---|---|---|---|
| MC4100/TN9 (CM) | 220 | 12.7 | 17.4 | + | 0.6 |
| MC4100/P9 (AM) | 285 | 49 | 5.8 | + | 0.5 |
| MC4100 (AM) | 141.7 | 35 | 4.0 | + | 0.6 |

AB = antibiotic;
CM = chloramphenicol;
AM = ampicillin;
BE = BisEDT at 0.3 μg/ml;
Strains were obtained from the laboratory of Dr. MJ Casadaban, Department of Molecular Genetics and Cell Biology, The University of Chicago, Chicago, IL. Antibiotics were obtained from the Pharmacy Department at Winthrop-University Hospital, Mineola, NY.

TABLE 11

*E. coli* - Tetracycline-resistant:
Doxycycline + BisEDT

| Strain | DOX MIC (μg/ml) | DOX/BE MIC (μg/ml DOX) | Δ | Synergy | BE MIC (μg/ml) |
|---|---|---|---|---|---|
| TET M | 16.50 | 4.50 | 4.0 | + | 0.85 |
| TET D | 20.50 | 0.03 | 820.0 | ++++ | 0.85 |
| TET A | 15.00 | 10.00 | 1.5 | – | 0.40 |
| TET B | 20.13 | 10.33 | 2.0 | – | 0.60 |

DOX = doxycycline;
BE = BisEDT at 0.3 μg/ml;
Strains were obtained from the laboratory of Dr. I Chopra, Department of Bacteriology, The University of Bristol, Bristol, UK. Antibiotics were obtained from the Pharmacy Department at Winthrop-University Hospital, Mineola, NY.

TABLE 12

*P. aeruginosa* - Tobramycin-resistant:
BisEDT Synergy

| Strain | NN (μg/ml) | NN + BE (μg/ml NN) | Δ | Synergy | BE MIC (μg/ml) |
|---|---|---|---|---|---|
| Xen5 | 0.32 | 0.19 | 1.68 | − | 0.9 |
| Agr PA E | 115 | 70 | 1.64 | − | 0.9 |
| Agr PA I | 200 | 73 | 2.74 | − | 1 |
| Agr PA K | 4.8 | 3 | 1.60 | − | 0.82 |
| Agr PA O | 130 | 20.5 | 6.34 | + | 0.98 |

Agr = aminoglycoside resistant;

NN = tobramycin;

PA = *Pseudomonas aeruginosa*;

BE = BisEDT, 0.3 μg/ml;

Strains were obtained from the laboratory of Dr. K. Poole, Department of Microbiology and Immunology, Queens University, Ontario, CN. Tobramycin was obtained from the Pharmacy Department at Winthrop-University Hospital, Mineola, NY.

TABLE 13

*B. cepacia*
Tobramycin + BE Synergy
MIC

| Strain | NN (μg/ml) | NN + BE (μg/ml NN) | Δ | Synergy | BE MIC (μg/ml) |
|---|---|---|---|---|---|
| 13945 | 200 | 50 | 4 | + | 2.4 |
| 25416 | 125 | 10 | 12.5 | ++ | 1.2 |
| HI 2229 | 64 | 8 | 8 | + | 0.8 |
| AU 0267 | 128 | 2 | 64 | ++++ | 0.8 |
| AU 0259 | 1024 | 256 | 4 | + | 1.6 |
| HI 2255 | 64 | 8 | 8 | + | 1.6 |
| AU 0273 | 512 | 32 | 16 | ++ | 1.6 |
| HI 2253 | 64 | 16 | 4 | + | 1.6 |
| HI 2147 | 512 | 8 | 64 | ++++ | 1.6 |

NN = Tobramycin;

BE = BisEDT, 0.4 μg/ml;

Strains were obtained from the laboratory of Dr. J. J. LiPuma, Department of Pediatrics and Communicable Diseases, University of Michigan, Ann Arbor, MI; also Veloira et al. 2003. Tobramycin was obtained from the Pharmacy Department at Winthrop-University Hospital, Mineola, NY.

TABLE 14

*B. cepacia*
Tobramycin + BE Synergy
MBC

| Strain | NN (μg/ml) | NN + BE (μg/ml NN) | Δ | Synergy | BE MIC (μg/ml) |
|---|---|---|---|---|---|
| HI 2249 | 256 | 8 | 32 | ++ | 3.2 |
| HI 2229 | 128 | 32 | 4 | + | 6.4 |
| AU 0267 | 256 | 32 | 8 | + | 6.4 |
| AU 0259 | 1024 | 1024 | 1 | − | 12.8 |
| HI 2255 | 128 | 32 | 4 | + | 12.8 |
| HI 2711 | 512 | 8 | 64 | ++++ | 6.4 |
| AU 0284 | 1024 | 64 | 16 | ++ | 0.8 |
| AU 0273 | 512 | 32 | 16 | ++ | 1.6 |
| HI 2253 | 128 | 64 | 2 | − | 3.2 |
| HI 2147 | 512 | 128 | 4 | + | 6.4 |

NN = Tobramycin;

BE = BisEDT, 0.4 μg/ml;

Strains were obtained from the laboratory of Dr. J. J. LiPuma, Department of Pediatrics and Communicable Diseases, University of Michigan, Ann Arbor, MI; also Veloira et al. 2003. Tobramycin was obtained from the Pharmacy Department at Winthrop-University Hospital, Mineola, NY.

TABLE 15

Tobramycin Resistant Strains
MIC

| Strain | NN (μg/ml) | NN + BE (μg/ml NN) | Δ | Synergy | Lipo-BE-NN (μg/ml NN) |
|---|---|---|---|---|---|
| M13637 | 512 | 32 | 16 | ++ | 0.25 |
| M13642R | 128 | 64 | 2 | − | 0.25 |
| PA-48913 | 1024 | 256 | 4 | + | 0.25 |
| PA-48912-2 | 64 | 8 | 8 | + | 0.25 |
| PA-10145 | 1 | 4 | 0.25 | − | 0.25 |
| SA-29213 | 2 | 1 | 2 | − | 0.25 |

NN = Tobramycin;

BE = BisEDT, 0.8 μg/ml;

Lipo-BE-NN = liposomal BE-NN;

Strains were obtained from the laboratory of Dr. A. Omri, Department of Chemistry and Biochemistry, Laurentian University, Ontario, CN; (M strains are mucoid *B. cepacia*;

PA = *P. aeruginosa*;

SA = *S. aureus*). Tobramycin was obtained from the Pharmacy Department at Winthrop-University Hospital, Mineola, NY.

TABLE 16

Tobramycin Resistant Strains
MBC

| Strain | NN (μg/ml) | NN + BE (μg/ml NN) | Δ | Synergy | Lipo-BE-NN (μg/ml NN) |
|---|---|---|---|---|---|
| M13637 | 1024 | 64 | 16 | ++ | 8 |
| M13642R | 256 | 128 | 2 | − | 16 |
| PA-48913 | 4096 | 512 | 8 | + | 4 |
| PA-48912-2 | 128 | 32 | 4 | + | 0.5 |
| PA-10145 | 1 | 8 | 0.125 | − | 4 |
| SA-29213 | 2 | 1 | 2 | − | 0.25 |

NN = Tobramycin;

BE = BisEDT, 0.8 μg/ml;

Lipo-BE-NN = liposomal BE-NN;

Strains were obtained from the laboratory of Dr. A. Omri, Department of Chemistry and Biochemistry, Laurentian University, Ontario, CN; (M strains are mucoid *B. cepacia*; PA = *P. aeruginosa*; SA = *S. aureus*). Tobramycin was obtained from the Pharmacy Department at Winthrop-University Hospital, Mineola, NY.

TABLE 17

BisEDT-Pyrithione Synergy

| NaPYR (ug/ml) | *P. aeruginosa* ATCC 27853 (μg/ml BE) | *E. coli* ATCC 25922 (μg/ml BE) | *S. aureus* ATCC 25923 (μg/ml BE) |
|---|---|---|---|
| 0 | 0.25 | 0.1 | 0.25 |
| 0.025 |  | 0.1 | 0.125 |
| 0.05 |  | 0.025 | 0.063 |
| 0.1 | 0.125 | 0.0125 | 0.063 |
| 0.2 | 0.125 | 0.0125 | 0.031 |
| 0.4 |  | 0.00625 | 0 |
| 0.8 | 0.125 | 0.00625 |  |
| 1.6 (MIC) | 0.063 | 0.00625 |  |
| 3.2 | 0.063 | 0 |  |
| 6.4 | 0.063 |  |  |
| 12.8 | 0 |  |  |

BE = BisEDT;

NaPYR = sodium pyrithione;

Chemicals were obtained from Sigma-Aldrich;

synergy in bold.

Indicated bacterial strains were from American Type Culture Collection (ATCC, Manassas, VA).

Example 7

Comparative Bismuth-Thiol (BT) and Antibiotic Effects Against Gram-Positive and Gram-Negative Bacteria Including Antibiotic-Resistant Bacterial Strains In this example the in vitro activities of BisEDT and comparator agents were assessed against multiple clinical isolates of Gram-positive and—negative bacteria that are responsible for skin and soft tissue infections.

Materials and Methods. Test compounds and test concentration ranges were as follows: BisEDT (Domenico et al., 1997; Domenico et al., *Antimicrob. Agents Chemother.* 45(5): 1417-1421. and Example 1), 16-0.015 µg/mL; linezolid (ChemPacifica Inc., #35710), 64-0.06 µg/mL; Daptomycin (Cubist Pharmaceuticals # MCB2007), 32-0.03 µg/mL and 16-0.015 µg/mL; vancomycin (Sigma-Aldrich, St. Louis, Mo., # V2002), 64-0.06 µg/mL; ceftazidime, (Sigma # C3809), 64-0.06 µg/mL and 32-0.03 µg/mL; imipenem (United States Pharmacopeia, NJ, #1337809) 16-0.015 µg/mL and 8-0.008 µg/mL; ciprofloxacin (United States Pharmacopeia, # IOC265), 32-0.03 µg/mL and 4-0.004 µg/mL; gentamicin (Sigma #G3632) 32-0.03 µg/mL and 16-0.015 µg/mL. All test articles, except gentamicin, were dissolved in DMSO; gentamicin was dissolved in water. Stock solutions were prepared at 40-fold the highest concentration in the test plate. The final concentration of DMSO in the test system was 2.5%.

Organisms. The test organisms were obtained from clinical laboratories as follows: CHP, Clarian Health Partners, Indianapolis, Ind.; UCLA, University of California Los Angeles Medical Center, Los Angeles, Calif.; GR Micro, London, UK; PHRI TB Center, Public Health Research Institute Tuberculosis Center, New York, N.Y.; ATCC, American Type Culture Collection, Manassas, Va.; Mt Sinai Hosp., Mount Sinai Hospital, New York, N.Y.; UCSF, University of California San Francisco General Hospital, San Francisco, Calif.; Bronson Hospital, Bronson Methodist Hospital, Kalamazoo, Mich.; quality control isolates were from the American Type Culture Collection (ATCC, Manassas, Va.). Organisms were streaked for isolation on agar medium appropriate to each organism. Colonies were picked by swab from the isolation plates and put into suspension in appropriate broth containing a cryoprotectant. The suspensions were aliquoted into cryogenic vials and maintained at −80° C. Abbreviations are: BisEDT, bismuth-1,2-ethanedithiol; LZD, linezolid; DAP, daptomycin; VA, vancomycin; CAZ, ceftazidime; IPM, imipenem; CIP, ciprofloxacin; GM, gentamicin; MSSA, methicillin-susceptible *Staphylococcus aureus*; CLSI QC, Clinical and Laboratory Standards Institute quality control strain; MRSA, methicillin-resistant *Staphylococcus aureus*; CA-MRSA, community-acquired methicillin-resistant *Staphylococcus aureus*; MSSE, methicillin-susceptible *Staphylococcus epidermidis*; MRSE, methicillin-resistant *Staphylococcus epidermidis*; VSE, vancomycin-susceptible *Enterococcus*.

The isolates were streaked from the frozen vials onto appropriate medium: Trypticase Soy Agar (Becton-Dickinson, Sparks, Md.) for most organisms or Trypticase Soy Agar plus 5% sheep blood (Cleveland Scientific, Bath, Ohio) for streptococci. The plates were incubated overnight at 35° C. Quality control organisms were included. The medium employed for the MIC assay was Mueller Hinton II Broth (MHB II-Becton Dickinson, #212322) for most of the organisms. MHB II was supplemented with 2% lysed horse blood (Cleveland Scientific Lot # H13913) to accommodate the growth of *Streptococcus pyogenes* and *Streptococcus agalactiae*. The media were prepared at 102.5% normal weight to offset the dilution created by the addition of 5 µL drug solution to each well of the microdilution panels. In addition, for tests with daptomycin, the medium was supplemented with an additional 25 mg/L $Ca^{2+}$.

The MIC assay method followed the procedure described by the Clinical and Laboratory Standards Institute (Clinical and Laboratory Standards Institute. *Methods for Dilution Antimicrobial Susceptibility Tests for Bacteria That Grow Aerobically; Approved Standard—Seventh Edition*. Clinical and Laboratory Standards Institute document M7-A7 [ISBN 1-56238-587-9]. Clinical and Laboratory Standards Institute, 940 West Valley Road, Suite 1400, Wayne, Pa. 19087-1898 USA, 2006) and employed automated liquid handlers to conduct serial dilutions and liquid transfers. Automated liquid handlers included the MULTIDROP® 384 (Labsystems, Helsinki, Finland), BIOMEK® 2000 and MULTIMEK™ 96 (Beckman Coulter, Fullerton Calif.). The wells of Columns 2-12 of standard 96-well microdilution plates (Falcon 3918) were filled with 150 µL of DMSO or water for gentamicin on the MULTIDROP® 384. The drugs (300 µL) were dispensed into Column 1 of the appropriate row in these plates. These would become the mother plates from which the test plates (daughter plates) were prepared. The BIOMEK® 2000 completed serial transfers through Column 11 in the mother plates. The wells of Column 12 contained no drug and were the organism growth control wells in the daughter plates. The daughter plates were loaded with 185 µL of the appropriate test media (described above) using the MULTIDROP® 384. The daughter plates were prepared on the MULTIMEK™ 96 instrument which transferred 5 µL of drug solution from each well of a mother plate to each corresponding well of each daughter plate in a single step.

Standardized inoculum of each organism was prepared per CLSI methods (ISBN 1-56238-587-9, cited supra). Suspensions were prepared in MHB to equal the turbidity of a 0.5 McFarland standard. The suspensions were diluted 1:9 in broth appropriate to the organism. The inoculum for each organism was dispensed into sterile reservoirs divided by length (Beckman Coulter), and the BIOMEK® 2000 was used to inoculate the plates. Daughter plates were placed on the BIOMEK® 2000 work surface reversed so that inoculation took place from low to high drug concentration. The BIOMEK® 2000 delivered 10 µL of standardized inoculum into each well. This yielded a final cell concentration in the daughter plates of approximately $5 \times 10^5$ colony-forming-units/mL. Thus, the wells of the daughter plates ultimately contained 185 µL of broth, 5 µL of drug solution, and 10 µL of bacterial inoculum. Plates were stacked 3 high, covered with a lid on the top plate, placed in plastic bags, and incubated at 35° C. for approximately 18 hours for most of the isolates. The *Streptococcus* plates were read after 20 hours incubation. The microplates were viewed from the bottom using a plate viewer. For each of the test media, an uninoculated solubility control plate was observed for evidence of drug precipitation. The MIC was read and recorded as the lowest concentration of drug that inhibited visible growth of the organism.

Results. All marketed drugs were soluble at all of the test concentrations in both media. BisEDT exhibited a trace precipitate at 32 µg/mL, but MIC readings were not affected as the inhibitory concentrations for all organisms tested were well below that concentration. On each assay day, an appropriate quality control strain(s) was included in the MIC assays. The MIC values derived for these strains were compared to the published quality control ranges (Clinical and Laboratory Standards Institute. *Performance Standards for*

Antimicrobial Susceptibility Testing; Eighteenth Informational Supplement. CLSI document M100-S18 [ISBN 1-56238-653-0]. Clinical and Laboratory Standards Institute, 940 West Valley Road, Suite 1400, Wayne, Pa. 19087-1898 USA, 2008) for each agent, as appropriate.

On each assay day, an appropriate quality control strain(s) was included in the MIC assays. The MIC values derived for these strains were compared to the published quality control ranges (Clinical and Laboratory Standards Institute. *Performance Standards for Antimicrobial Susceptibility Testing; Eighteenth Informational Supplement.* CLSI document M100-S18 [ISBN 1-56238-653-0]) for each agent, as appropriate. Of 141 values for quality control strains where quality control ranges are published, 140(99.3%) were within the specified ranges. The one exception was imipenem versus *S. aureus* 29213 which yielded one value on a single run (≤0.008 µg/mL) that was one dilution below the published QC range. All other quality control results on that run were within the specified quality control ranges.

BisEDT demonstrated potent activity against both methicillin-susceptible *Staphylococcus aureus* (MSSA), methicillin-resistant *S. aureus* (MRSA), and community-acquired MRSA (CA-MRSA), inhibiting all strains tested at 1 µg/mL or less with an MIC90 values of 0.5 µg/mL for all three organism groups. BisEDT exhibited activity greater than that of linezolid and vancomycin and equivalent to that of daptomycin. Imipenem was more potent than BisEDT against MSSA (MIC90=0.03 µg/mL). However, MRSA and CAMRSA were resistant to imipenem while BisEDT demonstrated activity equivalent to that shown for MSSA. BisEDT was highly-active against methicillin-susceptible and methicillin—resistant *Staphylococcus epidermidis* (MSSE and MRSE), with MIC90 values of 0.12 and 0.25 µg/mL, respectively. BisEDT was more active against MSSE than any of the other agents tested except imipenem. BisEDT was the most active agent tested against MRSE.

BisEDT demonstrated activity equivalent to that of daptomycin, vancomycin, and imipenem against vancomycin-susceptible *Enterococcus faecalis* (VSEfc) with an MIC90 value of 2 µg/mL. Significantly, BisEDT was the most active agent tested against vancomycin-resistant *Enterococcus faecalis* (VREfc) with an MIC90 value of 1 µg/mL.

BisEDT was very active against vancomycin-susceptible *Enterococcus faecium* (VSEfm) with an MIC90 value of 2 µg/mL; its activity was equivalent to that or similar to that of daptomycin and one-dilution higher than that of vancomycin. BisEDT and linezolid were the most active agents tested against vancomycin-resistant *Enterococcus faecium* (VREfm), each demonstrating an MIC90 value of 2 µg/mL. The activity of BisEDT against *Streptococcus pyogenes* (MIC90 value of 0.5 µg/mL) was equivalent to that of vancomycin, greater than that of linezolid, and slightly less than that of daptomycin and ceftazidime. The compound inhibited all strains tested at 0.5 µg/mL or less. In these studies, the species that was least sensitive to BisEDT was *Streptococcus agalactiae* where the observed MIC90 value was 16 µg/mL. BisEDT was less active than all of the agents tested except gentamicin.

The activity of BisEDT and comparators against Gram-negative bacteria included demonstrated BisEDT potency against *Acinetobacter baumanii* (MIC90 value of 2 µg/mL) making BisEDT the most active compound tested. Elevated MICs for a significant number of test isolates for the comparator agents resulted in off-scale MIC90 values for these agents. BisEDT was a potent inhibitor of *Escherichia coli*, inhibiting all strains at 2 µg/mL or less (MIC90=2 µg/mL). The compound was less active than imipenem, but more active than ceftazidime, ciprofloxacin, and gentamicin.

BisEDT also demonstrated activity against *Klebsiella pneumoniae* with an MIC90 value of 8 µg/mL which was equivalent to that of imipenem. The relatively high MIC90 values exhibited by imipenem, ceftazidime, ciprofloxacin, and gentamicin indicated that this was a highly antibiotic-resistant group of organisms. BisEDT was the most active compound tested against *Pseudomonas aeruginosa* with an MIC90 value of 4 µg/mL. There was a high level of resistance to the comparator agents for this group of test isolates.

In summary, BisEDT demonstrated broad-spectrum potency against multiple clinical isolates representing multiple species, including species commonly involved in acute and chronic skin and skin structure infections in humans. The activity of BisEDT and key comparator agents was evaluated against 723 clinical isolates of Gram-positive and Gram-negative bacteria. The BT compound demonstrated broad spectrum activity, and for a number of the test organisms in this study, BisEDT was the most active compound tested in terms of anti-bacterial activity. BisEDT was most active against MSSA, MRSA, CA-MRSA, MSSE, MRSE, and *S. pyogenes*, where the MIC90 value was 0.5 µg/mL or less. Potent activity was also demonstrated for VSEfc, VREfc, VSEfm, VREfm, *A. baumanii, E. coli*, and *P. aeruginosa* where the MIC90 value was in the range of 1-4 µg/mL. MIC90 values observed were, for *K. pneumoniae* (MIC90=8 µg/mL), and for *S. agalactiae* (MIC90=16 µg/mL).

Example 8

Microparticulate BT-Antibiotic Enhancing and Synergizing Activities

This example shows that microparticulate bismuth thiols (BTs) promote antibiotic activity through enhancing and/or synergizing interactions.

A major complicating factor in treating infections is the emerging resistance of bacteria to antibiotics. Methicillin resistance in *S. epidermidis* (MRSE) and *S. aureus* (MRSA) actually reflects multiple drug resistance, making these pathogens very difficult to eradicate. However, no staphylococci from hundreds of strains tested showed resistance to BTs. Furthermore, BTs at subinhibitory (subMIC) concentrations reduced resistance to several important antibiotics.

*Staphylococcus aureus*

Figures 4A, 4B:
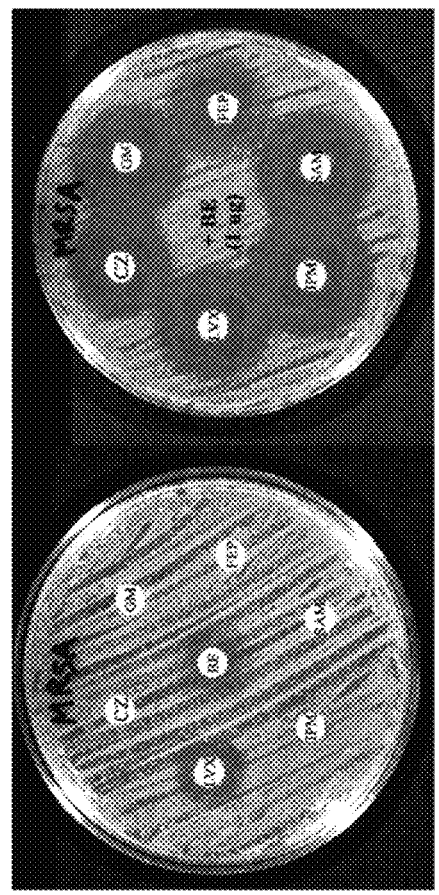
FIGS. 4A and 4B show the subinhibitory BisEDT reversing antibiotic-resistance to several antibiotics. Effects of antibiotics with and without BisEDT (0.05 µg/ml) on a lawn of MRSA (Methicillin-resistant *S. aureus*) is shown. Panel A shows standard antibiotic-soaked discs alone, and Panel B shows discs combined with a BisEDT (BE). [GM=gentamicin, CZ=cefazolin, FEP=cefepime, IPM=imipenem, SAM=ampicillin/sulbactam, LVX=levofloxacin.

A graphic demonstration of the antibiotic-resensitizing effects of subMIC bismuth ethanedithiol (BisEDT) against MRSA is provided (FIG. 4) showing enhanced antibiotic action of several classes of antibiotics, including gentamicin, cefazolin, cefepime, imipenim, sulphamethoxazole, and levofloxacin. Thus, BisEDT nonspecifically enhanced the activity of most antibiotics.

Broth dilution antimicrobial susceptibility studies were performed against 12 MRSA strains using several antibiotics combined with subMIC levels of BisEDT (Table 18). Both the biofilm-prevention concentration (BPC) and the minimum inhibitory concentration (MIC) were determined in a special biofilm culture medium (BHIG/X). The MIC and BPC for gentamicin and cefazolin were reduced by subMIC BisEDT (BisEDT MIC, 0.2-0.4 µg/ml), but not below the breakpoint for sensitivity. subMIC BisEDT enhanced the sensitivity of MRSA to gatifloxacin and cefepime close to the breakpoint for sensitivity. These strains were already sensitive to vancomycin, but were made considerably moreso in the presence of subMIC BisEDT. Generally, the MIC and BPC were reduced 2- to 5-fold with subMIC BisEDT.

TABLE 18

Antimicrobial Activity of BT-Antibiotic Combinations against MRSA

| Antibiotic | BisEDT (µg/mL) | | | | MIC Standards (µg/ml) | |
|---|---|---|---|---|---|---|
| | 0 | 0.025 | 0.05 | 0.1 | S | R |
| Gentamicin | | | | | | |
| BPC | 81 ± 41 | 63 ± 30 | 53 ± 31 | 33 ± 25 | | |
| MIC | 81 ± 40 | 60 ± 27 | 58 ± 30 | 48 ± 31 | ≤4 | ≥16 |
| Cefazolin | | | | | | |
| BPC | 109 ± 86 | 76 ± 86 | 76 ± 105 | 34 ± 28 | | |
| MIC | 93 ± 75 | 99 ± 76 | 90 ± 60 | 45 ± 32 | ≤8 | ≥32 |
| Gatifloxacin | | | | | | |
| BPC | 3.6 ± 2.6 | 2.6 ± 0.9 | 2.4 ± 1.1 | 0.9 ± 0.8 | | |
| MIC | 3.6 ± 2.6 | 4.0 ± 2.8 | 4.0 ± 2.8 | 2.4 ± 1.1 | ≤2 | ≥8 |
| Vancomycin | | | | | | |
| BPC | 2.5 ± 1.7 | 1.5 ± 0.6 | 1.3 ± 0.5 | 0.7 ± 0.4 | | |
| MIC | 2.5 ± 1.7 | 2.5 ± 1.7 | 1.5 ± 0.6 | 1.3 ± 0.5 | ≤4 | ≥32 |
| Cefepime | | | | | | |
| BPC | 24 ± 37 | 27 ± 28 | 18 ± 16 | 5.0 ± 7.3 | | |
| MIC | 45 ± 32 | 32 ± 28 | 37 ± 24 | 9.3 ± 6.1 | ≤8 | ≥32 |

12 MRSA clinical isolates were grown in BHIG/X and exposed to serial dilutions of antibiotics in the presence of 0-0.1 µg/ml BisEDT. The MIC and BPC, calculated in µg/ml, are the means±standard deviations from at least three trials. The right hand column lists the Standard MIC for antibiotic sensitivity (S) and resistance (R)

A broth dilution study of cefepime-resistant MRSA isolates is shown in Table 19. BisEDT at 0.1 µg/ml significantly enhanced the inhibitory activity of cefepime in 11 of 12 isolates. In this particular study, the data indicated synergy between BisEDT and cefepime (FIC<0.5), with many of the isolates at the breakpoint for sensitivity.

TABLE 19

Cefepime-resistant MRSA Sensitized by BisEDT
MIC for Cefepime (ug/mL) in subMIC BisEDT

| MRSA Strain # | BE 0 µg/mL MIC | BE 0.05 µg/mL MIC | BE 0.1 µg/mL MIC |
|---|---|---|---|
| 4 | 256 | 256 | 16 |
| 6 | 256 | 256 | 32 |
| 7 | 128 | 256 | 32 |
| 10 | 128 | 32 | 16 |
| 18 | 256 | 128 | 8 |
| 24 | 256 | 64 | 8 |
| 28 | 256 | 128 | 8 |
| 35 | 256 | 256 | 8 |
| 37 | 128 | 128 | 8 |
| 41 | 128 | 256 | 8 |
| 46 | 256 | 256 | 256 |
| 47 | 32 | 8 | 8 |

Twelve cefepime-resistant MRSA were tested in BHIG/X medium in polystyrene plates for sensitivity to cefepime combined with subMIC BisEDT at 37° C. for 48 h.

Results for combination studies with nafcillin or gentamicin are shown in Table 20. Combined with nafcillin, BisEDT (0.2 µg/ml) reduced the MIC90 for nafcillin by over 4-fold against MRSA (FIC, 0.74). Combined with gentamicin, BisEDT reduced the MIC90 for gentamicin over 10-fold against MRSA (FIC, 0.6). BTs reversed the resistance of all four gentamicin-resistant isolates tested to clinically relevant concentrations [Domenico et al., 2002]. The MICs for these antimicrobial agents was reduced substantially, especially for gentamicin. The broth used in these studies was Trypticase Soy Broth (TSB) with 2% glucose, which showed results similar to that seen in Mueller-Hinton II broth fortified with 1% sheep's blood.

TABLE 20

MRSA: Nafcillin or Gentamicin + BisEDT Synergy

| Strain | NAF MIC | NAF + BE MIC | Δ | GM MIC | GM + BE MIC | Δ |
|---|---|---|---|---|---|---|
| 60187-2 | 10.00 | 0.60 | 16.67 | 0.23 | 0.00 | 58.33 |
| 52446-3 | 175.00 | 40.00 | 4.38 | 10.67 | 1.50 | 7.11 |
| M1978 | 140.00 | 50.00 | 2.80 | 32.50 | 4.00 | 8.13 |
| W54793 | 130.00 | 33.33 | 3.90 | 0.25 | 0.08 | 3.13 |
| S24341 | 210.00 | 65.00 | 3.23 | 0.25 | 0.06 | 4.29 |
| H7544 | 28.33 | 15.00 | 1.89 | 0.38 | 0.09 | 4.11 |
| H72751 | 145.00 | 43.33 | 3.35 | 0.20 | 0.07 | 2.79 |
| W71630 | 131.67 | 46.67 | 2.82 | 17.67 | 3.80 | 4.65 |
| X22831 | 178.33 | 75.00 | 2.38 | | | |
| X23660 | 123.33 | 43.33 | 2.85 | 22.50 | 4.00 | 5.63 |
| O36466 | 191.67 | 93.33 | 2.05 | 0.27 | 0.04 | 6.15 |
| | | AVG Δ | 4.21 | | AVG Δ | 10.43 |

NAF or GM in µg/ml; BE at 0.2 µg/ml

*Staphylococcus epidermidis*

Figure 5:
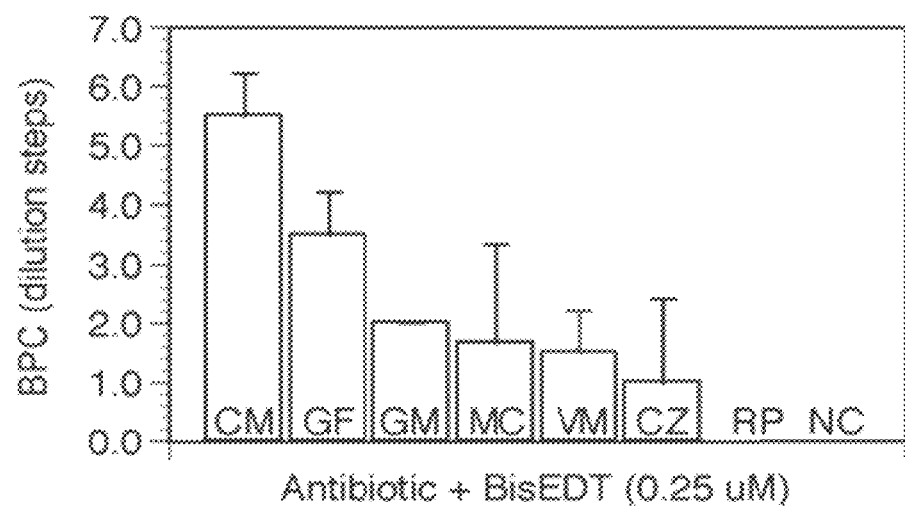
FIG. 5 shows the effect of BisEDT and antibiotics on biofilm formation. *S. epidermidis* grown in TSB+2% glucose in polystyrene plates for 48 h at 37° C. Gatifloxacin (GF), clindamycin (CM), minocycline (MC), gentamicin (GM), vancomycin (VM), cefazolin (CZ), nafcillin (NC), and rifampicin (RP). Results were expressed as the mean change in the BPC (in serial 2-fold dilution steps) at 0.25 µM BisEDT (n=3).

The activities of most classes of antibiotic were promoted in the presence of BisEDT. With regard to the BPC, clindamycin and gatifloxacin showed significantly more antibiofilm activity against *S. epidermidis* when combined with BisEDT (FIG. 5). Stated in different terms, the BPC for clindamycin, gatifloxacin and gentamicin were reduced 50-fold, 10-fold and 4-fold, respectively, in the presence of subMIC BisEDT.

Only modest decreases in the biofilm prevention concentration (BPC) were noted for minocycline, vancomycin, and cefazolin, while rifampicin and nafcillin remained unaffected at 0.05 µg/ml BisEDT. At 0.1 µg/ml BisEDT no biofilm was detected, regardless of antibiotic employed, signifying that no antagonism occurred. This BisEDT concentration was close to the MIC for *S. epidermidis* [Domenico et al., 2003] (See FIG. 5).

Figure 6:
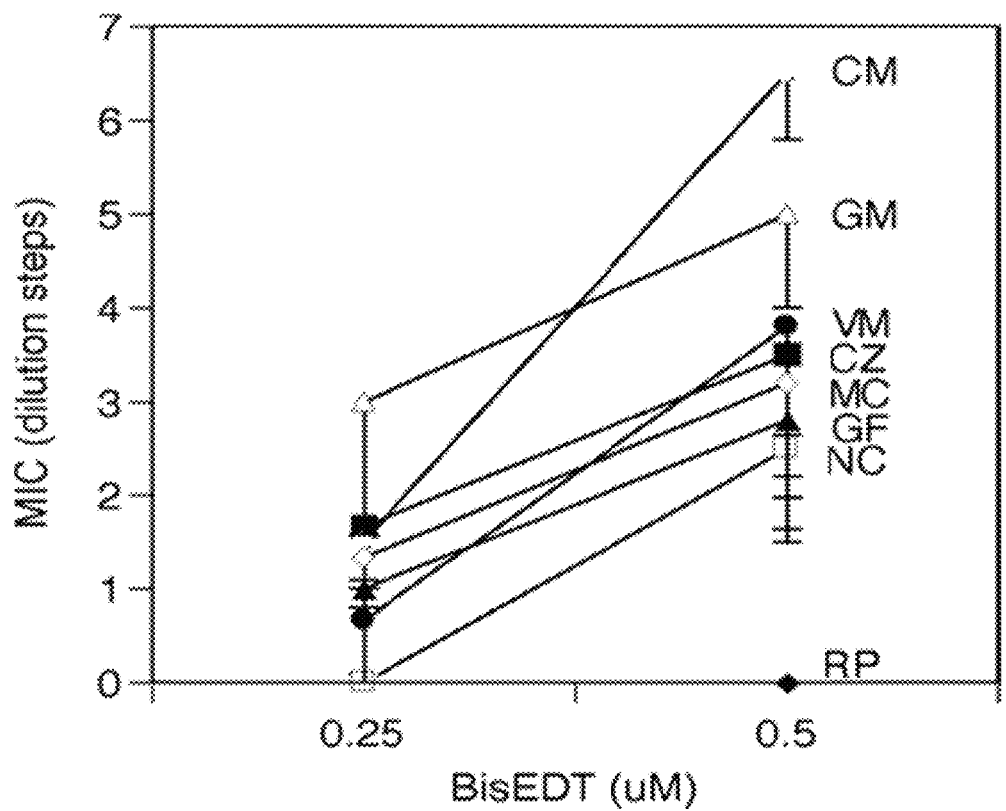
FIG. 6 shows the effect of BisEDT and antibiotics on growth of *S. epidermidis* grown in TSB plus 2% glucose for 48 h at 37° C. Results are expressed as the mean change in MIC (dilution steps) with increasing BisEDT (n=3). See legend in FIG. 5 for antibiotic definitions.

With regard to growth inhibition, seven of eight antibiotics tested were significantly enhanced in the presence of 0.1 µg/ml (0.5 µM) BisEDT against *S. epidermidis* (FIG. 6). The MIC change was most pronounced for clindamycin and gentamicin, followed by vancomycin, cefazolin, minocycline, gatifloxacin and nafcillin, with rifampicin unaffected. Of the antibiotics this strain was resistant to (NC, CZ, GM, CM), only cefazolin resistance was reversed to clinically relevant levels by BisEDT.

Minimum bactericidal concentration (MBC) for most antibiotics tested against *S. epidermidis* decreased slightly with subMIC BisEDT. Gentamicin showed the greatest reduction in MBC (4- to 16-fold), followed by cefazolin (4- to 5-fold), vancomycin and nafcillin (3- to 4-fold), minocycline and gatifloxacin (2- to 3-fold), while clindamycin and rifampicin MBC remained largely unaffected. Clindamycin is a bacteriostatic agent, which explains its lack of bactericidal activity. Cefazolin resistance was reversed with respect to the MBC [Domenico et al., 2003]. These effects were additive.

The potentiation of antimicrobial agents was also demonstrated in vivo in a graft infection rat model (Table 21). BisEDT levels as low as 0.1 µg/ml were able to promote the prevention of resistant *S. epidermidis* biofilm for 7 days.

As summarized in Table 21, implants impregnated with 0.1 µg/ml BisEDT, 10 µg/ml RIP and 10 µg/ml rifampin, alone or combined were implanted s.c. into rats. Physiological solution (1 ml) containing the MS and MR strains at $2 \times 10^7$ cfu/ml was inoculated onto the graft surface using a tuberculin syringe. All grafts were explanted at 7 days following implantation and sonicated for 5 minutes in sterile saline solution to remove the adherent bacteria. Quantitation of viable bacteria was obtained by culturing dilutions on blood agar plates. The limit of detection was approximately 10 cfu/cm$^2$.

TABLE 21

RIP, BTs, and rifampin against *S. epidermidis* in a graft infection model

| Group[a] | Graft-bonded drug[b] | Quantitative graft culture (cfu/cm$^2$) |
|---|---|---|
| No MSSE | — | <10 |
| Untreated MSSE | — | $5.0 \times 10^7 \pm 7.7 \times 10^6$ |
| MS1[c] | RIP | $4.3 \times 10^2 \pm 1.2 \times 10^2$ |
| MS2[c] | BTs | $5.8 \times 10^2 \pm 0.9 \times 10^2$ |
| MS3[c] | Rifampin | $5.9 \times 10^3 \pm 1.8 \times 10^3$ |
| MS4[cd] | RIP plus BTs | <10 |
| MS5[cd] | RIP plus rifampin | $2.0 \times 10^1 \pm 0.6 \times 10^1$ |
| MS6[cd] | BTs plus rifampin | $1.9 \times 10^1 \pm 0.4 \times 10^1$ |
| No MRSE | — | <10 |
| Untreated MRSE | — | $7.8 \times 10^7 \pm 2.0 \times 10^7$ |
| MR1[c] | RIP | $6.7 \times 10^2 \pm 2.1 \times 10^2$ |
| MR2[c] | BTs | $6.2 \times 10^2 \pm 2.3 \times 10^2$ |
| MR3[c] | Rifampin | $7.6 \times 10^4 \pm 2.1 \times 10^4$ |
| MR4[ce] | RIP plus BTs | <10 |
| MR5[c] | RIP plus rifampin | $4.3 \times 10^1 \pm 1.1 \times 10^1$ |
| MR6[c] | BTs plus rifampin | $3.0 \times 10^1 \pm 1.1 \times 10^1$ |

[a]Each group had 15 animals; MS, methicillin-susceptible *S. epidermidis*; MR, methicillin-resistant *S. epidermidis*
[b]Dacron graft segments impregnated with 0.1 mg/l of BTs, 10 mg/l of RIP, 10 mg/l of rifampin
[c]Statistically significant when compared with control groups MS and MR
[d]Statistically significant when compared with MS3 group
[e]Statistically significant when compared with MR1, MR2, and MR3 groups Gram-Negative Bacteria.

Tobramycin activity against resistant *Pseudomonas aeruginosa* was enhanced several-fold with subMIC BisEDT (Table 22). In these trials, the MIC was defined more precisely as the IC$_{24}$.

TABLE 22

Tobramycin-resistant *P. aeruginosa*: BisEDT Effect

| Strain | NN MIC (µg/ml) | BE MIC (µg/ml) | NN + BE MIC (µg/ml) | Δ |
|---|---|---|---|---|
| PA Xen5 | 0.3 | 0.9 | 0.2 | 1.7 |
| Agr PA E | 115.0 | 0.9 | 70.0 | 1.6 |
| Agr PA I | 200.0 | 1.0 | 73.0 | 2.7 |
| Agr PA K | 4.8 | 0.86 | 3.0 | 1.6 |
| Agr PA O | 130.0 | 0.98 | 20.5 | 6.3 |

Resistant strains of *P. aeruginosa* were cultured in Mueller-Hinton II broth at 37° C. in the presence of tobramycin (NN) and BisEDT (BE; 0.33 µg/ml). The MIC was determined as the antibiotic concentration that inhibited growth for 24±1 h.

Against tobramycin-resistant *Burkholderia cepacia*, 0.4 µg/ml BisEDT rendered seven of 10 isolates tobramycin sensitive (mean FIC; 0.48), and reduced the MIC$_{90}$ by 10-fold (Table 23). Both the MIC and MBC of tobramycin were reduced significantly to achievable levels against 50 clinical *Burkholderia cepacia* isolates with subMIC BisEDT [Veloira et al., 2003]. BisEDT and tobramycin in liposomal form have proven highly synergistic against *P. aeruginosa*. (Halwani et al., 2008; Halwani et al., 2009).

TABLE 23

Tobramycin and BisEDT versus *B. cepacia*

| | MIC for | | | |
|---|---|---|---|---|
| Strain | Tobramycin (µg/ml) | BisEDT (µg/ml) | Tobramycin (BisEDT at 0.4 µg/ml) | FIC Index |
| *B. multivorans* | | | | |
| HI 2249 | 256 | 0.4 | a | a |
| HI 2229 | 64 | 0.8 | 8 | 0.63 |
| AU 0267 | 128 | 0.8 | 2 | 0.52 |
| AU 0259 | 1024 | 1.6 | 256 | 0.50 |
| HI 2255 | 64 | 1.6 | 8 | 0.38 |
| *B. cenocepacia* | | | | |
| HI 2711 | 256 | 0.4 | a | a |
| AU 0284 | 512 | 0.4 | a | a |
| AU 0273 | 512 | 1.6 | 32 | 0.31 |
| HI2253 | 64 | 1.6 | 16 | 0.50 |
| HI 2147 | 512 | 1.6 | 8 | 0.27 | a The three strains inhibited by BisEDT at 0.4 µg/ml were excluded from further study.
FIC Index ≤0.5 indicates synergy.
FICI >0.5 and <1.0 indicates enhancement.

Chloramphenicol and ampicillin resistant *Escherichia coli* were made sensitive to these drugs by the addition of subMIC BisEDT (Table 24).

TABLE 24

Chloramphenicol/Ampicillin Resistant *E. coli*: BisEDT Effect

| Strain | Drug | Drug MIC (µg/ml) | BE MIC (µg/ml) | Drug + BE MIC (µg/ml) | Δ |
|---|---|---|---|---|---|
| MC4100/TN9 | CM | 220.0 | 0.6 | 12.7 | 17.4 |
| MC4100/P9 | AMP | 285.0 | 0.5 | 49.0 | 5.8 |
| MC4100 | AMP | 141.7 | 0.6 | 35.0 | 4.0 |

Resistant strains of *E. coli* were cultured in Mueller-Hinton II broth at 37° C. in the presence of chloramphenicol (CM) or ampicillin (AMP) and BisEDT alone or in combination (BE; 0.33 µg/ml). The MIC was determined as the antibiotic concentration that inhibited growth for 24±1 h.

Tetracycline resistant *Escherichia coli* were made sensitive to doxycycline by the addition of subMIC BisEDT (Table 25). The combination exhibited synergy against the TET M and TET D strains (FIC≤0.5), with additive effects against the TET A and TET B strains.

TABLE 25

Tetracycline Resistant *E. Coli*: BisEDT Effect

| Strain | DOX MIC (µg/ml) | BE MIC (µg/ml) | DOX + BE MIC (µg/ml) | Δ |
|---|---|---|---|---|
| TET M | 16.5 ± 1.3 | 0.85 | 4.5 ± 2.7 | 4.0 |
| TET D | 20.5 ± 1.1 | 0.85 | 0.03 ± 0.0 | 820.0 |
| TET A | 15.0 ± 1.8 | 0.40 | 10.0 ± 1.0 | 1.5 |
| TET B | 20.1 ± 2.4 | 0.60 | 10.3 ± 3.2 | 2.0 |

Resistant strains of *E. coli* were cultured in Mueller-Hinton II broth at 37° C. in the presence of doxycycline (DOX) and BisEDT alone or in combination (BE; 0.33 µg/ml). The MIC was determined as the antibiotic concentration that inhibited growth for 24±1 h.

REFERENCES

Domenico P, R O'Leary, B A Cunha. 1992. Differential effect of bismuth and salicylate compounds on antibiotic sensitivity of *Pseudomonas aeruginosa*. *Eur J Clin Microbiol Infec Dis* 11:170-175; Domenico P, D Parikh, B A Cunha. 1994. Bismuth modulation of antibiotic activity against gastrointestinal bacterial pathogens. *Med Microbiol Lett* 3:114-119; Domenico P, Kazzaz J A, Davis J M, Niederman M S. 2002. Subinhibitory bismuth ethanedithiol (BisEDT) sensitizes resistant *Staphylococcus aureus* to nafcillin or gentamicin. Annual Meeting, ASM, Salt Lake City, Utah; Domenico P, Kazzaz J A, Davis J M. 2003. Combating antibiotic resistance with bismuth-thiols. *Research Advances in Antimicrob Agents Chemother* 3:79-85; Domenico P, E Gurzenda, A Giacometti, O Cirioni, R Ghiselli, F Orlando, M Korem, V Saba, G Scalise, N Balaban. 2004. BisEDT and RIP act in synergy to prevent graft infections by resistant staphylococci. *Peptides* 25:2047-2053; Halwani M, Blomme S, Suntres Z E, Alipour M, Azghani A O, Kumar A, Omri A. 2008. Liposomal bismuth-ethanedithiol formulation enhances antimicrobial activity of tobramycin. *Intl J Pharmaceut* 358:278-84; Halwani M, Hebert S, Suntres Z E, Lafrenie R M, Azghani A O, Omri A. 2009. Bismuth-thiol incorporation enhances biological activities of liposomal tobramycin against bacterial biofilm and quorum sensing molecules production by *Pseudomonas aeruginosa*. *Int J Pharmaceut* 373:141-6; Veloira W G, Gurzenda E M, Domenico P, Davis J M, Kazzaz J A. 2003. Synergy of tobramycin and bismuth thiols against *Burkholderia cepacia*. *J Antimicrob Chemother* 52:915-919.

Example 9

Microparticulate BT-Antibiotic Enhancing and Synergizing Activities

This example shows that the microparticulate bismuth thiol BisEDT promotes antibiotic activity through enhancing and/or synergizing interactions with specific antibiotics against specific microbial target organisms. Single-point data for each indicated combination in Table 26 were generated essentially according to the methods used in Example 8.

TABLE 26

FICI Values for single-point BisEDT-antibiotic combinations

| Antibiotic | SA 100 | MRSA 773 | E Fc 3121 | SP 1195 | PRSP 5348 | EC 102 | EC 2232 | KP 1231 | PA 1380 | Bcep 1756 | Bmult 5665 | Abau 2594 | Msmeg 817 |
|---|---|---|---|---|---|---|---|---|---|---|---|---|---|
| Oxacillin | 1.28 | 2.28 | 0.92 | | 1.03 | | | | | | | | |
| Piperacillin | 0.57 | 1.28 | 1.11 | | 1.11 | 0.87 | 1.29 | 2.23 | 0.67 | 1.12 | 1.12 | 1.12 | |
| Cefuroxime | 1.11 | 4.23 | 1.11 | | 1.03 | | | | | | | | |
| Cefotaxime | 1.11 | 2.23 | 0.73 | 1.11 | 1.11 | 1.37 | 1.29 | 0.61 | 0.64 | 1.29 | 1.11 | 1.29 | |
| Cefepime | | | | | | 0.87 | 0.96 | 1.11 | 0.62 | 1.34 | 0.96 | 0.71 | |
| Imipenem | 0.67 | 1.48 | 0.73 | 0.92 | 0.43 | 1.11 | 1.29 | 1.23 | 1.12 | 0.73 | 1.23 | 0.81 | |
| Aztreonam | | | | | | 0.74 | 1.29 | 0.73 | 0.55 | 0.67 | 0.96 | 0.87 | |
| Streptomycin | | 0.95 | 0.61 | | 0.66 | | 1.29 | 1.04 | 1.98 | 1.37 | 1.12 | 2.62 | 1.13 |
| Tobramycin | 0.73 | 0.78 | 0.47 | | 0.57 | | 0.96 | 0.87 | 1.29 | 0.91 | 0.67 | 1.12 | |
| Tetracycline | 0.89 | 1.23 | 0.92 | 1.23 | 0.34 | 0.62 | 0.79 | 1.29 | 1.29 | 1.96 | 1.12 | 1.12 | |
| Minocycline | 1.09 | 1.23 | 1.11 | | 0.46 | 1.37 | 1.04 | 1.29 | 0.99 | 2.23 | 1.12 | 1.29 | |
| Ciprofloxacin | | | | | | 1.14 | 1.29 | 1.29 | 2.75 | 2.23 | 2.29 | 1.04 | |
| Levofloxacin | 1.23 | 1.11 | 1.08 | 0.95 | 0.70 | | | | | | | | |
| Erythromycin | 1.28 | 0.67 | 0.92 | 0.78 | 1.03 | | | | | | | | |
| Linezolid | 1.23 | 1.23 | 1.23 | 1.01 | 1.11 | | | | | | | | |
| Phosphomycin | | 0.61 | 1.23 | | 1.45 | | 1.96 | 1.02 | 1.86 | 1.29 | 1.23 | 1.12 | |
| Capreomycin | | | | | | | | | | | | | 0.75 |
| Isoniazid | | | | | | | | | | | | | 0.88 |

SA, *Staphylococcus aureus*; MRSA, methicillin-resistant *Staphylococcus aureus*; E Fc, *Enterococcus faecalis*; SP, *Streptococcus pneumoniae*; PRSP, penicillin-resistant *Streptococcus pneumoniae*; EC, *Escherichia coli*; KP, *Klebsiella pneumoniae*; PA, *Pseudomonas aeruginosa*; Bcep, *Burkholderia cepacia*; Bmult, *Bukholderia multivorans*; Abau, *Acinetobacter baumanii*; Msmeg, *Mycobacterium smegmatis*.

Example 10

Microparticulate BT-Antibiotic Enhancing and Synergizing Activities

The effects of combinations of microparticulate Bis-EDT and four Bis-EDT analogs prepared as described above, and other agents against representative strains of several Gram-negative pathogenic bacteria were tested. A modification of a common laboratory method was used to determine synergism (FICI≤0.5), enhancement (0.5<FICI≤1.0), antagonism (FICI>4.0) and indifference (1.0<FICI≤4.0) used fractional inhibitory concentrations (FICs) and FIC indices (FICI) (Eliopoulos G and R Moellering. 1991. Antimicrobial combinations. In *Antibiotics in Laboratory Medicine, Third Edition*, edited by V Lorian. Williams and Wilkins, Baltimore, Md., pp. 432-492; Odds, 2003 *J. Antimicrob. Chemother.* 52(1):1). The checkerboard technique was used to determine FIC indices and was employed in this study.

TABLE 27

| Test Components | | | | |
|---|---|---|---|---|
| Test Cpd | Lot No. | Solvent | FIC Highest Stock Concentration (μg/mL) | Conc. Range Tested in FIC (μg/mL) |
| Bis-EDT | MB-1B-3 | DMSO | 320 | 0.12-8 |
| Bis-EDT (analog) | MB-2B | DMSO | 320 | 0.12-8 |

TABLE 27-continued

Test Components

| Test Cpd | Lot No. | Solvent | FIC Highest Stock Concentration (µg/mL) | Conc. Range Tested in FIC (µg/mL) |
|---|---|---|---|---|
| Bis-EDT (analog) | MB-8-2 | DMSO | 320 | 0.12-8 |
| Bis-EDT (analog) | MB-11 | DMSO | 320 | 0.12-8 |
| Bis-EDT (analog) | MB-15 | DMSO | 320 | 0.12-8 |
| Aztreonam | 095K1324 (Sigma) | 10% DMSO | 2,560 | 0.06-64 |
| Cefepime HCl | GOD116 (USP) | $dH_2O$ | 2,560 | 0.06-64 |
| Cefotaxime | 084K0674 (Sigma) | $dH_2O$ | 640 | 0.015-16 |
| Piperacillin | 014K1362 (Sigma) | $dH_2O$ | 2,560 | 0.06-64 |

Stock solutions of all test articles were prepared at 40× the final target concentration in the appropriate solvent. All test articles were in solution under these conditions. The final drug concentrations in the FIC assay plates were set to bracket the MIC value of each agent for each test organism, unless the strain was totally resistant to the test agent. The concentration ranges tested are displayed in Table 27. The test organisms were originally received from clinical sources, or from the American Type Culture Collection. Upon receipt, the isolates were streaked onto Tryptic Soy Agar II (TSA). Colonies were harvested from these plates and a cell suspension was prepared in an appropriate broth growth medium containing cryoprotectant. Aliquots were then frozen at −80° C. The frozen seeds of the organisms to be tested in a given assay were thawed, streaked for isolation onto TSA plates, and incubated at 35° C. All organisms were tested in Mueller Hinton II Broth (Becton Dickinson, Lot No. 9044411). The broth was prepared at 1.05× normal weight/volume to offset the 5% volume of the drugs in the final test plates.

Minimal Inhibitory Concentration (MIC) values were previously determined using the broth microdilution method for aerobic bacteria (Clinical and Laboratory Standards Institute (CLSI). *Methods for Dilution Antimicrobial Susceptibility Tests for Bacteria That Grow Aerobically; Approved Standard—Eighth Edition*. CLSI document M07-A8 [ISBN 1-56238-689-1]. Clinical and Laboratory Standards Institute, 940 West Valley Road, Suite 1400, Wayne, Pa. 19087-1898 USA, 2009.).

FIC values were determined using a broth microdilution method previously described (Sweeney et al., 2003 *Antimicrob. Agents Chemother.* 47(6):1902-1906). To prepare the test plates, automated liquid handlers (MULTIDROP® 384, Labsystems, Helsinki, Finland; BIOMEK® 2000 and MULTIMEK™ 96, Beckman Coulter, Fullerton Calif.) were used to conduct serial dilutions and liquid transfers.

The appropriate wells of standard 96-well microdilution plates (FALCON™ 3918) were filled with 150 µL of the appropriate solvent in columns 2-12 using the MULTIDROP® 384. Three hundred microliters of each secondary test drug was added to each well in Column 1 of the plates. These plates were used to prepare the drug "mother plates" which provided the serial drug dilutions for the drug combination plates. The BIOMEK® 2000 was used to transfer 150 µL of each secondary drug solution (40×) from the wells in Column 1 of the mother plate and to make eleven 2-fold serial dilutions. Mother plates of Bis-EDT (and analogs) were serial diluted top to bottom by hand, using a multichannel pipette. Two mother plates, one for each secondary drug and one for Bis-EDT (or analogs), were combined to form a "checkerboard" pattern by transfer of equal volumes (using a multichannel pipette) to the drug combination plate. Row H and Column 12 each contained serial dilutions of one of the agents alone for determination of the MIC.

The "daughter plates" were loaded with 180 µL of test medium using the MULTIDROP® 384. Then, the MULTIMEK™ 96 was used to transfer 10 µL of drug solution from each well of the drug combination mother plate to each corresponding well of the daughter plate in a single step. Finally, the daughter plates were inoculated with test organism. Standardized inoculum of each organism was prepared per published guidelines (CLSI, 2009). For all isolates, the inoculum for each organism was dispensed into sterile reservoirs divided by length (Beckman Coulter), and the BIOMEK® 2000 was used to inoculate the plates. The instrument delivered 10 µL of standardized inoculum into each well to yield a final cell concentration in the daughter plates of approximately $5 \times 10^5$ colony-forming-units/mL.

The test format resulted in the creation of an 8×12 checkerboard where each compound was tested alone (Column 12 and Row H) and in combination at varying ratios of drug concentration. All organism plates were stacked three high, covered with a lid on the top plate, placed in plastic bags, and incubated at 35° C. for approximately 20 hours. Following incubation, the microplates were removed from the incubators and viewed from the bottom using a plate viewer sold under the trademark SCIENCEWARE® (Bet-Art Products Corp., South Wayne, N.J.). Prepared reading sheets were marked for the MIC of drug 1 (row H), the MIC of drug 2 (column 12) and the wells of the growth-no growth interface.

An EXCEL® program (Microsoft, Redmond, Wash.) was used to determine the FIC according to the formula: (MIC of Compound 1 in combination/MIC of Compound 1 alone)+ (MIC of Compound 2 in combination/MIC of Compound 2 alone). The FICI for the checkerboard was calculated from the individual FICs by the formula: $(FIC_1+FIC_2+FIC_n)/n$, where n=number of individual wells per plate for which FICs were calculated. In instances where an agent alone yielded an off-scale MIC result, the next highest concentration was used as the MIC value in the FIC calculation.

Microparticulate Bis-EDT, the four microparticulate BT analogs, and all of the other agents (and combinations of agents) were soluble at all final test concentrations. The MIC and FICI values that were determined are presented in the Tables below.

TABLE 28

Summary of Minimum Inhibitory Concentration and Fractional Inhibitory Concentration Results for MB-1B-3 and Piperacillin

| | Compound 1 | | Compound 2 | | |
|---|---|---|---|---|---|
| Organism[1] | Name | MIC[1] (µg/mL) Alone | Name | MIC (µg/mL) Alone | FICI[2] |
| *P. aeruginosa* 1381 | MB-1B-3 | 1 | Piperacillin | >64 | 0.83 |
| *P. aeruginosa* 1384 | | 1 | | 8 | 0.96 |
| *P. aeruginosa* 1474 | | 1 | | 8 | 0.71 |
| *P. aeruginosa* 1479 | | 0.5 | | 8 | 1.12 |
| *P. aeruginosa* 2566 | | 0.5 | | 32 | 1.37 |
| *P. aeruginosa* 2568 | | 1 | | 8 | 0.71 |
| *P. aeruginosa* 103 | | 1 | | 8 | 0.79 |

[1]MIC, Minimum Inhibitory Concentration
[2]FICI, Fractional Inhibitory Concentration Index

TABLE 29

Summary of Minimum Inhibitory Concentration and Fractional Inhibitory Concentration Results for MB-1B-3 and Aztreonam

| | Compound 1 | | Compound 2 | | |
|---|---|---|---|---|---|
| Organism[1] | Name | MIC[1] (µg/mL) Alone | Name | MIC (µg/mL) Alone | FICI[2] |
| P. aeruginosa 1381 | MB-1B-3 | 1 | Aztreonam | 32 | 1.04 |
| P. aeruginosa 1384 | | 1 | | 8 | 0.71 |
| P. aeruginosa 1474 | | 1 | | 8 | 0.71 |
| P. aeruginosa 1479 | | 0.5 | | 8 | 0.87 |
| P. aeruginosa 2566 | | 0.5 | | 16 | 1.37 |
| P. aeruginosa 2568 | | 1 | | 8 | 0.71 |
| P. aeruginosa 103 | | 1 | | 4 | 1.29 |

[1]MIC, Minimum Inhibitory Concentration
[2]FICI, Fractional Inhibitory Concentration Index

TABLE 30

Summary of Minimum Inhibitory Concentration and Fractional Inhibitory Concentration Results for MB-15 and Piperacillin

| | Compound 1 | | Compound 2 | | |
|---|---|---|---|---|---|
| Organism[1] | Name | MIC[1] (µg/mL) Alone | Name | MIC (µg/mL) Alone | FICI[2] |
| P. aeruginosa 1381 | MB-15 | 1 | Piperacillin | >64 | 1.29 |
| P. aeruginosa 1384 | | 1 | | 16 | 0.71 |
| P. aeruginosa 1474 | | 1 | | 8 | 1.12 |
| P. aeruginosa 1479 | | 1 | | 8 | 1.29 |
| P. aeruginosa 2566 | | 1 | | 32 | 1.04 |
| P. aeruginosa 2568 | | 1 | | 8 | 1.12 |
| P. aeruginosa 103 | | 2 | | 8 | 0.73 |

[1]MIC, Minimum Inhibitory Concentration
[2]FICI, Fractional Inhibitory Concentration Index

TABLE 31

Summary of Minimum Inhibitory Concentration and Fractional Inhibitory Concentration Results for MB-15 and Aztreonam

| | Compound 1 | | Compound 2 | | |
|---|---|---|---|---|---|
| Organism[1] | Name | MIC[1] (µg/mL) Alone | Name | MIC (µg/mL) Alone | FICI[2] |
| P. aeruginosa 1381 | MB-15 | 2 | Aztreonam | 32 | 1.11 |
| P. aeruginosa 1384 | | 1 | | 8 | 0.79 |
| P. aeruginosa 1474 | | 1 | | 8 | 0.71 |
| P. aeruginosa 1479 | | 2 | | 8 | 0.67 |
| P. aeruginosa 2566 | | 0.5 | | 16 | 1.12 |
| P. aeruginosa 2568 | | 1 | | 8 | 0.79 |
| P. aeruginosa 103 | | 2 | | 4 | 1.23 |

[1]MIC, Minimum Inhibitory Concentration
[2]FICI, Fractional Inhibitory Concentration Index

TABLE 32

Summary of Minimum Inhibitory Concentration and Fractional Inhibitory Concentration Results for MB-8-2 and Piperacillin

| | Compound 1 | | Compound 2 | | |
|---|---|---|---|---|---|
| Organism[1] | Name | MIC[1] (µg/mL) Alone | Name | MIC (µg/mL) Alone | FICI[2] |
| P. aeruginosa 1381 | MB-8-2 | 2 | Piperacillin | >64 | 1.23 |
| P. aeruginosa 1384 | | 2 | | 16 | 0.73 |
| P. aeruginosa 1474 | | 2 | | 8 | 1.23 |
| P. aeruginosa 1479 | | 2 | | 8 | 1.23 |
| P. aeruginosa 2566 | | 2 | | 32 | 1.23 |
| P. aeruginosa 2568 | | 2 | | 8 | 0.98 |
| P. aeruginosa 103 | | 4 | | 8 | 1.19 |

[1]MIC, Minimum Inhibitory Concentration
[2]FICI, Fractional Inhibitory Concentration Index

TABLE 33

Summary of Minimum Inhibitory Concentration and Fractional Inhibitory Concentration Results for MB-8-2 and Aztreonam

| | Compound 1 | | Compound 2 | | |
|---|---|---|---|---|---|
| Organism[1] | Name | MIC[1] (µg/mL) Alone | Name | MIC (µg/mL) Alone | FICI[2] |
| P. aeruginosa 1381 | MB-8-2 | 2 | Aztreonam | 32 | 1.11 |
| P. aeruginosa 1384 | | 2 | | 8 | 1.11 |
| P. aeruginosa 1474 | | 2 | | 8 | 0.73 |
| P. aeruginosa 1479 | | 2 | | 8 | 0.98 |
| P. aeruginosa 2566 | | 2 | | 16 | 1.23 |
| P. aeruginosa 2568 | | 2 | | 8 | 0.98 |
| P. aeruginosa 103 | | 4 | | 8 | 1.19 |

[1]MIC, Minimum Inhibitory Concentration
[2]FICI, Fractional Inhibitory Concentration Index

TABLE 34

Summary of Minimum Inhibitory Concentration and Fractional Inhibitory Concentration Results for MB-11 and Piperacillin

| | Compound 1 | | Compound 2 | | |
|---|---|---|---|---|---|
| Organism[1] | Name | MIC[1] (µg/mL) Alone | Name | MIC (µg/mL) Alone | FICI[2] |
| P. aeruginosa 1381 | MB-11 | 1 | Piperacillin | >64 | 1.12 |
| P. aeruginosa 1384 | | 1 | | 16 | 0.71 |
| P. aeruginosa 1474 | | 1 | | 8 | 1.12 |
| P. aeruginosa 1479 | | 1 | | 8 | 1.29 |
| P. aeruginosa 2566 | | 0.5 | | 32 | 1.12 |
| P. aeruginosa 2568 | | 1 | | 8 | 1.12 |
| P. aeruginosa 103 | | 2 | | 8 | 1.11 |

[1]MIC, Minimum Inhibitory Concentration
[2]FICI, Fractional Inhibitory Concentration Index

TABLE 35

Summary of Minimum Inhibitory Concentration and Fractional Inhibitory Concentration Results for MB-11 and Aztreonam

| | Compound 1 | | Compound 2 | | |
|---|---|---|---|---|---|
| Organism[1] | Name | MIC[1] (µg/mL) Alone | Name | MIC (µg/mL) Alone | FICI[2] |
| P. aeruginosa 1381 | MB-11 | 2 | Aztreonam | 32 | 0.92 |
| P. aeruginosa 1384 | | 1 | | 8 | 0.96 |
| P. aeruginosa 1474 | | 1 | | 8 | 0.71 |

TABLE 35-continued

Summary of Minimum Inhibitory Concentration and Fractional Inhibitory Concentration Results for MB-11 and Aztreonam

| | Compound 1 | | Compound 2 | | |
|---|---|---|---|---|---|
| Organism[1] | Name | MIC[1] (µg/mL) Alone | Name | MIC (µg/mL) Alone | FICI[2] |
| P. aeruginosa 1479 | | 1 | | 8 | 0.79 |
| P. aeruginosa 2566 | | 0.5 | | 16 | 1.12 |
| P. aeruginosa 2568 | | 1 | | 8 | 0.96 |
| P. aeruginosa 103 | | 2 | | 8 | 1.11 |

[1]MIC, Minimum Inhibitory Concentration
[2]FICI, Fractional Inhibitory Concentration Index

TABLE 36

Summary of Minimum Inhibitory Concentration and Fractional Inhibitory Concentration Results for MB-2B and Piperacillin

| | Compound 1 | | Compound 2 | | |
|---|---|---|---|---|---|
| Organism[1] | Name | MIC[1] (µg/mL) Alone | Name | MIC (µg/mL) Alone | FICI[2] |
| P. aeruginosa 1381 | MB-2B | 2 | Piperacillin | >64 | 1.02 |
| P. aeruginosa 1384 | | 8 | | 16 | 0.79 |
| P. aeruginosa 1474 | | 8 | | 8 | 0.91 |
| P. aeruginosa 1479 | | 8 | | 8 | 1.08 |
| P. aeruginosa 2566 | | 8 | | 32 | 1.04 |
| P. aeruginosa 2568 | | 8 | | 8 | 0.97 |
| P. aeruginosa 103 | | 8 | | 8 | 1.16 |

[1]MIC, Minimum Inhibitory Concentration
[2]FICI, Fractional Inhibitory Concentration Index

TABLE 37

Summary of Minimum Inhibitory Concentration and Fractional Inhibitory Concentration Results for MB-2B and Aztreonam

| | Compound 1 | | Compound 2 | | |
|---|---|---|---|---|---|
| Organism[1] | Name | MIC[1] (µg/mL) Alone | Name | MIC (µg/mL) Alone | FICI[2] |
| P. aeruginosa 1381 | MB-2B | 8 | Aztreonam | 64 | 0.89 |
| P. aeruginosa 1384 | | 8 | | 8 | 0.91 |
| P. aeruginosa 1474 | | 8 | | 8 | 0.54 |
| P. aeruginosa 1479 | | 8 | | 8 | 0.87 |
| P. aeruginosa 2566 | | 8 | | 16 | 0.91 |
| P. aeruginosa 2568 | | 8 | | 8 | 0.87 |
| P. aeruginosa 103 | | 8 | | 8 | 1.08 |

[1]MIC, Minimum Inhibitory Concentration
[2]FICI, Fractional Inhibitory Concentration Index

TABLE 38

Summary of Minimum Inhibitory Concentration and Fractional Inhibitory Concentration Results for MB-1B-3 and Cefotaxime

| | Compound 1 | | Compound 2 | | |
|---|---|---|---|---|---|
| Organism[1] | Name | MIC[1] (µg/mL) Alone | Name | MIC (µg/mL) Alone | FICI[2] |
| K. pneumoniae 1346 | MB-1B-3 | 2 | Cefotaxime | 0.06 | 1.23 |
| K. pneumoniae 1355 | | 1 | | 0.06 | 2.29 |
| K. pneumoniae 2238 | | 1 | | 16 | 1.29 |
| K. pneumoniae 2541 | | 2 | | 0.12 | 1.23 |
| K. pneumoniae 2546 | | 1 | | 0.25 | 1.12 |
| K. pneumoniae 2549 | | 1 | | 0.12 | 0.79 |
| P. aeruginosa 103 | | 1 | | 16 | 0.96 |

[1]MIC, Minimum Inhibitory Concentration
[2]FICI, Fractional Inhibitory Concentration Index

TABLE 39

Summary of Minimum Inhibitory Concentration and Fractional Inhibitory Concentration Results for MB-1B-3 and Cefepime

| | Compound 1 | | Compound 2 | | |
|---|---|---|---|---|---|
| Organism[1] | Name | MIC[1] (µg/mL) Alone | Name | MIC (µg/mL) Alone | FICI[2] |
| P. aeruginosa 1381 | MB-1B-3 | 1 | Cefepime | 32 | 1.29 |
| P. aeruginosa 1384 | | 1 | | 2 | 0.79 |
| P. aeruginosa 1474 | | 1 | | 2 | 0.79 |
| P. aeruginosa 1479 | | 1 | | 4 | 1.12 |
| P. aeruginosa 2566 | | 0.5 | | 8 | 1.37 |
| P. aeruginosa 2568 | | 1 | | 2 | 0.79 |
| P. aeruginosa 103 | | 1 | | 2 | 0.71 |

[1]MIC, Minimum Inhibitory Concentration
[2]FICI, Fractional Inhibitory Concentration Index

TABLE 40

Summary of Minimum Inhibitory Concentration and Fractional Inhibitory Concentration Results for MB-15 and Cefotaxime

| | Compound 1 | | Compound 2 | | |
|---|---|---|---|---|---|
| Organism[1] | Name | MIC[1] (µg/mL) Alone | Name | MIC (µg/mL) Alone | FICI[2] |
| K. pneumoniae 1346 | MB-15 | 2 | Cefotaxime | 0.06 | 1.23 |
| K. pneumoniae 1355 | | 1 | | 0.12 | 2.37 |
| K. pneumoniae 2238 | | 2 | | 16 | 1.23 |
| K. pneumoniae 2541 | | 2 | | 0.12 | 1.23 |
| K. pneumoniae 2546 | | 2 | | 0.25 | 0.97 |
| K. pneumoniae 2549 | | 2 | | 0.06 | 1.23 |
| P. aeruginosa 103 | | 1 | | 16 | 0.96 |

[1]MIC, Minimum Inhibitory Concentration
[2]FICI, Fractional Inhibitory Concentration Index

TABLE 41

Summary of Minimum Inhibitory Concentration and Fractional Inhibitory Concentration Results for MB-15 and Cefepime

| | Compound 1 | | Compound 2 | | |
|---|---|---|---|---|---|
| Organism[1] | Name | MIC[1] (µg/mL) Alone | Name | MIC (µg/mL) Alone | FICI[2] |
| P. aeruginosa 1381 | MB-15 | 1 | Cefepime | 32 | 1.29 |
| P. aeruginosa 1384 | | 1 | | 2 | 0.79 |
| P. aeruginosa 1474 | | 1 | | 2 | 1.12 |
| P. aeruginosa 1479 | | 1 | | 4 | 1.12 |
| P. aeruginosa 2566 | | 0.5 | | 8 | 1.37 |
| P. aeruginosa 2568 | | 1 | | 2 | 1.12 |
| P. aeruginosa 103 | | 1 | | 1 | 1.12 |

[1]MIC, Minimum Inhibitory Concentration
[2]FICI, Fractional Inhibitory Concentration Index

TABLE 42

Summary of Minimum Inhibitory Concentration and Fractional Inhibitory Concentration Results for MB-8-2 and Cefotaxime

| | Compound 1 | | Compound 2 | | |
|---|---|---|---|---|---|
| Organism[1] | Name | MIC[1] (µg/mL) Alone | Name | MIC (µg/mL) Alone | FICI[2] |
| K. pneumoniae 1346 | MB-8-2 | 0.5 | Cefotaxime | 0.06 | 1.37 |
| K. pneumoniae 1355 | | 0.5 | | 0.06 | 1.37 |
| K. pneumoniae 2238 | | 0.5 | | 16 | 1.37 |
| K. pneumoniae 2541 | | 1 | | 0.12 | 1.12 |
| K. pneumoniae 2546 | | 1 | | 0.25 | 1.29 |
| K. pneumoniae 2549 | | 1 | | 0.06 | 1.12 |
| P. aeruginosa 103 | | 2 | | 16 | 1.11 |

[1]MIC, Minimum Inhibitory Concentration
[2]FICI, Fractional Inhibitory Concentration Index

TABLE 43

Summary of Minimum Inhibitory Concentration and Fractional Inhibitory Concentration Results for MB-8-2 and Cefepime

| | Compound 1 | | Compound 2 | | |
|---|---|---|---|---|---|
| Organism[1] | Name | MIC[1] (µg/mL) Alone | Name | MIC (µg/mL) Alone | FICI[2] |
| P. aeruginosa 1381 | MB-8-2 | 2 | Cefepime | 32 | 1.23 |
| P. aeruginosa 1384 | | 2 | | 2 | 0.80 |
| P. aeruginosa 1474 | | 2 | | 2 | 1.11 |
| P. aeruginosa 1479 | | 2 | | 4 | 1.23 |
| P. aeruginosa 2566 | | 2 | | 8 | 1.23 |
| P. aeruginosa 2568 | | 2 | | 2 | 0.98 |
| P. aeruginosa 103 | | 2 | | 1 | 1.11 |

[1]MIC, Minimum Inhibitory Concentration
[2]FICI, Fractional Inhibitory Concentration Index

TABLE 44

Summary of Minimum Inhibitory Concentration and Fractional Inhibitory Concentration Results for MB-11 and Cefotaxime

| | Compound 1 | | Compound 2 | | |
|---|---|---|---|---|---|
| Organism[1] | Name | MIC[1] (µg/mL) Alone | Name | MIC (µg/mL) Alone | FICI[2] |
| K. pneumoniae 1346 | MB-11 | 0.5 | Cefotaxime | 0.06 | 1.37 |
| K. pneumoniae 1355 | | 0.5 | | 0.06 | 1.87 |
| K. pneumoniae 2238 | | 0.5 | | 8 | 1.37 |
| K. pneumoniae 2541 | | 0.5 | | 0.25 | 0.73 |
| K. pneumoniae 2546 | | 0.5 | | 0.25 | 1.37 |
| K. pneumoniae 2549 | | 0.5 | | 0.06 | 1.37 |
| P. aeruginosa 103 | | 1 | | 16 | 1.12 |

[1]MIC, Minimum Inhibitory Concentration
[2]FICI, Fractional Inhibitory Concentration Index

TABLE 45

Summary of Minimum Inhibitory Concentration and Fractional Inhibitory Concentration Results for MB-11 and Cefepime

| | Compound 1 | | Compound 2 | | |
|---|---|---|---|---|---|
| Organism[1] | Name | MIC[1] (µg/mL) Alone | Name | MIC (µg/mL) Alone | FICI[2] |
| P. aeruginosa 1381 | MB-11 | 1 | Cefepime | 32 | 1.12 |
| P. aeruginosa 1384 | | 1 | | 2 | 1.12 |
| P. aeruginosa 1474 | | 0.5 | | 2 | 1.12 |
| P. aeruginosa 1479 | | 0.5 | | 8 | 0.87 |
| P. aeruginosa 2566 | | 0.5 | | 16 | 0.93 |
| P. aeruginosa 2568 | | 0.5 | | 2 | 0.87 |
| P. aeruginosa 103 | | 1 | | 1 | 0.12 |

[1]MIC, Minimum Inhibitory Concentration
[2]FICI, Fractional Inhibitory Concentration Index

TABLE 46

Summary of Minimum Inhibitory Concentration and Fractional Inhibitory Concentration Results for MB-2B and Cefotaxime

| | Compound 1 | | Compound 2 | | |
|---|---|---|---|---|---|
| Organism[1] | Name | MIC[1] (µg/mL) Alone | Name | MIC (µg/mL) Alone | FICI[2] |
| K. pneumoniae 1346 | MB-2B | 4 | Cefotaxime | 0.06 | 1.19 |
| K. pneumoniae 1355 | | 4 | | 0.06 | 1.19 |
| K. pneumoniae 2238 | | 4 | | 8 | 1.64 |
| K. pneumoniae 2541 | | 8 | | 0.25 | 0.64 |
| K. pneumoniae 2546 | | 8 | | 0.25 | 1.16 |
| K. pneumoniae 2549 | | 8 | | 0.12 | 0.83 |
| P. aeruginosa 103 | | 2 | | 16 | 1.11 |

[1]MIC, Minimum Inhibitory Concentration
[2]FICI, Fractional Inhibitory Concentration Index

TABLE 47

Summary of Minimum Inhibitory Concentration and Fractional Inhibitory Concentration Results for MB-2B and Cefepime

| | Compound 1 | | Compound 2 | | |
|---|---|---|---|---|---|
| Organism[1] | Name | MIC[1] (µg/mL) Alone | Name | MIC (µg/mL) Alone | FICI[2] |
| P. aeruginosa 1381 | MB-2B | 4 | Cefepime | 32 | 1.09 |
| P. aeruginosa 1384 | | 4 | | 2 | 0.94 |
| P. aeruginosa 1474 | | 2 | | 2 | 0.98 |

TABLE 47-continued

Summary of Minimum Inhibitory Concentration and Fractional Inhibitory Concentration Results for MB-2B and Cefepime

| | Compound 1 | | Compound 2 | | |
|---|---|---|---|---|---|
| Organism[1] | Name | MIC[1] (μg/mL) Alone | Name | MIC (μg/mL) Alone | FICI[2] |
| P. aeruginosa 1479 | | 2 | | 4 | 1.11 |
| P. aeruginosa 2566 | | 2 | | 8 | 1.23 |
| P. aeruginosa 2568 | | 2 | | 2 | 1.11 |
| P. aeruginosa 103 | | 2 | | 2 | 0.61 |

[1]MIC, Minimum Inhibitory Concentration
[2]FICI, Fractional Inhibitory Concentration Index Example 11

The Effect of Bismuth Thiols on Infection in a Rattus Norvegicus Femur Critical Defect The current standard of care for open fractures is irrigation, debridement and antibiotics; this is intended to reduce the bacterial load in the wound to the point that infection does not occur. Despite these treatments, infections still complicate up to 75% of severe combat open tibia fractures. Interestingly, even though early infections are often caused by gram negative bacteria, late infections that are implicated in healing problems and amputation are due to gram positive infections, frequently Staphylococci species (Johnson 2007).

One of the reasons that S. aureus are resistant to standard treatment is their ability to form a biofilm. Bacteria in biofilms are able to resist concentrations of antimicrobial compounds which would kill similar organisms in a culture medium (Costerton 1987).

The aim of this study was to determine whether BTs will reduce infection in a contaminated open fracture model either on their own or with antibiotics. The contaminated rat femur critical defect model is a well-accepted model and was used for the experiments described in this Example. This model offers a standardized model for comparing various possible treatments and their effects on reducing infection and/or improving healing.

Compounds (CPD) CPD-8-2 (bismuth pyrithione/butanedithiol; Table 1) and CPD-11 (bismuth pyrithione/ethanedithiol; Table 1) are two analogues of BIS-Bis that have shown potential against Biofilm secreting bacteria in vitro, though with a different spectrum of activity than Bis-EDT.

The three BT formulations, Bis-EDT, CPD-11 and CPD-8-2 (see Table 1) demonstrated inhibitory effects on S. aureus strains in vitro when used with and without Tobramicin and Vancomycin in a Poly Methyl Methacrylate (PMMA) cement bead vehicle. Three formulations of microparticulate BTs were produced in a clinically useful hydrogel gel form as described herein. These BTs were tested suspended in a gel at a concentration of 5 mg/ml$^{-1}$ as has been found to be an appropriate concentration for gel delivery. The gel formulations conformed to the wound contours, and did not require removal following application.

Two treatment arms were used: in the first arm, BT was used singularly; in the second arm BT was used in conjunction with a systemic antibiotic (ABx).

(a) BT Singularly.

Six hours after inoculation with S. aureus, the wound was debrided, irrigated with saline and 1 ml of BT gel inserted within the defect.

(b) BT with Systemic Antibiotics (ABx).

Six hours after inoculation with S. aureus, the wound was debrided, irrigated with saline and 1 ml of BT gel added inserted within the defect. The antibiotic used was Cefazolin at a dose equivalent to 5 mgKg$^{-1}$ delivered via sub-cutaneous injection twice daily for a total of 3-days following the injury. The first dose was administered immediately prior to debridement. Previous data suggested that this dose would result in a reduction in bacteria levels from $\approx 10^6$ to $\approx 10^4$ and therefore still allow the relative effect of different BTs to be measured.

(c) Control

Six hours after inoculation with S. aureus, the wound was debrided and irrigated with saline. The control animals were also treated with Cefazolin as per the regime described above.

Procedure:

The procedure for the in vivo rat injury model was performed as described by Chen et al. (2002 J. Orthop. Res. 20:142; 2005 J. Orthop. Res. 23:816; 2006 J. Bone Joint Surg. Am. 88:1510; 2007 J. Orthop. Trauma 21:693). The rats were anesthetized and prepped for surgery. The anterolateral aspect of the femoral shaft was exposed through a 3-cm incision. The periosteum and attached muscle was stripped from the bone. A polyacetyl plate (27×4×4 mm) was placed on the anterolateral surface of the femur. The plates were predrilled to accept 0.9-mm diameter threaded Kirschner wires. The bases of these plates were formed to fit the contour of the femoral shaft. Pilot holes were drilled through both cortices of the femur using the plate as a template and threaded Kirschner wire was inserted through the plate and femur. The notches that were 6 mm apart on the plate served as a guide for bone removal. A small oscillating saw was used to create the defect while the tissue was cooled by continuous irrigation in an effort to prevent thermal damage.

Several groups of 10 animals each were inoculated with 1×10$^5$ CFU of S. aureus and treated with BT alone or in combination with antibiotics 6 hours post-inoculation as described above. The groups were as follows: Bis-EDT gel; MB-11 gel; MB-8-2 gel; Bis-EDT gel & Abx; MB-11 gel & Abx; MB-8-2 gel & Abx; Control (Abx alone).

Figure 7:
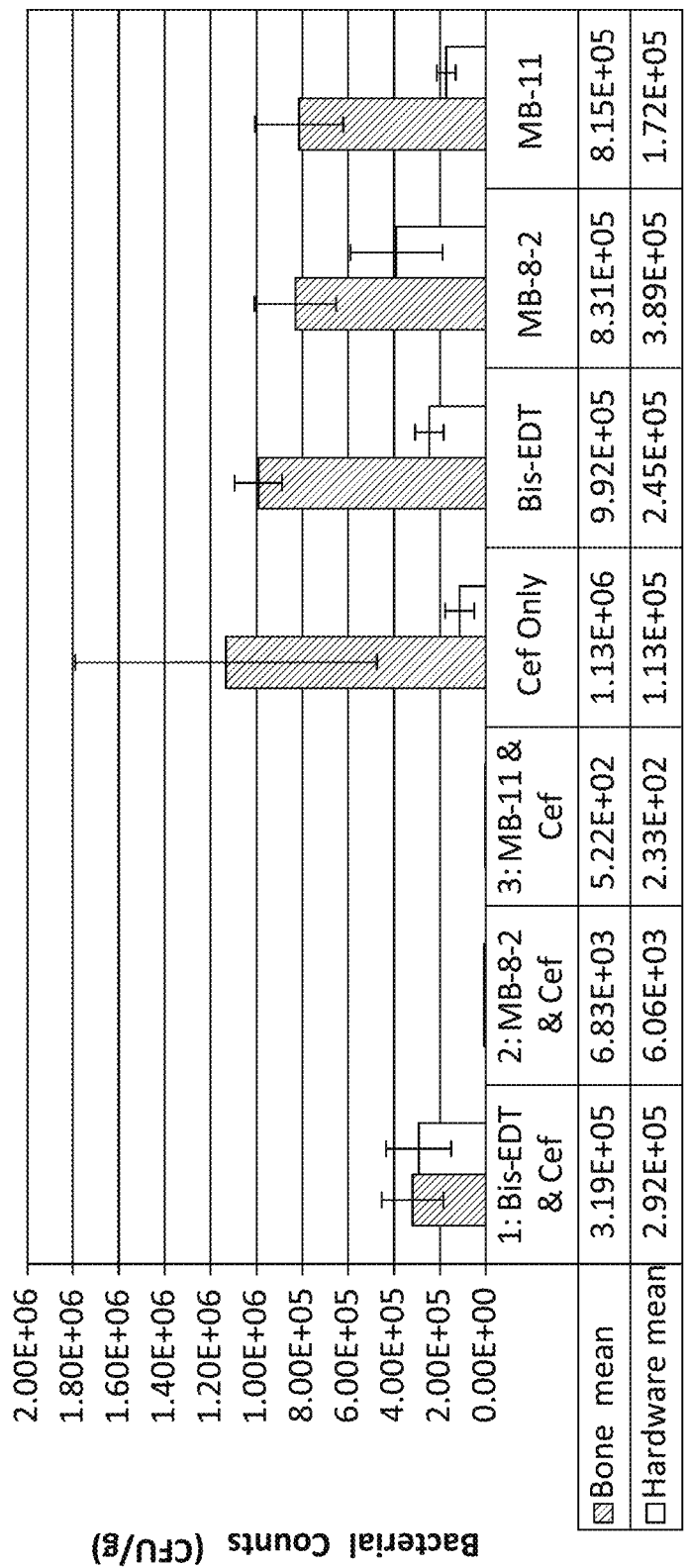
FIG. 7 is a bar graph showing the mean *S. aureus* bacteria levels detected on the bone and hardware samples from open fractures in an in vivo rat model following treatment with three BT formulations, Bis-EDT, MB-11 and MB-8-2 with or without Cefazolin antibiotic treatment. Standard errors of the mean are shown as error bars. Animals euthanized early are not excluded from the analysis, however samples from one animal in group 2 have been excluded due to gross contamination.

Animals were euthanized 14 days after surgery and bone and hardware sent for microbiological analysis, the results of which are shown in FIG. 7.

Based on the power analysis, 10 animals per group will give a power of 80% to detect a 25% difference between the treatment and control groups. This is with an expected standard deviation of 35% and alpha of 0.05.

As shown in FIG. 7, in combination with Bis-EDT, MB-11 and MB-8-2, Cefazolin antibiotic activity was enhanced as compared to Cefazolin or any of the Bis compounds alone to reduce S. aureus infection of injured bone. Cefazolin in combination with MB-11 and MB-8-2 showed enhanced antibiotic activity as compared to Cefazolin alone to reduce S. aureus infection detected on hardware. Bis-EDT did not appear to affect Cefazolin activity in this capacity.

REFERENCES

Costerton J W, Cheng K J, Geesey G G, et al. Bacterial Biofilms in Nature and Disease. *Ann Rev Microbiol.* 1987; 41:435-64

Domenico P, Baldassarri L, Schoch P E, Kaehler K, Sasatsu M, Cunha B A. Activities of Bismuth Thiols against Staphylococci and Staphyloccocal Biofilms. *Antimicrob Agents and Chemother.* 2001; 45(5):1417-21

Halwani M, Blomme S, Suntres Z E, et al. Liposomal bismuth-ethanedithol formulation enhances antimicrobial activity of tobramycin. *Int J. Pharm.* 2008; 358:278-84

Johnson E N, Burns T C, Hayda R A, Hospenthal D R, Murray C K. Infection complications of open type III tibial fractures among combat casualties. *Clin Infect Dis.* 2007; 45(4):409-415

OTHER CITED DOCUMENTS AND RELATED DOCUMENTS

Domenico et al., *Canadian J. Microbiol.* 31:472-78 (1985); Domenico et al., Reduction of capsular polysaccharides and potentation of aminoglycoside inhibition in gram-negative bacteria with bismuth subsalicylate. *J Antimicrob Chemo* 1991; 28:801-810; Domenico et al., *Infection* 20:66-72 (1992); Domenico et al., *Infect. Immun.* 62:4495-99 (1994); Domenico et al., *J. Antimicrol. Chemother.* 38:1031-40 (1996); Domenico et al., Enhancement of bismuth antibacterial activity with lipophilic thiol chelators. *Antimicrob Agents Chemother* 1997; 41:1697-703; Domenico et al., Surface antigen exposure by bismuth-dimercaprol suppression of *Klebsiella pneumoniae* capsular polysaccharide. *Infect Immun* 67:664-669 (1999); Domenico et al., 2000. The potential of bismuth-thiols for treatment and prevention of infection. *Infect Med* 17:123-127; Domenico et al., Activities of bismuth thiols against staphylococci and staphylococcal biofilms. *Antimicrob Agents Chemother* 2001; 45:1417-21; Domenico et al., Combating antibiotic resistance with bismuth-thiols. *Research Advances in Antimicrob Agents Chemother* 2003; 3:79-85; Domenico et al., Reduction of capsular polysaccharides and potentation of aminoglycoside inhibition in gram-negative bacteria with bismuth subsalicylate. *J Antimicrob Chemo* 1991; 28:801-810; Domenico et al., BisEDT and RIP act in synergy to prevent graft infections by resistant staphylococci. *Peptides* 2004.; 25:2047-53; Domenico et al., 2005. Pyrithione enhanced antimicrobial activity of bismuth. *Antibiotics for Clinicians* 9:291-297; U.S. Pat. No. 6,582,719; U.S. RE37,793; U.S. Pat. No. 6,248,371; U.S. Pat. No. 6,086,921; U.S. Pat. No. 6,380,248; U.S. Pat. No. 6,582,719; U.S. Pat. No. 6,380,248; U.S. Pat. No. 6,875,453.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method for protecting a natural surface against one or more of a bacterial pathogen, a fungal pathogen and a viral pathogen, comprising:
    contacting the surface with an effective amount of a BT composition under conditions and for a time sufficient for one or more of:
    (i) prevention of infection of the surface by the bacterial, fungal or viral pathogen,
    (ii) inhibition of cell viability or cell growth of substantially all planktonic cells of the bacterial, fungal or viral pathogen,
    (iii) inhibition of biofilm formation by the bacterial, fungal or viral pathogen, and
    (iv) inhibition of biofilm viability or biofilm growth of substantially all biofilm-form cells of the bacterial, fungal or viral pathogen,
    wherein the BT composition comprises a plurality of solid microparticles that exhibit a unimodal size distribution when the BT composition is analyzed on a particle size analyzer and that comprise a bismuth-thiol (BT) compound that has not been micronized, milled or subjected to super-critical fluid processing, substantially all of said microparticles having a volumetric mean diameter of from about 0.4 µm to about 5 µm, wherein the BT compound comprises bismuth or a bismuth salt and a thiol-containing compound and the BT composition comprises at least one antibiotic compound that is capable of acting synergistically with, or enhancing, the BT compound, wherein the antibiotic compound comprises an antibiotic that is selected from methicillin, vancomycin, nafcillin, gentamicin, ampicillin, chloramphenicol, doxycycline, clindamycin, gatifloxacin, cefazolin and an aminoglycoside antibiotic, and wherein the aminoglycoside antibiotic is selected from the group consisting of amikacin, arbekacin, gentamicin, kanamycin, neomycin, netilmicin, paromomycin, rhodostreptomycin, streptomycin, and apramycin.

2. The method of claim 1 wherein the bacterial pathogen comprises at least one of:
    (i) one or more gram-negative bacteria;
    (ii) one or more gram-positive bacteria;
    (iii) one or more antibiotic-sensitive bacteria;
    (iv) one or more antibiotic-resistant bacteria;
    (v) a bacterial pathogen that is selected from the group consisting of *Staphylococcus aureus* (*S. aureus*), MRSA (methicillin-resistant *S. aureus*), *Staphylococcus epidermidis*, MRSE (methicillin-resistant *S. epidermidis*), *Mycobacterium tuberculosis, Mycobacterium avium, Pseudomonas aeruginosa*, drug-resistant *P. aeruginosa, Escherichia coli*, enterotoxigenic *E. coli*, enterohemorrhagic *E. coli, Klebsiella pneumoniae, Clostridium difficile, Heliobacter pylori, Legionella pneumophila, Enterococcus faecalis*, methicillin-susceptible *Enterococcus faecalis, Enterobacter cloacae, Salmonella typhimurium, Proteus vulgaris, Yersinia enterocolitica, Vibrio cholera, Shigella flexneri*, vancomycin-resistant *Enterococcus* (VRE), *Burkholderia cepacia* complex, *Francisella tularensis, Bacillus anthracis, Yersinia pestis, Pseudomonas aeruginosa, Streptococcus pneumonia*, penicillin-resistant *Streptococcus pneumonia, Escherichia coli, Burkholderia cepacia, Bukholderia multivorans, Mycobacterium smegmatis* and *Acinetobacter baumannii*.

3. The method of claim 1 in which at least one of:
    (a) the bacterial pathogen exhibits resistance to an antibiotic that is selected from the group consisting of methicillin, vancomycin, naficilin, gentamicin, ampicillin, chloramphenicol, doxycycline and tobramycin,
    (b) the surface comprises an epithelial tissue surface that is selected from the group consisting of epidermis, dermis, respiratory tract, gastrointestinal tract and glandular linings,
    (c) the step of contacting is performed one or a plurality of times, (d) at least one step of contacting comprises one of spraying, irrigating, dipping and painting the surface, (e) at least one step of contacting comprises one of inhaling, ingesting and orally irrigating, (f) at least one step of contacting comprises administering to a subject by a route that is selected from topically, intraperitoneally, orally, parenterally, intravenously, intraarterially, transdermally, sublingually, subcutaneously, intramuscularly, transbuccally, intranasally, via inhalation, intraoccularly, intraauricularly, intraventricularly, subcutaneously, intraadiposally, intraarticularly and intrathecally, and (g) the BT composition comprises one or more BT compounds selected from the group consisting of BisBAL, BisEDT, Bis-dimercaprol, Bis-DTT, Bis-2-mercaptoethanol, Bis-DTE, Bis-Pyr, Bis-Ery, Bis-Tol, Bis-BDT, Bis-PDT, Bis-Pyr/Bal, Bis-Pyr/BDT, Bis-Pyr/EDT, Bis-Pyr/PDT, Bis-Pyr/Tol, Bis-Pyr/Ery, bismuth-1-mercapto-2-propanol, and Bis-EDT/2-hydroxy-1-propanethiol.

4. A method for protecting a natural surface against one or more of a bacterial pathogen, a fungal pathogen and a viral pathogen, comprising:

contacting the surface with an effective amount of a BT composition under conditions and for a time sufficient for one or more of:

(i) prevention of infection of the surface by the bacterial, fungal or viral pathogen, (ii) inhibition of cell viability or cell growth of substantially all planktonic cells of the bacterial, fungal or viral pathogen, (iii) inhibition of biofilm formation by the bacterial, fungal or viral pathogen, and (iv) inhibition of biofilm viability or biofilm growth of substantially all biofilm-form cells of the bacterial, fungal or viral pathogen, wherein the BT composition comprises a plurality of solid microparticles that exhibit a unimodal size distribution when the BT composition is analyzed on a particle size analyzer and that comprise a bismuth-thiol (BT) compound which comprises bismuth or a bismuth salt and a thiol-containing compound, substantially all of said microparticles having a volumetric mean diameter of from about 0.4 µm to about 5 µm, wherein at least one of: (a) the synergizing antibiotic or the cooperative antimicrobial efficacy enhancing antibiotic comprises an antibiotic that is selected from the group consisting of an aminoglycoside antibiotic, a carbapenem antibiotic, a cephalosporin antibiotic, a fluoroquinolone antibiotic, a glycopeptide antibiotic, a lincosamide antibiotic, a penicillinase-resistant penicillin antibiotic, and an aminopenicillin antibiotic, and (b) the synergizing antibiotic or the cooperative antimicrobial efficacy enhancing antibiotic is an aminoglycoside antibiotic that is selected from the group consisting of amikacin, arbekacin, gentamicin, kanamycin, neomycin, netilmicin, paromomycin, rhodostreptomycin, streptomycin, tobramycin and apramycin, wherein at least one of:

(a) the bacterial pathogen exhibits resistance to an antibiotic that is selected from the group consisting of methicillin, vancomycin, naficilin, gentamicin, ampicillin, chloramphenicol, doxycycline and tobramycin, (b) the surface comprises an epithelial tissue surface that is selected from the group consisting of epidermis, dermis, respiratory tract, gastrointestinal tract and glandular linings, (c) the step of contacting is performed one or a plurality of times, (d) at least one step of contacting comprises one of spraying, irrigating, dipping and painting the surface, (e) at least one step of contacting comprises one of inhaling, ingesting and orally irrigating, (f) at least one step of contacting comprises administering to a subject by a route that is selected from topically, intraperitoneally, orally, parenterally, intravenously, intraarterially, transdermally, sublingually, subcutaneously, intramuscularly, transbuccally, intranasally, via inhalation, intraoccularly, intraauricularly, intraventricularly, subcutaneously, intraadiposally, intraarticularly and intrathecally, and (g) the BT composition comprises one or more BT compounds selected from the group consisting of BisBAL, BisEDT, Bis-dimercaprol, Bis-DTT, Bis-2-mercaptoethanol, Bis-DTE, Bis-Pyr, Bis-Ery, Bis-Tol, Bis-BDT, Bis-PDT, Bis-Pyr/Bal, Bis-Pyr/BDT, Bis-Pyr/EDT, Bis-Pyr/PDT, Bis-Pyr/Tol, Bis-Pyr/Ery, bismuth-1-mercapto-2-propanol, and Bis-EDT/2-hydroxy-1-propanethiol, and wherein the method further comprises contacting the surface with at least one of (i) a synergizing antibiotic and (ii) a cooperative antimicrobial efficacy enhancing antibiotic, simultaneously or sequentially and in any order with respect to the step of contacting the surface with the composition wherein at least one of: (A) the synergizing antibiotic or the cooperative antimicrobial efficacy enhancing antibiotic comprises an antibiotic that is selected from the group consisting of an aminoglycoside antibiotic, a carbapenem antibiotic, a cephalosporin antibiotic, a fluoroquinolone antibiotic, a glycopeptide antibiotic, a lincosamide antibiotic, a penicillinase-resistant penicillin antibiotic, and an aminopenicillin antibiotic, and (B) the synergizing antibiotic or the cooperative antimicrobial efficacy enhancing antibiotic is an aminoglycoside antibiotic that is selected from the group consisting of amikacin, arbekacin, gentamicin, kanamycin, neomycin, netilmicin, paromomycin, rhodostreptomycin, streptomycin, tobramycin and apramycin.

5. The method of claim 4 which comprises overcoming antibiotic resistance where an antibiotic-resistant bacterial pathogen is present on the natural surface.

6. The method of claim 5 in which at least one of:

(a) the bacterial pathogen is selected from the group consisting of *Staphylococcus aureus* (*S. aureus*), MRSA (methicillin-resistant *S. aureus*), *Staphylococcus epidermidis*, MRSE (methicillin-resistant *S. epidermidis*), *Mycobacterium tuberculosis*, *Mycobacterium avium*, *Pseudomonas aeruginosa*, drug-resistant *P. aeruginosa*, *Escherichia coli*, enterotoxigenic *E. coli*, enterohemorrhagic *E. coli*, *Klebsiella pneumoniae*, *Clostridium difficile*, *Heliobacter pylori*, *Legionella pneumophila*, *Enterococcus faecalis*, methicillin-susceptible *Enterococcus faecalis*, *Enterobacter cloacae*, *Salmonella typhimurium*, *Proteus vulgaris*, *Yersinia enterocolitica*, *Vibrio cholera*, *Shigella flexneri*, vancomycin-resistant *Enterococcus* (VRE), *Burkholderia cepacia* complex, *Francisella tularensis*, *Bacillus anthracis*, *Yersinia pestis*, *Pseudomonas aeruginosa*, *Streptococcus pneumonia*, penicillin-resistant *Streptococcus pneumonia*,

*Escherichia coli, Burkholderia cepacia, Bukholderia multivorans, Mycobacterium smegmatis* and *Acinetobacter baumannii*, (b) the bacterial pathogen exhibits resistance to an antibiotic that is selected from the group consisting of methicillin, vancomycin, naficilin, gentamicin, ampicillin, chloramphenicol, doxycycline, tobramycin, clindamicin and gatifloxacin, (c) the surface comprises an epithelial surface of a tissue that is selected from the group consisting of epidermis, dermis, respiratory tract, gastrointestinal tract and glandular linings, (d) the step of contacting is performed one or a plurality of times, (e) at least one step of contacting comprises one of spraying, irrigating, dipping, coating and painting the surface, (f) at least one step of contacting comprises one of inhaling, ingesting and orally irrigating, (g) at least one step of contacting comprises administering to a subject by a route that is selected from topically, intraperitoneally, orally, parenterally, intravenously, intraarterially, transdermally, sublingually, subcutaneously, intramuscularly, transbuccally, intranasally, via inhalation, intraoccularly, intraauricularly, intraventricularly, subcutaneously, intraadiposally, intraarticularly and intrathecally, (h) the BT composition comprises one or more BT compounds selected from the group consisting of BisBAL, BisEDT, Bis-dimercaprol, Bis-DTT, Bis-2-mercaptoethanol, Bis-DTE, Bis-Pyr, Bis-Ery, Bis-Tol, Bis-BDT, Bis-PDT, Bis-Pyr/Bal, Bis-Pyr/BDT, Bis-Pyr/EDT, Bis-Pyr/PDT, Bis-Pyr/Tol, Bis-Pyr/Ery, bismuth-1-mercapto-2-propanol, and Bis-EDT/2-hydroxy-1-propanethiol.

7. An antiseptic composition for treating a natural surface that contains bacterial biofilm, comprising at least one of:

(1) a composition that comprises (a) at least one BT composition that comprises a plurality of solid microparticles that exhibit a unimodal size distribution when the composition is analyzed on a particle size analyzer and that comprise a bismuth-thiol (BT) compound which comprises bismuth or a bismuth salt and a thiol-containing compound, substantially all of said microparticles having a volumetric mean diameter of from about 0.4 µm to about 5 µm; and (b) at least one antibiotic compound that is capable of acting synergistically with, or enhancing, the BT compound, wherein the antibiotic compound comprises an antibiotic that is selected from methicillin, vancomycin, nafcillin, gentamicin, ampicillin, chloramphenicol, doxycycline, clindamycin, gatifloxacin, cefazolin and an aminoglycoside antibiotic, and (2) the composition of (1) wherein the aminoglycoside antibiotic is selected from the group consisting of amikacin, arbekacin, gentamicin, kanamycin, neomycin, netilmicin, paromomycin, rhodostreptomycin, streptomycin, and apramycin.

8. The composition of claim 7 wherein the BT compound is selected from the group consisting of BisBAL, BisEDT, Bis-dimercaprol, Bis-DTT, Bis-2-mercaptoethanol, Bis-DTE, Bis-Pyr, Bis-Ery, Bis-Tol, Bis-BDT, Bis-PDT, Bis-Pyr/Bal, Bis-Pyr/BDT, Bis-Pyr/EDT, Bis-Pyr/PDT, Bis-Pyr/Tol, Bis-Pyr/Ery, bismuth-1-mercapto-2-propanol, and Bis-EDT/2-hydroxy-1-propanethiol.

9. A method for treating a natural surface that contains bacterial biofilm, comprising:

(a) identifying a bacterial infection in or on the surface as comprising one of (i) gram positive bacteria, (ii) gram negative bacteria, and (iii) both (i) and (ii); and (b) administering to the surface a formulation that comprises one or more bismuth thiol (BT) compositions and at least one antibiotic compound that is capable of acting synergistically with, or enhancing, the BT compound, wherein the antibiotic compound comprises an antibiotic that is selected from methicillin, vancomycin, nafcillin, gentamicin, ampicillin, chloramphenicol, clindamycin, gatifloxacin, cefazolin and an aminoglycoside antibiotic, and wherein the aminoglycoside antibiotic is selected from the group consisting of amikacin, arbekacin, gentamicin, kanamycin, neomycin, netilmicin, paromomycin, rhodostreptomycin, streptomycin, and apramycin, wherein:

(i) if the bacterial infection comprises gram positive bacteria, then the formulation comprises effective amounts of at least one BT compound and at least one antibiotic that is rifamycin, (ii) if the bacterial infection comprises gram negative bacteria, then the formulation comprises effective amounts of at least one BT compound and amikacin, (iii) if the bacterial infection comprises both gram positive and gram negative bacteria, then the formulation comprises effective amounts of one or a plurality of BT compounds, rifamycin and amikacin, and thereby treating the surface, wherein the BT compound comprises bismuth or a bismuth salt and a thiol-containing compound.

10. The method of claim 9 wherein the bacterial infection comprises one or a plurality of antibiotic-resistant bacteria.

11. The method of claim 10 wherein treating comprises at least one of: (i) eradicating the bacterial biofilm, (ii) reducing the bacterial biofilm, and (iii) impairing growth of the bacterial biofilm.

12. The method of claim 9 wherein the BT composition comprises a plurality of solid microparticles that exhibit a unimodal size distribution when the composition is analyzed on a particle size analyzer and that comprise a bismuth-thiol (BT) compound, substantially all of said microparticles having a volumetric mean diameter of from about 0.4 µm to about 5 µm, wherein the BT compound comprises bismuth or a bismuth salt and a thiol-containing compound.

13. The method of claim 12 wherein the BT compound has not been micronized, milled or subjected to super-critical fluid processing.

* * * * *